US011452759B2

(12) United States Patent
Ciechanover et al.

(10) Patent No.: US 11,452,759 B2
(45) Date of Patent: Sep. 27, 2022

(54) UBIQUITIN LIGASE KPC1 PROMOTES PROCESSING OF P105 NF-κB1 TO P50, ELICITING STRONG TUMOR SUPPRESSION

(71) Applicant: TECHNION RESEARCH & DEVELOPMENT FOUNDATION LIMITED, Haifa (IL)

(72) Inventors: Aaron Ciechanover, Caesarea (IL); Yelena Kravtsova, Haifa (IL); Inna Shomer, Herzilya (IL); Victoria Cohen, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 840 days.

(21) Appl. No.: 15/544,523

(22) PCT Filed: Jan. 5, 2016

(86) PCT No.: PCT/IL2016/050009
§ 371 (c)(1),
(2) Date: Dec. 4, 2017

(87) PCT Pub. No.: WO2016/116922
PCT Pub. Date: Jul. 28, 2016

(65) Prior Publication Data
US 2018/0140667 A1    May 24, 2018

Related U.S. Application Data

(60) Provisional application No. 62/104,883, filed on Jan. 19, 2015.

(51) Int. Cl.
*A61K 38/17* (2006.01)
*C07K 19/00* (2006.01)
*A61P 35/00* (2006.01)
*C12P 21/02* (2006.01)

(52) U.S. Cl.
CPC .............. *A61K 38/17* (2013.01); *A61P 35/00* (2018.01); *C07K 19/00* (2013.01); *C12P 21/02* (2013.01); *C07K 2317/76* (2013.01); *C07K 2319/30* (2013.01)

(58) Field of Classification Search
CPC .... A61K 48/00; A61K 31/7088; A61K 38/17; A61K 38/1709; C12N 15/00; A61P 35/00; A61P 35/04; C07K 14/435; C07K 2319/00; C07K 19/00; C07K 2319/30
See application file for complete search history.

(56) References Cited

U.S. PATENT DOCUMENTS 5,916,803 A * 6/1999 Sedlacek ............... A61P 35/00
435/325
6,429,200 B1 * 8/2002 Monahan ............ A61K 48/0025
536/23.1

2004/0005569 A1    1/2004  Baker et al.
2009/0215709 A1 *  8/2009  Van Criekinge ........ A61P 35/04
514/34
2014/0079770 A1 *  3/2014  Kusumoto ........... A61K 9/1271
530/324

FOREIGN PATENT DOCUMENTS

| WO | WO-0134206 A2 * | 5/2001 | ........... A61K 47/643 |
| WO | WO-02057424 A2 * | 7/2002 | ............. A61K 47/10 |
| WO | WO2003100064 A1 | 12/2003 | |
| WO | WO2008134752 A2 | 11/2008 | |
| WO | WO-2011026641 A1 * | 3/2011 | ............. A61K 39/35 |
| WO | WO-2014039012 A1 * | 3/2014 | ........... A61K 31/216 |
| WO | WO-2015093557 A1 * | 6/2015 | ........... C07K 14/705 |

OTHER PUBLICATIONS

Machine Translation of WO2015/093557, Jun. 5, 2020. (Year: 2020).*
Heitz et al, British Journal of Pharmacology, 2009, vol. 157, pp. 195-206 (Year: 2009).*
Kauffman et al (Trends in Biochemical Sciences, 2015, vol. 40, pp. 749-764) (Year: 2015).*
Wold and Toth, Author Manuscript, Current Gene Therapy, Jul. 20, 2015, 26 pages (Year: 2015).*
Appaiahgari and Vrati (Expert Opinion in Biological Therapy, 2015, vol. 15, pp. 337-351) (Year: 2015).*
Nayerssadat et al (Advances in Biomedical Research, 2012, vol. 1, No. 27, 22 pages) (Year: 2012).*
Kigel et al (PLoS One, 2008, vol. 3,e3287, 14 pages). (Year: 2008).*
Trubetskoy et al, Bioconjugate Chemistry, 1992, vol. 3, pp. 323-327 (Year: 1992).*
The abstract of Chen et al, Hyaluronan, Proceedings of the International Cellucon Conference, 2002, vol. 1, pp. 305-311 (Year: 2002).*
Mumper et al, Pharmaceutical Research, 1996, vol. 13, pp. 701-709 (Year: 1996).*
Murata et al, Bioorganic and Medicinal Chemistry Letters, 2003, vol. 13, pp. 3967-3970 (Year: 2003).*
Hayes et al, Biochimica et Biophysica Acata, 2006, vol. 1758, No. 4, pp. 429-442 (Year: 2006).*
Pitard et al, PNAS, 1997, vol. 94, pp. 14412-14417 (Year: 1997).*
Mayurkumar, International Journal of Pharmaceutics, 2013, vol. 453, pp. 400-407 (Year: 2013).*
Xiaopin, International Journal of Nanomedicine, 2012, vol. 7, pp. 4961-4972 (Year: 2012).*
Xu et al, Biomaterials, 2008, vol. 29, pp. 3023-3033 (Year: 2008).*
Huang et al, Journal of Pharmaceutical Sciences, 2002, vol. 91, pp. 1371-1381 (Year: 2002).*

(Continued)

*Primary Examiner* — Karen A. Canella
(74) *Attorney, Agent, or Firm* — Pearl Cohen Zedek Latzer Baratz LLP

(57) ABSTRACT

The invention provides a method for treating cancer comprising the step of administering a therapeutically effective amount of KPC1, a peptide which is at least about 70% homologous to the KPC1 or an agent which up-regulates KPC1. In some embodiments, there is also provided a method for treating cancer comprising the step of administering a therapeutically effective amount of p50, a peptide which is at least about 70% homologous to the p50 or an agent which up-regulates p50.

7 Claims, 45 Drawing Sheets
Specification includes a Sequence Listing.

(56) References Cited

OTHER PUBLICATIONS

Hayes et al., Biochmica et Biophysica Acta, 2006, vol. 1758, pp. 429-442 (Year: 2006).*
Kamura et al., "Cytoplasmic ubiquitin ligase KPC regulates proteolysis of p27Kip1 at G1 phase" Nature Cell Biology, Dec. 2004, vol. 6, No. 12, pp. 1229-1239.
Saccani et al. "p50 Nuclear Factor-KB Overexpression in Tumor-Associated Macrophages Inhibits M1 Inflammatory Responses and Antitumor Resistance", Dec. 1, 2006, The Journal Cancer Research, vol. 66 No. 23, pp. 11432-11440.
Kravtsova-Ivantsiv et al, "The ubiquitin-proteasome system and activation of NF-κB: involvement of the ubiquitin ligase KPC1 in p105 processing and tumor suppression", Molecular & Cellular Oncology, May 26, 2015, pp. 1-4.
Kravtsova-Ivantsiv et al. "KPC1-Mediated Ubiquitination and Proteasomal Processing of NF-κB1 p105 to p50 Restricts Tumor Growth" Cell, Apr. 9, 2015, vol. 161, No. 2, pp. 333-347.
Czajkowsky et al. Fc-fusion proteins: new developments and future perspectives. *EMBO Mol Med*. 2012;4(10):1015-1028.
Linderholm et al. Immunoglobulin FC-Fusion Proteins. *BioProcess International* Nov. 2014. https://bioprocessintl.com/manufacturing/monoclonal-antibodies/immunoglobulin-fc-fusion-proteins-part-2-therapeutic-uses-clinical-development.
Dufresne & Duval. Genetic sequences: how are they patented? *Nat Biotechnol*. 2004;22(2):231-232.
Reeck et al. "Homology" in proteins and nucleic acids: a terminology muddle and a way out of it. *Cell*. 1987;50(5):667.
Office Action of European Patent Application No. EP16739877.5, dated Feb. 24, 2020.
Akiri et al. (2009). Wnt pathway aberrations including autocrine Wnt activation occur at high frequency in human non-small-cell lung carcinoma. Oncogene, 28(21), 2163-2172.
Anders et al. (2015). HTSeq-a Python framework to work with high-throughput sequencing data. Bioinformatics (Oxford, England), 31(2), 166-169.
Barré et al. (2007). A cell cycle regulatory network controlling NF-kappaB subunit activity and function. The EMBO journal, 26(23), 4841-4855.
Barré et al. (2010). Regulation of activity and function of the p52 NF-κB subunit following DNA damage. Cell cycle (Georgetown, Tex.), 9(24), 4795-4804.
Ben-Neriah, Y., & Karin, M. (2011). Inflammation meets cancer, with NF-κB as the matchmaker. Nature immunology, 12(8), 715-723.
Betts, J. C., & Nabel, G. J. (1996). Differential regulation of NF-kappaB2(p100) processing and control by amino-terminal sequences. Molecular and cellular biology, 16(11), 6363-6371.
Bitter et al. (1987). Expression and secretion vectors for yeast. Methods in enzymology, 153, 516-544.
Bonavia et al. (2011). Heterogeneity maintenance in glioblastoma: a social network. Cancer research, 71(12), 4055-4060.0.
Booth et al. (1988). The use of a 'universal' yeast expression vector to produce an antigenic protein of Mycobacterium leprae. Immunology letters, 19(1), 65-69.
Bowie et al. (1990). Deciphering the message in protein sequences: tolerance to amino acid substitutions. Science (New York, N.Y.), 247(4948), 1306-1310.
Broglie et al. (1984). Light-regulated expression of a pea ribulose-1,5-bisphosphate carboxylase small subunit gene in transformed plant cells. Science (New York, N.Y.), 224(4651), 838-843.
Cohen et al. (2004). Dual effects of IkappaB kinase beta-mediated phosphorylation on p105 Fate: SCF(beta-TrCP)-dependent degradation and SCF(beta-TrCP)-independent processing. Mol. Cell Biol. 24, 475-486.
Coruzzi et al. (1984). Tissue-specific and light-regulated expression of a pea nuclear gene encoding the small subunit of ribulose-1,5-bisphosphate carboxylase. The EMBO journal, 3(8), 1671-1679.
Dennis et al. (2003). DAVID: Database for Annotation, Visualization, and Integrated Discovery. Genome biology, 4(5), P3.

Deng and Wu (2003). Regulation of inducible nitric oxide synthase expression by p300 and p50 acetylation. J. Immunol. 171, 6581-6588.
DiDonato et al. (2012). NF-kappaB and the link between inflammation and cancer. Immunol. Rev. 246, 379-400.
Fan and Maniatis (1991). Generation of p50 subunit of NF-kappa B by processing of 0105 through an ATP-dependent pathway. Nature 354, 395-398.
Fujita et al. (1993). The candidate proto-oncogene bcl-3 encodes a transcriptional coactivator that activates through NF-kappa B p50 homodimers. Genes Dev. 7, 1354-1363.
Gao et al. (2009). Loss of NECL1, a novel tumor suppressor, can be restored in glioma by HDAC inhibitor-Trichostatin A through Sp1 binding site. Glia 57, 989-999.
Gardella et al. (1990). Expression of human parathyroid hormone-(1-84) in *Escherichia coli* as a factor X-cleavable fusion protein. The Journal of biological chemistry, 265(26), 15854-15859.
Gurley et al. (1986). Upstream sequences required for efficient expression of a soybean heat shock gene. Molecular and cellular biology, 6(2), 559-565.
Hara et al. (2005). Role of the UBL-UBA protein KPC2 in degradation of p27 at G1 phase of the cell cycle. Mol. Cell Biol. 25, 9292-9303.
Heddleston et al. (2009). The hypoxic microenvironment maintains glioblastoma stem cells and promotes reprogramming towards a cancer stem cell phenotype. Cell Cycle 8, 3274-3284.
Heissmeyer et al. (2001). Shared pathways of IkappaB kinase-induced SCF(betaTrCP)-mediated ubiquitination and degradation for the NF-kappaB precursor p105 and IkappaBalpha. Mol. Cell Biol. 21, 1024-1035.
Hershko et al. (1983). Components of ubiquitin-protein ligase system. Resolution, affinity purification, and role in protein breakdown. J. Biol. Chem. 258, 8206-8214.
Ivanov et al. (1997). Regulation of Fas-dependent activation-induced T cell apoptosis by cAMP signaling: a potential role for transcription factor NF-kappa B. Oncogene 14, 2455-2464.
Kontermann (2011). Strategies for extended serum half-life of protein therapeutics. Current opinion in biotechnology, 22(6), 868-876.
Kravtsova-Ivantsiv et al. (2009). Modification by single ubiquitin moieties rather than polyubiquitination is sufficient for proteasomal processing of the p105 NF-kappaB precursor. Mol. Cell 33, 496-504.
Lin and Ghosh (1996). A glycine-rich region in NF-kappaB p105 functions as a processing signal for the generation of the p50 subunit. Mol. Cell Biol. 16, 2248-2254.
Lin et al. (1998). Cotranslational biogenesis of NF-kappaB p50 by the 26S proteasome. Cell 92, 819-828.
Mackichan et al. (1996). Phosphorylation of p105 PEST sequence via a redoxinsensitive pathway up-regulates processing of p50 NF-kappaB. J. Biol. Chem. 271, 6084-6091.
May and Ghosh. (1997). Rel/NF-kappa B and I kappa B proteins: an overview. Semin. Cancer Biol. 8, 63-73.
Mercer et al. (2012). RNAi screening reveals proteasome- and Cullin3-dependent stages in vaccinia virus infection. Cell reports, 2(4), 1036-1047.
Mercurio et al. (1997). IKK-1 and IKK-2: cytokine-activated IkappaB kinases essential for NF-kappaB activation. Science 278, 860-866.
Orian et al. (2000). SCF(beta)(-TrCP) ubiquitin ligase-mediated processing of NF-kappaB p105 requires phosphorylation of its C-terminus by IkappaB kinase. EMBO J. 19, 2580-2591.
Palombella et al. (1994). The ubiquitin-proteasome pathway is required for processing the NF-kB1 precursor protein and the activation of NF-kappa B. Cell 78, 773-785.
Perkins (2012). The diverse and complex roles of NF-kappaB subunits in cancer. Nat. Rev. Cancer 12, 121-132.
Perrella et al. (1999). High mobility group-I(Y) protein facilitates nuclear factor-kappaB binding and transactivation of the inducible nitric-oxide synthase promoter/enhancer. J. Biol. Chem. 274, 9045-9052.
Pikarsky and Ben-Neriah. (2006). NF-kappaB inhibition: a double-edged sword in cancer? Eur. J. Cancer 42, 779-784.

(56) References Cited

OTHER PUBLICATIONS

Rahman and Mcfadden (2011). Modulation of NF-kappaB signalling by microbial pathogens. Nat. Rev. Microbiol. 9, 291-306.

Salmeron et al. (2001). Direct phosphorylation of NF-kappaB1 0105 by the IkappaB kinase complex on serine 927 is essential for signal-induced p105 proteolysis. J. Biol. Chem. 276, 22215-22222.

Senftleben et al. (2001). Activation by IKKalpha of a second, evolutionary conserved, NF-kappa B signaling pathway. Science 293, 1495-1499).

Siggers et al. (2012). Principles of dimer-specific gene regulation revealed by a comprehensive characterization of NF-kappaB family DNA binding. Nat. Immunol. 13, 95-102.

Studier et al. (1990). Use of T7 RNA polymerase to direct expression of cloned genes. Methods in enzymology, 185, 60-89.

Szklarczyk et al. (2011). The STRING database in 2011: functional interaction networks of proteins, globally integrated and scored. Nucleic Acids Res. 39, D561-568).

Takamatsu et al. (1987). Expression of bacterial chloramphenicol acetyltransferase gene in tobacco plants mediated by TMV-RNA. The EMBO journal, 6(2), 307-311.

Trapnell et al. (2009). TopHat: discovering splice junctions with RNA-Seq. Bioinformatics 25, 1105-1111.

Voce et al. (2015). Nfkb1 is a haploinsufficient DNA damage-specific tumor suppressor. Oncogene, 34(21), 2807-2813.

Weissbach & Weissbach (1988) Methods for Plant Molecular Biology, Academic Press, NY, Section VIII, pp. 421-463.

Zaaroor-Regev et al. (2010). Regulation of the polycomb protein Ring1B by self-ubiquitination or by E6-AP may have implications to the pathogenesis of Angelman syndrome. Proc. Natl. Acad. Sci U S A 107, 6788-6793.

Zhao et al. (2013). TSGene: a web resource for tumor suppressor genes. Nucleic Acids Res. 41, D970-976.

\* cited by examiner

KPC1 rabbit Coverage: 43.21%  Seq. ID No. 20

```
   1   101   201   301   401   501   601   701   801   901  1001  1101  1201  1301  1333
```

```
   1  MASKGAGVPL SRKSYRLTSE TERPRVTGIV HEKLLNDYLH RIFSSPDHAT PTATSRKPLN
  61  FQNLPEHLDQ LLQVDSEDEE SQGQVEGRLG PSTVVLDHTG GFEGLLLVDD DLLGVIGHSN
 121  FGTIRSTTCV YKGKWVYEVL ISSQGLMQIG WCTINCRFNQ EEQVGDTHNS YAYDGNRVRK
 181  WNVTTTNYGK AWAAGDIVSC LIDLDDGTLS FCLNGVSLGT AFENLSRGLG MAYFPAISLS
 241  FKESVAFNFG SRPLRYPVAG YRPLQDPPCA DLTRAQRLLG CFRAVLSVEL DPMEGRLVEK
 301  ESSEWQLQGQ PTVLLTLAHI FHRFAPLLHQ VYLVEAVLMS FLLGIVEKAT PAQAQSAVHQ
 361  ILDLLWLFME DYEVQDCLKQ LMMSLLRLYR FSPIVPDLGL QIHYLRLTIA ILRHQKSRKF
 421  LLSNVLFDVL RSVVFFYIKS PLRVEEAGLQ ELIPTTWWPH RSSREGKDSA EDRAEAAEER
 481  PRRRAYERGC QRLKKRIEVV EALQVQILKL LLDNKDDNGG EASRYIFLTK FRKFLQENAS
 541  GRGNMPMLCP PEYMVCFLHR LISLRYYWDE YKASNPRASC SEEAYIPPQV FYNGKVDYFD
 601  LQRLGGLLSH LRKTLKGVCS PLGXXXXXXX XXXATTMDDL DEDEEPAPAA AGVLHKGQRP
 661  VQALAVGGAL PLPRPGWLSS PTLGRANRFL STAAVSLMTP RRPLSTSEKV KVRTLSVEQR
 721  TREDIEGSHW NEGLLLGRPP EEPEQPLTEN SLLEVLDGAI MMYNLSVHQQ LGKMVGVSDD
 781  VNEYATALRD TEDKIRRCPK RRKDILAELT KSQKVFSEKL DHLSRRLAWV HATVYSQEKM
 841  LDIYWLLRVC LRTIEHGDRT GSLFAFMPEF YLSVAINSYS ALKNYFGPVH SMEELPGYEE
 901  TLTRLAAILA KHFADTRIVG TDIRDSLMQA LASYVCYPHS LRAVERIPEE QRVAMVRSLL
 961  APYEQRPWAQ TNWILVRLWR GCGFGYRYTR LPHLLKTKPE DASLPSLQKP CPSTLLQQHM
1021  ADLLRQGPDV APSFLNSVLN QLNWAFSEFI GMIQEIQQAA ERLERNFVDS RQLKVCATCF
1081  DLSVSLLRVL EMTITLVPEI FLDWARPTSE MLLRRLAQLL NQVLNRVTAE RNLFDRVVTL
1141  RLPGLESVDH YPILVAVTGI LVRLLVHGPS SETERATSVL LADPCFQLRS ISYLLGQPEP
1201  PAPGAALPAP DRKRFSLQSY ADYISAEELA QVEQMLAHLT SASAQAAAAS LPTSEEDLCP
1261  ICYAHPISAV FQPCGHKSCK ACIDQHLMNN KDCFFCKATI VSVEDWEKGA SASGAAAAAA
1321  TTTTTTSTS SAA
```

KPC2 mouse Coverage: 19.8%  Seq. ID No. 21

```
   1   101   201   301   409
```

```
   1  MFVQEEKIFA GKVLRLHICA SDGAEWLEEA TEDTSVEKLK ERCLKHCAHG SLEDPKSITH
  61  HKLIHAASER VLSDARTILE ENIQDQDVLL LIKKRAPSPL PKMADVSAEE KKKQDQKAPD
 121  KEAILRATAN LPSYNMDRAA VQTNMRDFQT ELRKILVSLI EVAQKLLALN PDAVELFKKA
 181  NAMLDEDEDE RVDEAALRQL TEMGFPEIRA TKALQLNHMS VPQAMEWLIE HAEDPTIDTP
 241  LPGQAPPEAE GATAAASEAA AGASATDEEA RDELTEIFKK IRRKREFRAD ARAVISLMEM
 301  GFDEKEVIDA LRVNNQQNA ACEWLLGDRK PSPEELDKGI DPDSPLFQAI LDNPVVQLGL
 361  TNPKTLLAFE DMLENPLNST QWMNDPETGP VMLQISRIFQ TLNRT
```

| Tissue | | Sample size | Average of KPC1 SI | | KPC1 stained, % | | Nuclear p50, % | |
|---|---|---|---|---|---|---|---|---|
| Head & neck | Normal | 11 | P<0.0001 | 2.6 | P<0.012 | 100 | P<0.0015 | 100 |
| | Cancer | 52 | | 1.12 | | 62 | | 47 |
| Glial cells | Normal | 16 | P<0.03 | 1.625 | N.S. | 100 | P<0.0001 | 75 |
| | Cancer | 192 | | 1.365 | | 84 | | 19.7 |
| Breast | Normal | 20 | N.S. | 1.37 | N.S. | 90 | P<0.0001 | 65 |
| | Cancer | 85 | | 1.25 | | 94 | | 17.6 |

UBIQUITIN LIGASE KPC1 PROMOTES PROCESSING OF P105 NF-κB1 TO P50, ELICITING STRONG TUMOR SUPPRESSION

CROSS REFERENCE TO RELATED APPLICATIONS

This application claims the benefit of U.S. Provisional Application No. 62/104,883, filed on Jan. 19, 2015 and entitled UBIQUITIN LIGASE KPC1 PROMOTES PROCESSING OF P105 NF-KAPPAB1 TO P50, ELICITING STRONG TUMOR SUPPRESSION, which is incorporated in their entirety herein by reference.

BACKGROUND OF THE INVENTION

The NF-κB family of transcription factors is involved in regulation of a variety of genes that control the immune and inflammatory response, cell survival and death, proliferation and differentiation. Recently—150 years after Rudolf Virchow discovered the infiltration of tumors with leukocytes and proposed a linkage between chronic inflammation and malignant transformation—it has been shown that the mechanism(s) that underlies this linkage is mediated largely by the NF-κB family of transcription factors (Ben-Neriah and Karin, 2011; DiDonato et al., 2012). NF-κB is overexpressed in numerous tumors. It up-regulates expression of anti-apoptotic genes such as IAPs, cell cycle promoters, and growth factors and their receptors (DiDonato et al., 2012). Nevertheless, in some cases NF-κB was shown to display strong tumor suppressive characteristics (Perkins, 2012; Pikarsky and Ben-Neriah, 2006). For example, it is involved in regulation of activation-induced apoptosis of T lymphocytes (Ivanov et al., 1997), and in inducing cell cycle arrest and cell death caused by repression of Bcl2, XIAP, Bcl-XL, Cyclin D1 and c-Myc that occurs after cell damage. The arrest and death are mediated by p52 dimers (Barre et al., 2010; Barre and Perkins, 2007). Also, it was shown that NF-κB1−/− cells accumulate alkylator-induced mutations, and NF-κB1−/− mice develop more lymphomas following alkylating agent-induced DNA damage, again suggesting that NF-κB1 can act as a tumor suppressor (Voce et al., 2014).

The family members are mostly heterodimers where one of the subunits—p52 or p50, is the product of limited, ubiquitin- and proteasome-mediated processing of a longer (and inactive) precursor, p100 or p105, respectively (Betts and Nabel, 1996; Fan and Maniatis, 1991). The other subunit is typically a member of the Rel family of proteins (RelA—p65, RelB or c-Rel). At times, p50 and p52 can generate homodimers that cannot act as transcriptional activators since they lack a transactivation domain present in the Rel proteins. In unstimulated cells, the NF-κB dimers are sequestered in the cytosol attached to ankyrin repeats (ARs) of IκB inhibitory proteins (IκB, Bcl3, p100 and p105). A broad array of extracellular signals stimulate degradation of the IκB proteins, resulting in translocation of the dimers to the nucleus where they initiate different transcriptional programs (Rahman and McFadden, 2011).

Proteasomal processing of p105 occurs under both basal conditions and following stimulation, and requires prior ubiquitination (Cohen et al., 2004; MacKichan et al., 1996). One element that was shown to be important in the processing is a long Gly-Ala repeat in the middle of p105 that may serve as a proteasomal "stop signal" (Lin and Ghosh, 1996). In addition to processing, p105 can also undergo complete degradation, releasing NF-κB dimers anchored to its C-terminal ARs domain. Following stimulation, p105 is phosphorylated on serine residues 927 and 932 by IκB kinase (IKKβ) (Salmeron et al., 2001). This modification recruits the beta-Transducin Repeat Containing Protein βTrCP E3 (Orian et al., 2000), resulting in complete degradation of the molecule (Heissmeyer et al., 2001). The ligase(s) involved in processing of p105 under basal conditions as well as following stimulation has remained elusive.

SUMMARY OF THE INVENTION

The invention is directed to a method for treating cancer comprising the step of administering a therapeutically effective amount of KPC1, a peptide which is at least about 70% homologous to the KPC1 sequence as set forth in SEQ ID No. 4 or an agent which up-regulates KPC1; a fused protein comprising KPC1, the peptide which is at least about 70% homologous to the KPC1 sequence as set forth in SEQ ID No. 4 or the agent which up-regulates KPC1; or a complex comprising KPC1 or the peptide which is at least about 70% homologous to the KPC1 sequence as set forth in SEQ ID No. 4 or the agent that upregulates KPC1; or the fused protein that comprises KPC1, the peptide which is at least about 70% homologous to the KPC1 sequence as set forth in SEQ ID No. 4 or the agent which up-regulates KPC1, to a subject in need, thereby treating cancer.

According to another embodiment, the method for treating cancer comprising the step of administering a therapeutically effective amount of functionally related variant of the KPC1 or a functionally active fragment of KPC1, a fused protein comprising the functionally related variant of the KPC1 or the functionally active fragment of KPC1 or a complex comprising the functionally related variant of the KPC1 or the functionally active fragment of KPC1, or the fused protein that comprises the functionally related variant of the KPC1 or the functionally active fragment of KPC1, to a subject in need, thereby treating cancer.

According to another embodiment, the method for treating cancer comprising the step of administering a therapeutically effective amount of p50, peptide which is at least about 70% homologous to the p50 sequence as set forth in SEQ ID No. 3 or an agent which upregulates p50; a fused protein comprising p50 or the peptide which is at least about 70% homologous to the p50 sequence as set forth in SEQ ID No. 3 or the agent which up-regulates p50; or a complex comprising p50, the peptide which is at least about 70% homologous to the p50 sequence as set forth in SEQ ID No. 3 or the agent which upregulates p50 or the fused protein that comprises p50, the peptide which is at least about 70% homologous to the p50 sequence as set forth in SEQ ID No. 3 or the agent which upregulates p50, to a subject in need, thereby treating cancer.

According to another embodiment, the method for treating cancer comprising the step of administering a therapeutically effective amount of functionally related variant of the p50 or a functionally active fragment of p50, a fused protein comprising the functionally related variant of the p50 or the functionally active fragment of p50 or a complex comprising either the functionally related variant of the p50 or the functionally active fragment of p50, the fused protein that comprises the functionally related variant of the p50 or the functionally active fragment of p50 to a subject in need, thereby treating cancer.

According to another embodiment, the method of treating cancer by administering a therapeutically effective amount of a nucleic acid sequence that encodes to KPC1 or to a peptide which is at least about 70% homologous to the KPC1 sequence as set forth in SEQ ID No. 4, or a nucleic acid that encodes to a fused protein comprising KPC1 or peptide which is at least about 70% homologous to the KPC1 sequence as set forth in SEQ ID No. 4, or a nucleic acid that encodes to an agent which up-regulates KPC1 or to a fusion protein comprising thereof.

According to another aspect, the present invention provides a fused protein comprising KPC1 or peptide which is at least about 70% homologous to the KPC1 sequence as set forth in SEQ ID No. 4.

According to another embodiment the KPC1 or the peptide which is at least about 70% homologous to the KPC1 sequence as set forth in SEQ ID No. 4 is attached to a heterologous amino acid sequence.

According to another embodiment the heterologous amino acid sequence comprises an immunoglobulin amino acid sequence.

According to another embodiment the immunoglobulin amino acid sequence comprises IgG.

According to another aspect, the present invention provides a nucleic acid encoding a fused protein comprising KPC1 or peptide which is at least about 70% homologous to the KPC1 sequence as set forth in SEQ ID No. 4.

According to another aspect, the present invention provides a vector comprising a nucleic acid encoding a fused protein comprising KPC1 or peptide which is at least about 70% homologous to the KPC1 sequence as set forth in SEQ ID No. 4.

According to another aspect, the present invention provides a cell transformed with a vector comprising a nucleic acid encoding a fused protein comprising KPC1 or peptide which is at least about 70% homologous to the KPC1 sequence as set forth in SEQ ID No. 4.

According to another aspect, the present invention provides a complex comprising KPC1 or peptide which is at least about 70% homologous to the KPC1 sequence as set forth in SEQ ID No. 4 and non-proteinaceous or proteinaceous moiety.

According to another embodiment the non-proteinaceous moiety is polyethylene glycol (PEG) or derivative thereof, polyvinyl pyrrolidone (PVP), divinyl ether, albumin, maleic anhydride copolymer (DIVEMA), polysialic acid (PSA), poly(styrene comaleic anhydride) (SMA), hyaluronic acid (HA), alginic acid (AA), polyhydroxyethyl methacrylate (Poly-HEMA), glyme or polyisopropylacrylamide or any combination thereof.

According to another aspect, the present invention provides a therapeutically effective amount of KPC1, a peptide which is at least about 70% homologous to the KPC1 sequence as set forth in SEQ ID No. 4 or an agent which up-regulates KPC1; a fused protein comprising KPC1, the peptide which is at least about 70% homologous to the KPC1 sequence as set forth in SEQ ID No. 4 or the agent which up-regulates KPC1; or a complex comprising KPC1, the peptide which is at least about 70% homologous to the KPC1 sequence as set forth in SEQ ID No. 4 or the agent that upregulates KPC1, or the fused protein that comprises KPC1 or the peptide which is at least about 70% homologous to the KPC1 sequence as set forth in SEQ ID No. 4 or the agent which up-regulates KPC1, for treating a cancer.

According to another aspect, the present invention provides a therapeutically effective amount of functionally related variant of the KPC1 or a functionally active fragment of KPC1, a fused protein comprising the functionally related variant of the KPC1 or the functionally active fragment of KPC1 or a complex comprising the functionally related variant of the KPC1 or the functionally active fragment of KPC1, or the fused protein that comprises the functionally related variant of the KPC1 or the functionally active fragment of KPC1 for treating cancer.

According to another aspect, the present invention provides a therapeutically effective amount of p50, peptide which is at least about 70% homologous to the p50 sequence as set forth in SEQ ID No. 3 or an agent which upregulates p50; a fused protein comprising p50 or the peptide which is at least about 70% homologous to the p50 sequence as set forth in SEQ ID No. 3 or the agent which up-regulates p50; or a complex comprising p50, the peptide which is at least about 70% homologous to the p50 sequence as set forth in SEQ ID No. 3 or the agent which upregulates p50 or the fused protein that comprises p50, the peptide which is at least about 70% homologous to the p50 sequence as set forth in SEQ ID No. 3 or the agent which upregulates p50 for treating cancer.

According to another aspect, the present invention provides a therapeutically effective amount of functionally related variant of the p50 or a functionally active fragment of p50, a fused protein comprising the functionally related variant of the p50 or the functionally active fragment of p50 or a complex comprising either the functionally related variant of the p50 or the functionally active fragment of p50, the fused protein that comprises the functionally related variant of the p50 or the functionally active fragment of p50 for treating cancer.

According to another aspect, the present invention provides a therapeutically effective amount of a nucleic acid sequence that encodes to KPC1 or to a peptide which is at least about 70% homologous to the KPC1 sequence as set forth in SEQ ID No. 4, or a nucleic acid that encodes to a fused protein comprising KPC1 or peptide which is at least about 70% homologous to the KPC1 sequence as set forth in SEQ ID No. 4, or a nucleic acid that encodes to an agent which up-regulates KPC1 or to a fusion protein comprising thereof for treating a cancer.

According to another aspect, the present invention provides a method for producing p50 comprising contacting a cell culture preparation which expresses p105 with KPC1, a peptide which is at least about 70% homologous to the KPC1 sequence as set forth in SEQ ID No. 4 or an agent which up-regulates KPC1, thereby producing p50.

In some embodiments of the invention the cancer to be treated by the methods and active ingredients of the invention is breast cancer, bone osteosarcoma or glioblastoma.

In some embodiments of the invention the agent used in the method of treating cancer which upregulates KPC1 activity or expression increases the level of KPC1 or increases the binding between KPC1 and p105.

In some embodiments of the invention, the agent which upregulates KPC1 is an agonist to KPC1 which may be a chemical agent or a small molecule.

BRIEF DESCRIPTION OF THE DRAWINGS

The invention will now be described in connection to certain Examples and embodiments, in a non-limiting manner, with reference to the following illustrative figures, so that it can be more fully understood. In the drawings:

FIG. 1 A-C show the steps of purification and identification of the p105 Ub ligase.

FIG. 1C is a peptide coverage maps of rabbit KPC1 (upper panel) and mouse KPC2 (lower panel). The peptides were identified through mass spectrometric analysis of the E3-containing fractions resolved by the last, Heparin-based column.

Below at the lower panel is a peptide coverage map of mouse KPC2. The peptides were identified through mass spectrometric analysis of the E3-containing fractions resolved by the last, Heparin-based column. Residues marked in Bold and Italics denote differences in sequence between mouse and rabbit.

FIG. 2 A-J show that p105 is a substrate of KPC1 in a cell free system and in cells, both under basal conditions and following signaling.

Figure 2A:
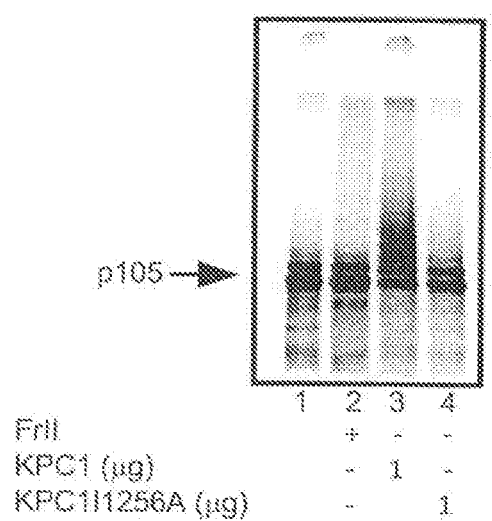

FIG. 2A is an autoradiography image showing ubiquitination of in vitro translated and 35S-labeled p105 by Fraction II and purified KPC1-FLAG-TEV-6×HIS or KPC1I1256A-FLAG-TEV-6×HIS in a reconstituted cell free system. Fr II denotes Fraction II.

Figure 2B:
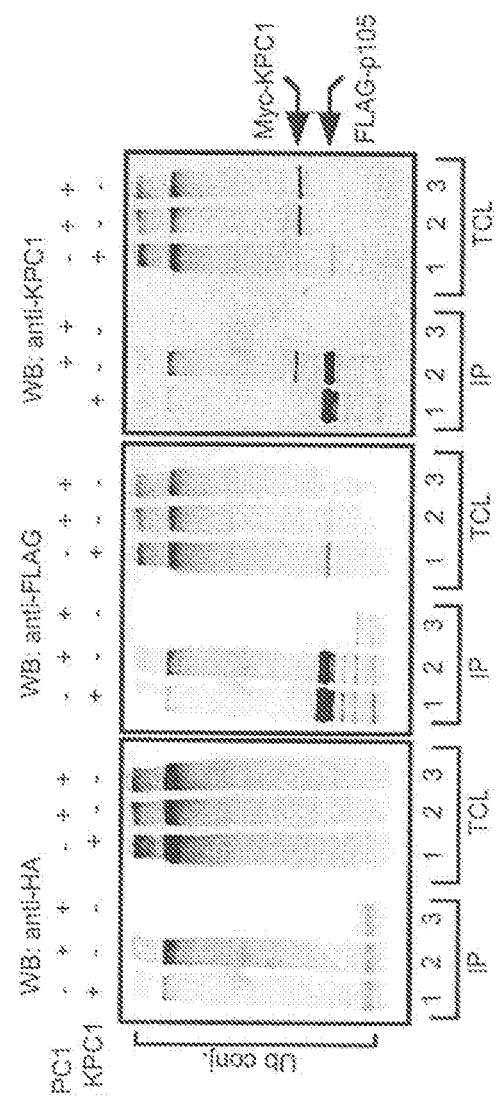

FIG. 2B are western blots showing that KPC1 ubiquitinates p105 in cells. HEK293 cells that were transfected with siRNA to silence KPC1 (lane1) or with control siRNA (lanes 2 and 3), were also transfected with cDNAs coding for FLAG-p105 (lanes 1 and 2), HA-Ub (lanes 1-3), and Myc-KPC1 (lanes 2 and 3). FLAG-p105 and its conjugates were immunoprecipitated from the cell lysates using immobilized anti-FLAG (IP; lanes 1-3), resolved via SDS-PAGE, and visualized using anti-HA (left western blot) or anti-FLAG (middle western blot). KPC1 was visualized using a specific antibody to the protein (right western blot). 10% of total cell lysates (TCL; lanes1-3) were analyzed for expression of FLAG-p105, HA-Ub or Myc-KPC1, using anti-HA (left western blot), anti-FLAG (middle western blot), or anti-KPC1 (right western blot), respectively. IP and WB denote immunoprecipitation and western blot, respectively.

Figure 2C:
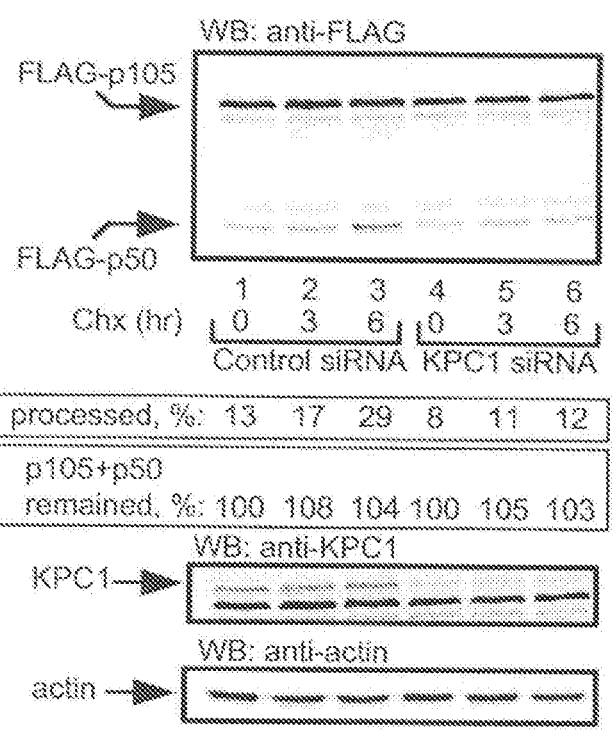

FIG. 2C are western blots showing that silencing of KPC1 affects basal processing of p105. HEK293 cells were transfected with control siRNA (lanes 1-3) or siRNA to silence KPC1 (lanes 4-6). After 24 hr, cells were transfected with cDNAs coding for FLAG-p105. Processing of p105 was calculated as the ratio between the amount p50 at the specified time and the sum of p50+p105 at time zero (in order to disregard degradation of p105 in our calculations), multiplied by 100%. The amount of p50+p105 remained (reflecting degradation along time) was calculated as the sum of p50+p105 measured at the relevant time point, divided by the sum of p50+p105 at time zero, multiplied by 100%.

Figure 2D:
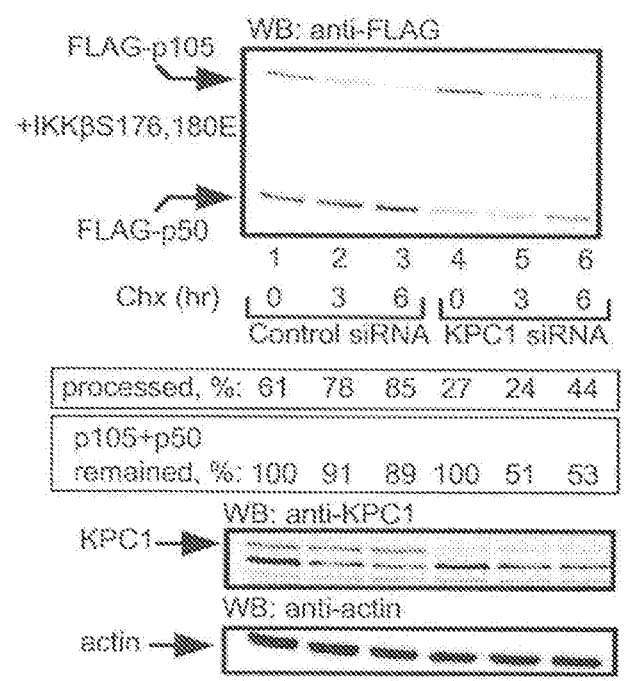

FIG. 2D are western blots showing that silencing of KPC1 inhibits signal-induced processing of p105. HEK293 cells were transfected with control siRNA (lanes 1-3) or siRNA that targets KPC1 (lanes 4-6). After 24 hr, cells were transfected with cDNAs coding for FLAG-p105 and IKKβS176,180E.

24 hr after transfection (in the experiments depicted under Panels C and D), cycloheximide was added for the indicated times, and cells were lysed, resolved via SDS-PAGE, and proteins visualized using anti-FLAG, anti-KPC1 or anti-actin. Processing and degradation were assessed as described under FIG. 2C.

Chx denotes cycloheximide. Actin was used to ascertain equal protein loading.

Figure 2E:
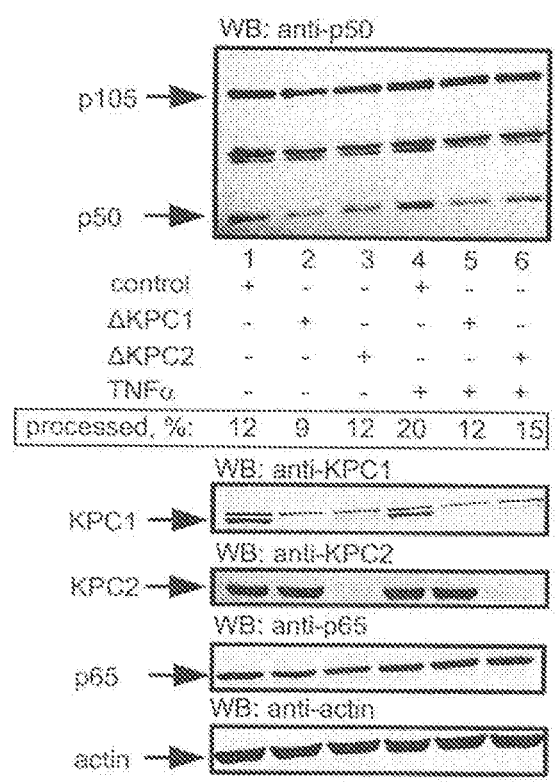

FIG. 2E are western blots showing that deletion of KPC1 or KPC2 genes inhibits basal and TNFα-induced processing of endogenous p105. Lysates were prepared from HAP1 control or HAP1 cells knocked out for the genes coding for KPC1 or KPC2. The lysates were resolved via SDS-PAGE, and proteins were visualized using anti-NF-κB1, -KPC1, -KPC2, -p65, or -actin. The amount of p105 processed was calculated as the ratio between the generated p50 and the sum of p50+p105, multiplied by 100%.

Figure 2F:
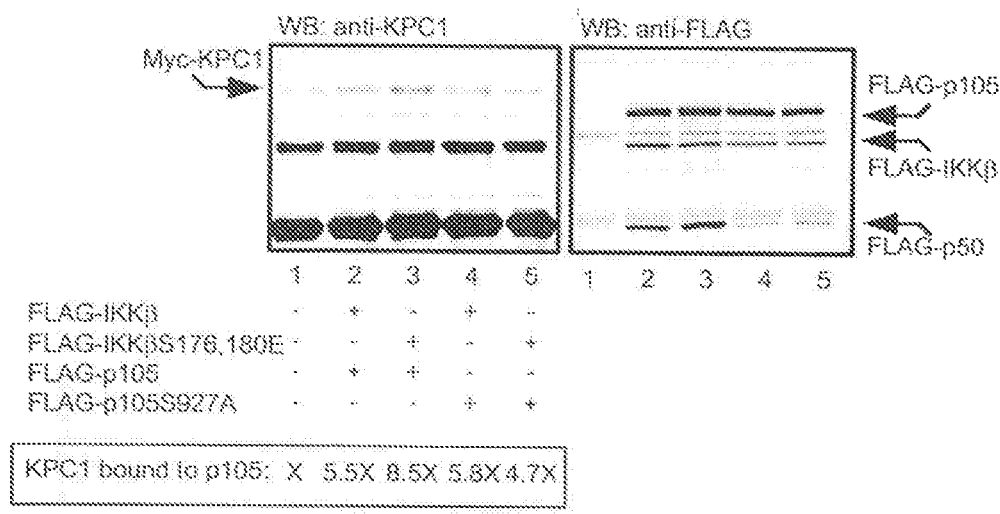

FIG. 2F are western blots showing that the interaction between p105 and KPC1 increases following signaling. HEK293 cells were transfected with cDNAs coding for FLAG-p105 (lanes 2 and 3) or FLAG-p105S927A (lanes 4 and 5) along with Myc-KPC1 (lanes 1-5) and FLAG-IKKβ (lanes 2 and 4) or FLAG-IKKβS176,180E (lanes 3 and 5). FLAG-p105 and FLAG-p105S927A were immunoprecipitated from the cell lysate using immobilized anti-FLAG (lanes 1-5), and the bound KPC1 was visualized with anti-KPC1 (Fi). Immunoprecipitated p105s were visualized using anti-FLAG (Fii).

Figure 2G:
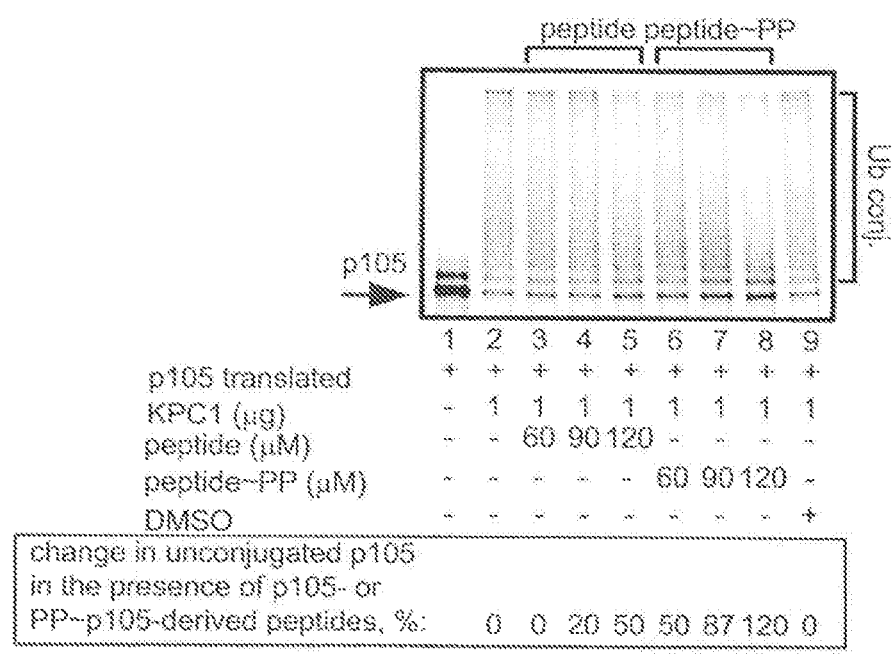

FIG. 2G is a western blot showing that phosphorylated peptide corresponding to the signaled sequence in p105 inhibits its ubiquitination. In vitro translated and 35S-labeled p105 was ubiquitinated by purified KPC1-FLAG-TEV-6×HIS (lanes 2-9) in a reconstituted cell free system in the presence of a phosphorylated peptide derived from the signaled sequence of p105 (lanes 6-8), or in the presence of its non-phosphorylated counterpart (lanes 3-5). Presented is the change (in %) of unconjugated p105 remained following addition of increasing concentrations of the peptides (compared to a system to which a peptide was not added; lane 2).

Figure 2H:
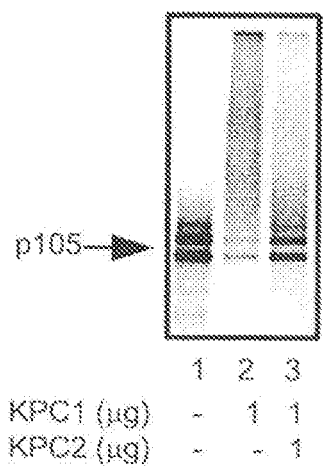

FIG. 2H is a western blot showing that KPC2 attenuates ubiquitination of p105 by KPC1. Ubiquitination of in vitro translated and 35S-labeled p105 by purified KPC1-FLAG-TEV-6×HIS in the presence or absence of HIS-KPC2 was carried out in a cell free reconstituted system.

Figure 2I:
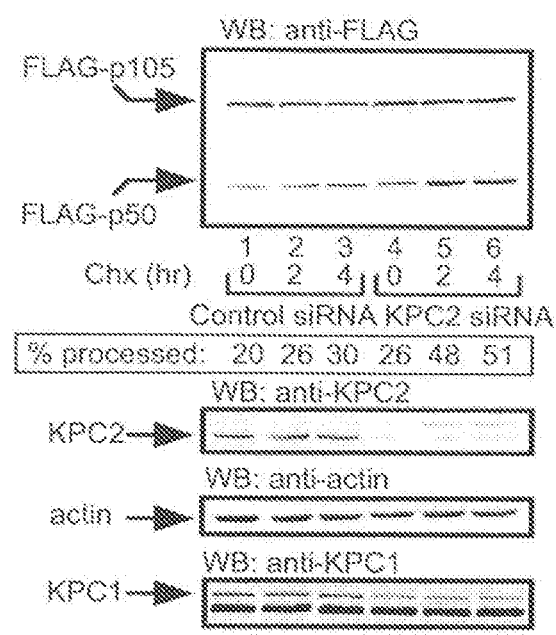

FIG. 2I are western blots showing that KPC2 attenuates processing of p105 in cells. HEK293 cells were transfected with control siRNA (lanes 1-3) or siRNA to silence KPC2 (lanes 4-6). After 24 hr, cells were transfected with cDNAs coding for FLAG-p105 and generation of p50 was monitored 24 hr later. Processing of p105 was calculated as described under 2C.

Figure 2J:
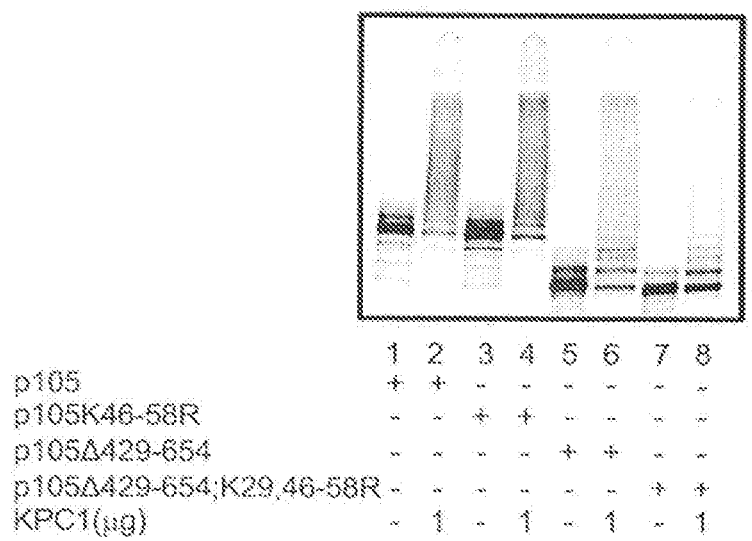

FIG. 2J is a western blot showing that KPC1 modifies lysine residues in the C-terminal segment of p105. In vitro-translated and 35S-labeled WT and the indicated p105 mutants were subjected to ubiquitination by purified KPC1-FLAG-TEV-6×HIS in a reconstituted cell free system.

See also FIGS. 8 A-G and 9 A-D.

FIG. 3 A-F demonstrate the KPC1-dependent ubiquitination and processing of p105 require the ARs of p105.

Figure 3A:
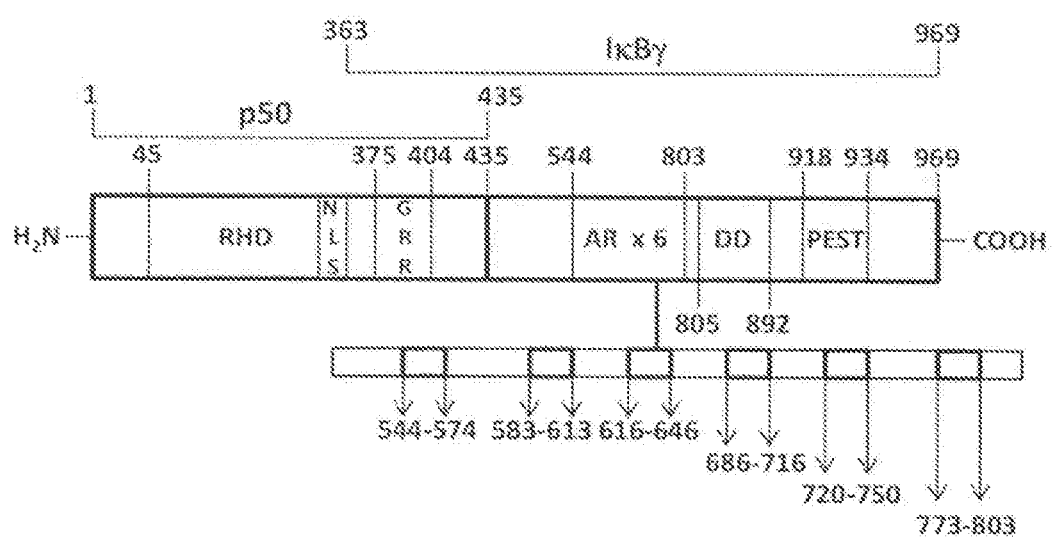

FIG. 3A is a schematic representation of p105 domains. Numbers denote the respective residue along the protein sequence. RHD, NLS, GRR, and AR denote Rel Homology Domain, Nuclear Localization Signal, Glycine Rich Repeat, and Ankyrin Repeats (all six of them are marked), respectively.

Figure 3B:
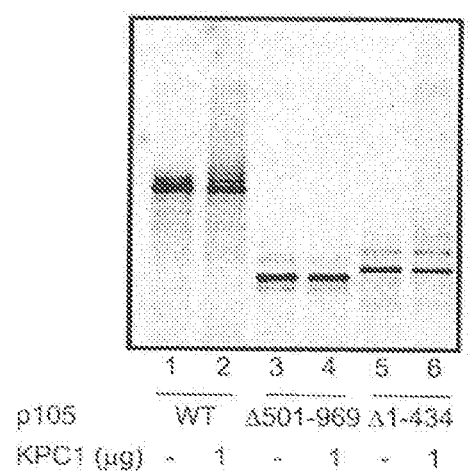

FIG. 3B is a western blot showing the ARs-containing C-terminal half of p105 is ubiquitinated by KPC1. In vitro-translated and 35S-labeled p105, p105Δ501-969 or p105Δ1-434 were subjected to ubiquitination by purified KPC1-FLAG-TEV-6×HIS in a reconstituted cell free system.

Figure 3C:
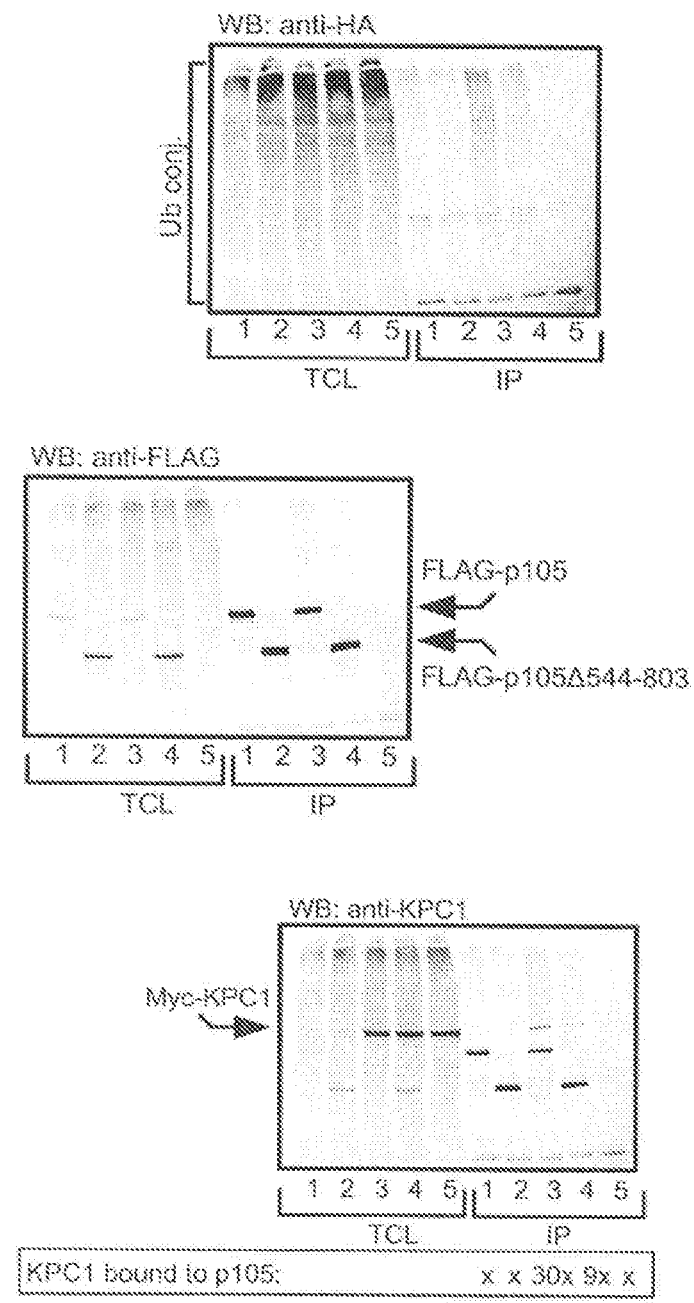

FIG. 3C are western blots showing the ARs of p105 are essential for binding of KPC1 and for its ubiquitination by the ligase in cells. HEK293 cells that were transfected with siRNA to silence KPC1 (lanes 1 and 2) or with control siRNA (lanes 3-5), were also transfected with cDNAs coding for FLAG-p105 (lanes 1 and 3), p105Δ544-803 (lanes 2 and 4), HA-Ub (lanes 1-5), and Myc-KPC1 (lanes 3-5). The different FLAG-p105 species and their conjugates were immunoprecipitated from the cell lysates by immobilized anti-FLAG (IP; lanes 1-5).

Figure 3D:
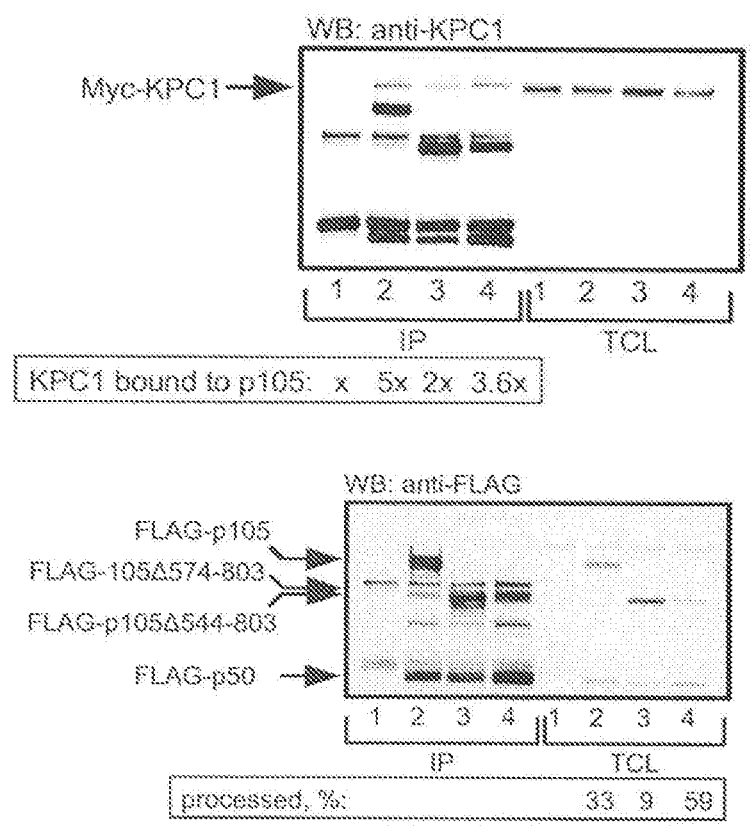

FIG. 3D are western blots showing that KPC1 interacts with a single AR in p105. HEK293 cells were transfected with cDNAs coding for FLAG-p105 (lane 2), FLAG-p105Δ544-803 (lane 3), or FLAG-p105Δ574-803 (lane 4), along with Myc-KPC1 (lanes 1-4). The different FLAG-p105 species were immunoprecipitated from the cell lysates using immobilized anti-FLAG (IP; lanes 1-4).

Figure 3E:
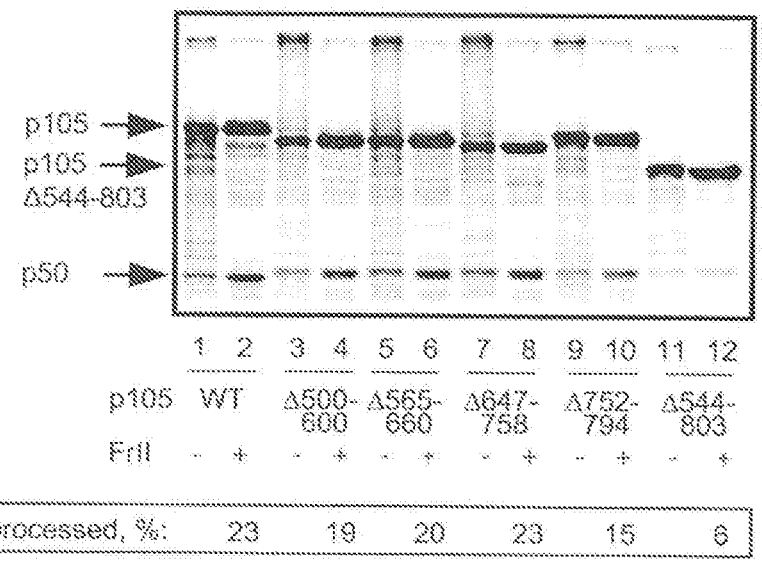

FIG. 3E is an autoradiography image showing that p105 that lacks its ARs is processed less efficiently in a cell free system. The different 35S-labeled p105 species were processed in a cell free reconstituted system in the presence or absence of Fraction II as indicated.

Figure 3F:
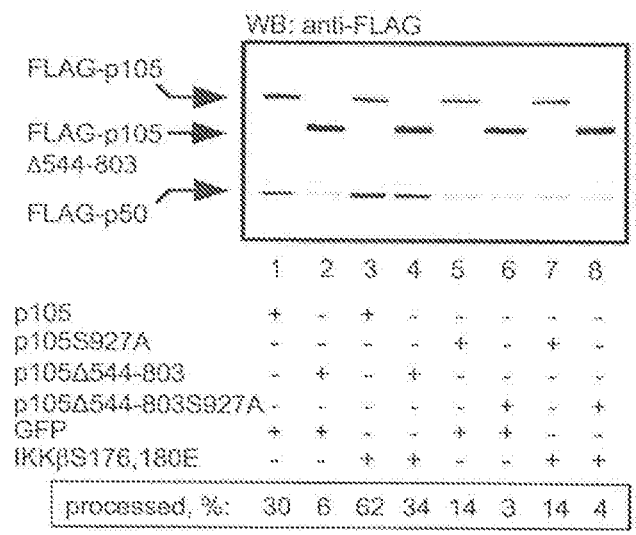

FIG. 3F is a western blot showing that deletion of the ARs of p105 affects both its basal and signal-induced processing. HEK293 cells were transfected with cDNAs coding for FLAG-p105, FLAG-p105Δ544-803, FLAG-p105S927A or FLAG-p105S927AΔ544-803 along with either GFP or IKKβ as indicated.

In FIGS. 3C, 3D and 3F, proteins were resolved via SDS-PAGE, blotted onto nitrocellulose membrane, and p105 and p50 were detected using anti-FLAG, KPC1 was detected using anti-KPC1, and Ub conjugates were detected using anti-HA. 10% of the total cell lysates (TCL) were analyzed for the expression of proteins. The SDS-PAGE-resolved labeled proteins in the experiments shown in panels B and E, were visualized using PhosphorImaging. Processing was assessed as described under FIG. 2E.

See also FIGS. 10 A-C.

FIG. 4 A-D demonstrate that KPC1 and p50 suppress anchorage-independent growth of cells.

Suppression of colony formation by overexpressed KPC1 or p50 in MDA-MB 231 (FIG. 4A upper panel), U2OS (FIG. 4B upper panel), and U87-MG (FIGS. 4C and D upper panels) cells. Cells were stably transfected with V0, or with cDNAs that code for Myc-KPC1, Myc-KPC1I1256A or FLAG-p50, or with cDNA coding for Myc-KPC1 along with control shRNA or shRNA to silence p105, as indicated, and were seeded on soft agar plates. After 3 weeks, the colonies were stained with 0.05% crystal violet. Data derived from 5 experiments (+/−SEM) are presented graphically. Expression of KPC1, KPC1I1256A, p50 and p105 is shown in the western blots of the lower panels of each of FIGS. 4A, 4B, 4C and 4D.

Figure 11:
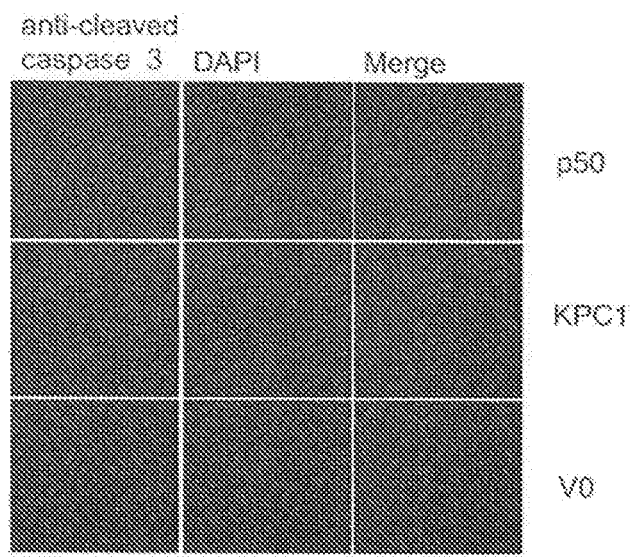

See also FIG. 11.

FIG. 5 A-E demonstrate that KPC1-mediated excessive generation of p50 inhibits tumor growth.

Figure 5A:
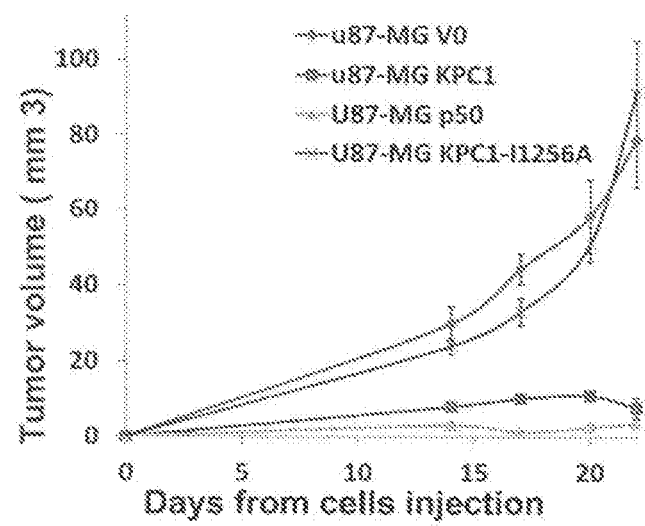
Figure 5A:
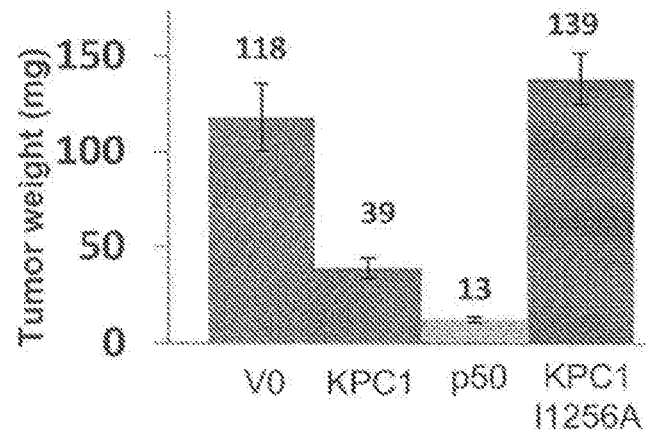
Figure 5B:
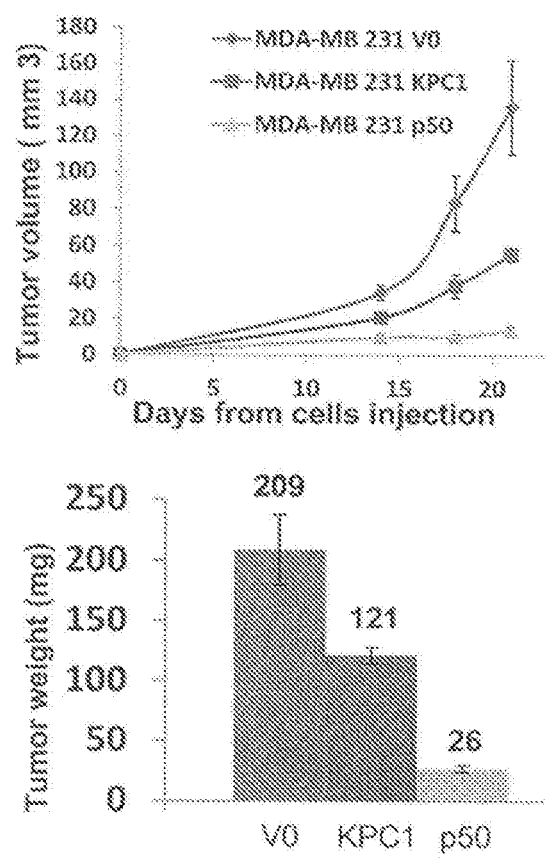
Figure 5C:
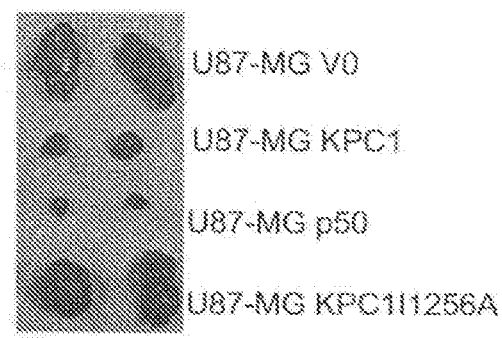

FIG. 5A-E shows growth rates and weights of tumor xenografts grown in mice, and derived from U87-MG (FIG. 5A) and MDA-MB 231 (FIG. 5B) cells expressing V0, Myc-KPC1, and FLAG-p50. Data represent the mean of 7 xenografts+/−SEM. FIG. 5C shows a photograph of tumors derived from U87-MG cells 3 weeks after inoculation.

Figure 5D:
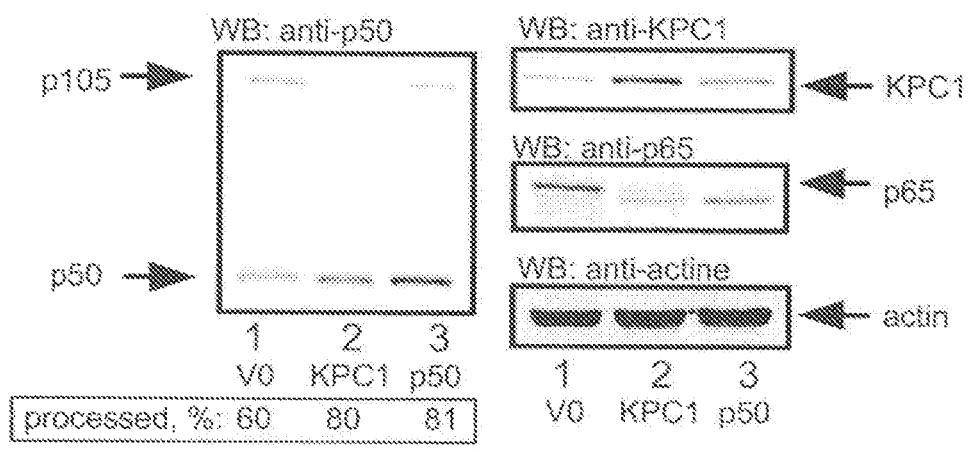

FIG. 5D shows enhanced generation of p50 and disappearance of p65 in tumors that overexpress KPC1. Proteins were resolved via SDS-PAGE, blotted onto nitrocellulose membrane, and detected using the appropriate antibodies. Processing was assessed as described under FIG. 2E.

Figure 5E:
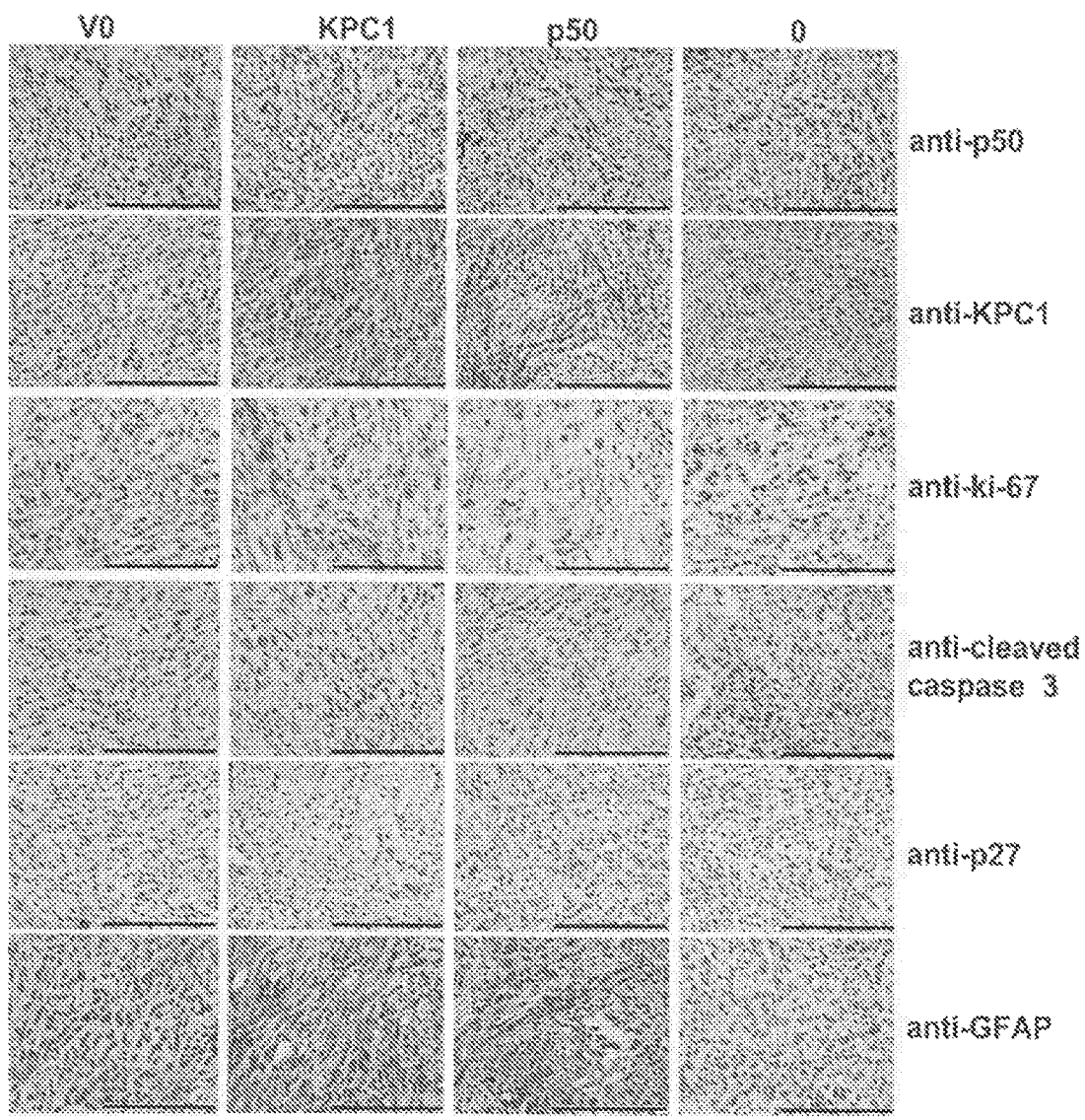

FIG. 5E shows photographs of immunohistochemical staining of p50, KPC1, ki-67, cleaved caspase 3, p27 and GFAP in xenografts of U87-MG cells stably expressing V0, Myc-KPC1, FLAG-p50, or KPC1I1256A.

All scale bars, 100 m. Tumors were grown in mice and stained as described under Experimental Procedures.

See also FIGS. 12 A and B.

FIG. 6 A-D show RNA analysis of glioblastoma xenografts expressing KPC1 and p50.

Figure 6A:
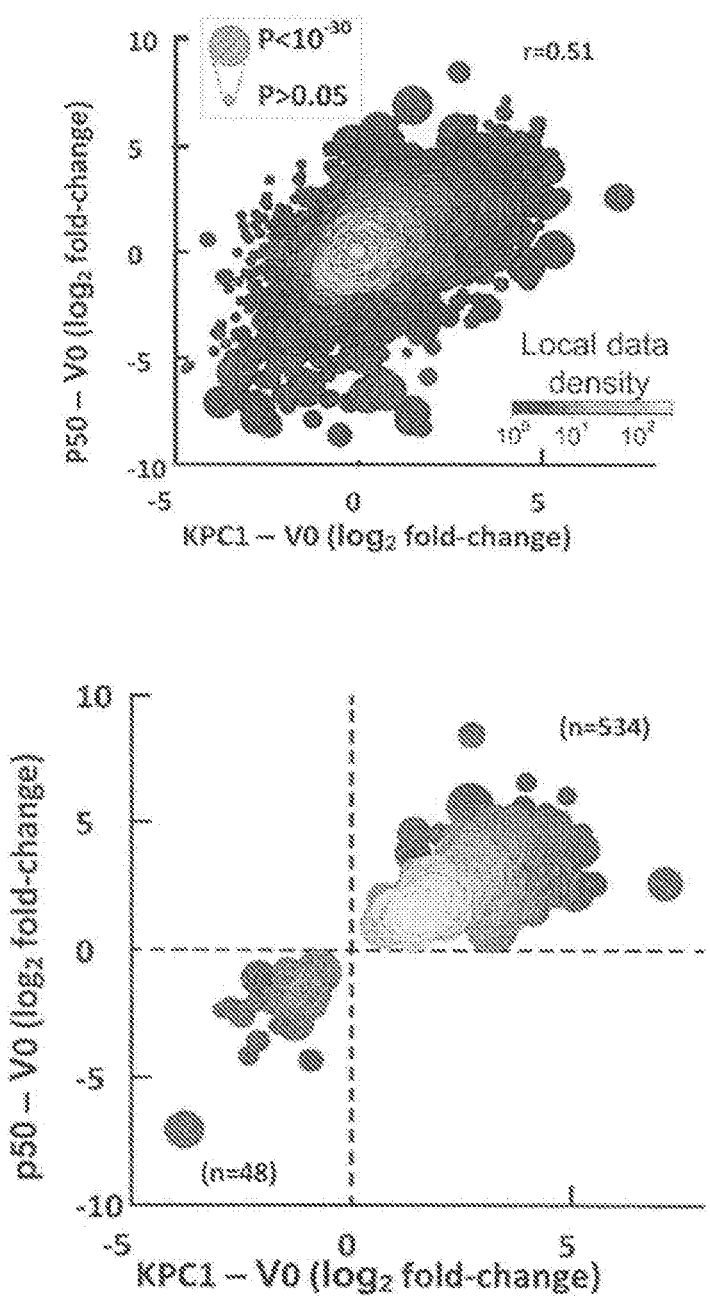
Figure 6B:
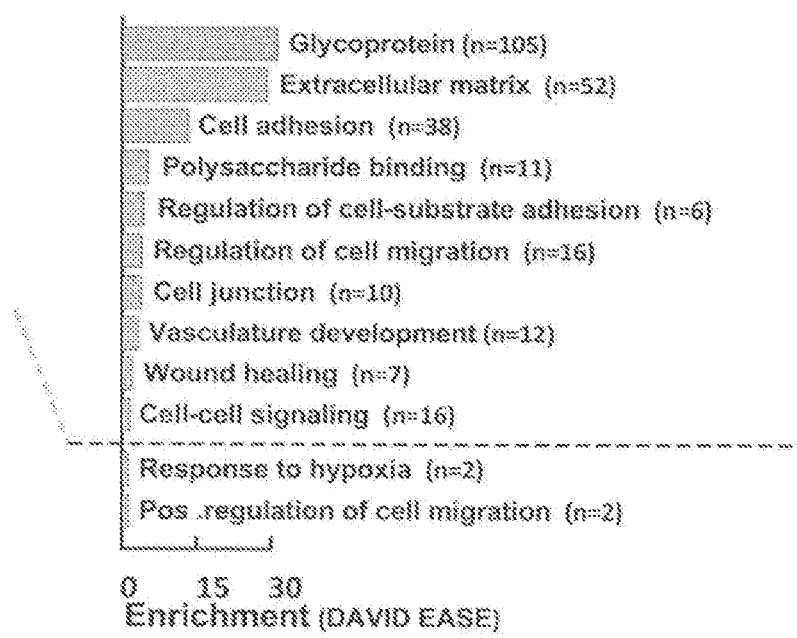

FIG. 6A upper graph shows the gene expression pattern as revealed by RNASeq of U87-MG xenografts overexpressing either KPC1 or p50. Shown is log 2-transformed fold-change in transcripts abundance against V0 control; dot size relates to the geometric mean significance over all experiments. FIG. 6A lower graph shows consistent down- and up-regulated genes in the xenografts. Dot sizes are as in in the upper graph. FIG. 6B shows selected annotation clusters most enriched for either up- or down-regulated genes (above or below dashed line, respectively).

Figure 6C:
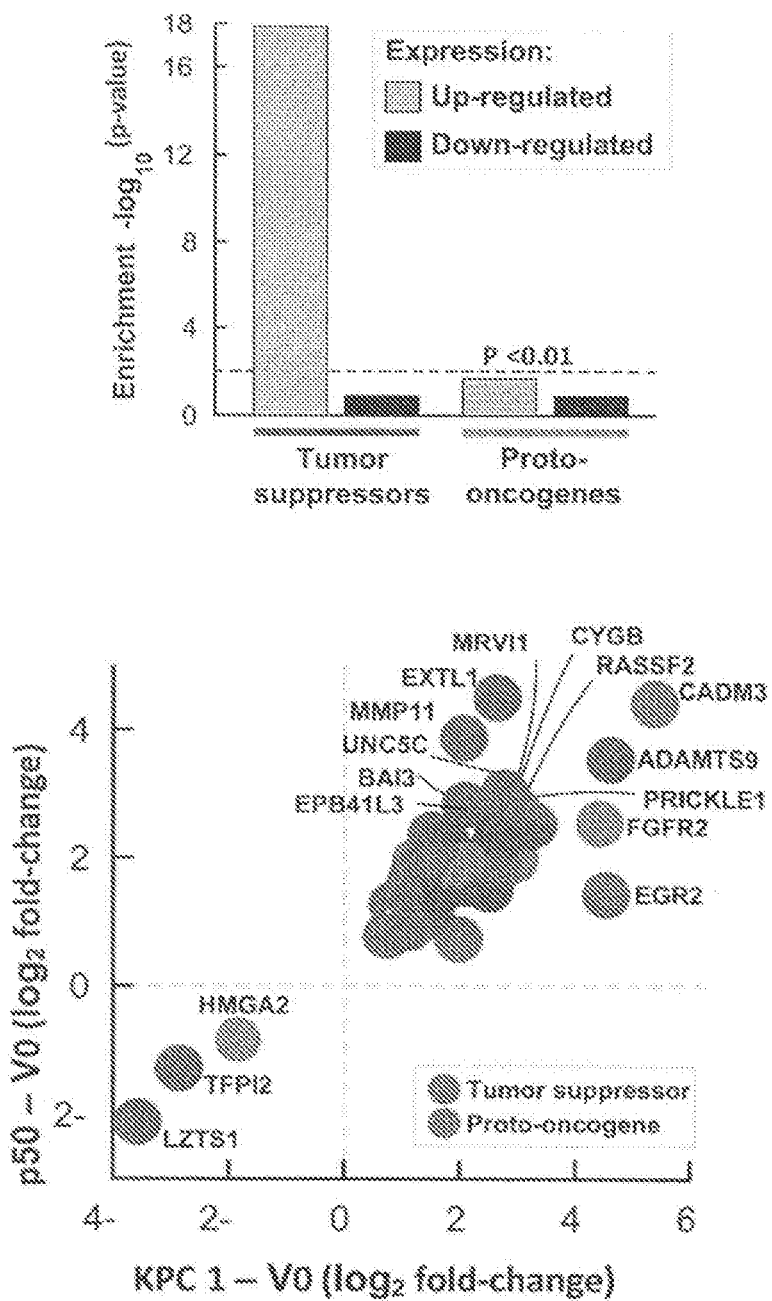

FIG. 6C shows enrichment analysis of consistently up- and down-regulated transcripts for tumor suppressors and proto oncogenes annotations (upper graph). FIG. 6C lower graph shows expression differences for all tumor suppressors (blue) and proto oncogenes (red) from the upper graph. Gene names of the strongest differentially regulated cancer-related genes are shown.

Figure 6D:
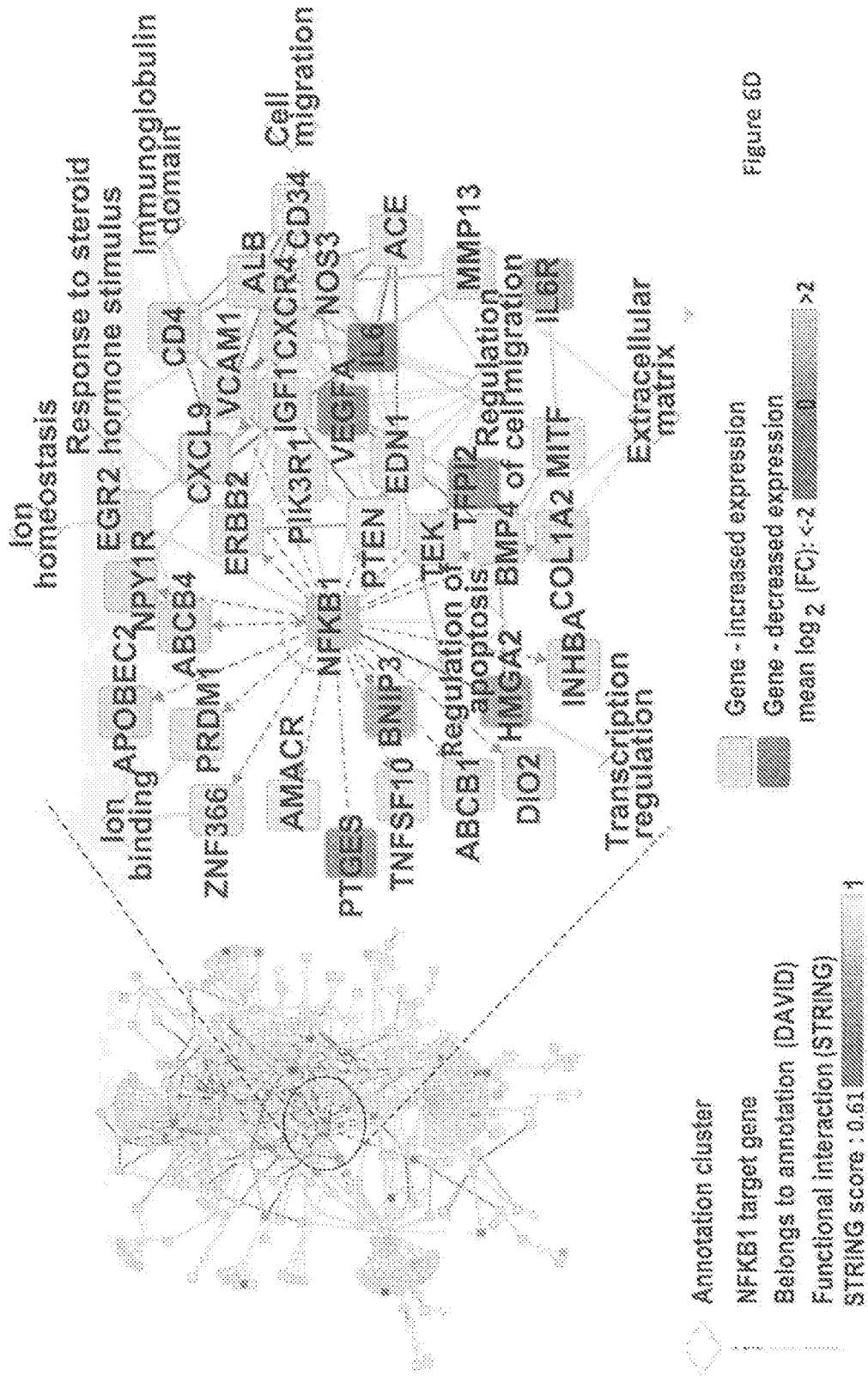

FIG. 6D shows integrated analysis of functional annotation clusters and known functional and physical protein-protein interactions among all consistently up- and down-regulated genes (green and red, respectively). NF-κB is shown in blue, and a close-up of the core interaction network surrounding NF-κB (inset) is displayed.

See also FIGS. 12 A and B.

FIG. 7 A-C shows the correlation between the expression of KPC1 and p50 in tumoral and normal human tissues.

Figure 7A:
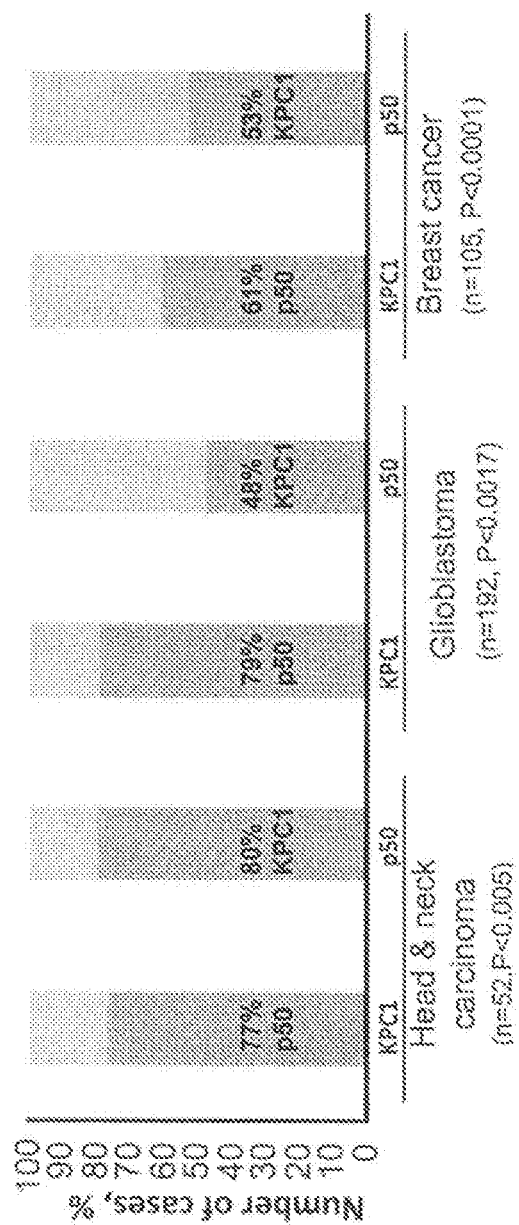
Figure 7B:
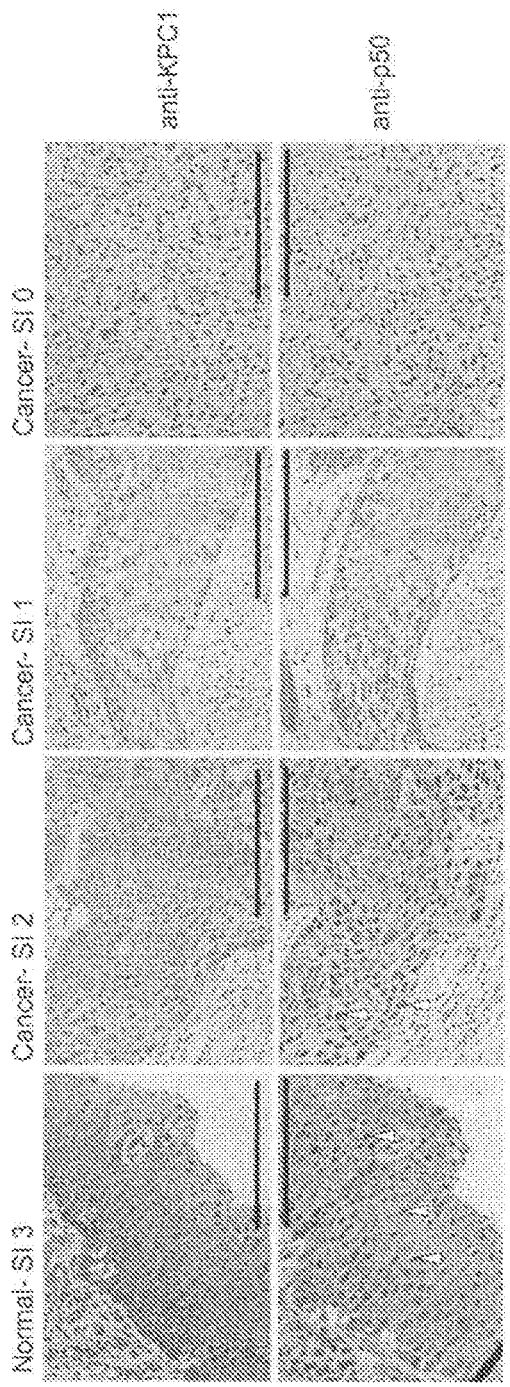

FIG. 7A shows the correlation between expression of KPC1 and p50 in tumors. Immunohistochemistry of KPC1 and p50 in serial sections from SCCHN, and glioblastoma and breast cancer tissue arrays. P denotes p-value. Analyses were carried out as described under Experimental Procedures. FIG. 7B is a representative immunostaining photograph of SCCHN sections with anti-KPC1 or anti-p50. SI denotes staining intensity from 3 (strong positive) to 0 (negative). Arrowheads point to nuclear staining. All scale bars, 100 μm.

FIG. 7C shows the statistical analysis of p50 and KPC1 staining in normal and cancerous head and neck, glial and breast tissues. "Average of KPC1 SI" represents mean of sample staining (number of samples is indicated under "Sample size"). "KPC1 stained, %" and "nuclear p50, %" represent percent of samples stained for KPC1 or nuclear p50. P denotes p-value. P-value reflects the significance of difference between staining of normal and cancer tissue. SI denotes staining intensity. N.S. denotes non-significant.

Figure 13A:
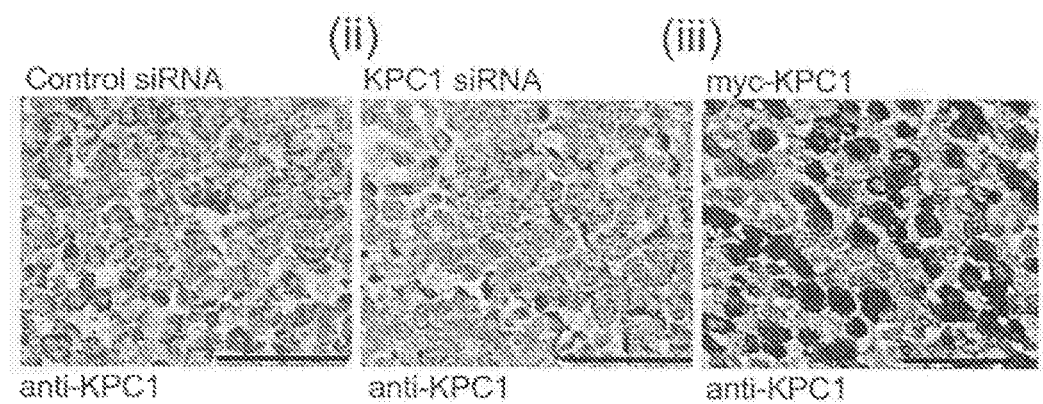
Figure 13B:
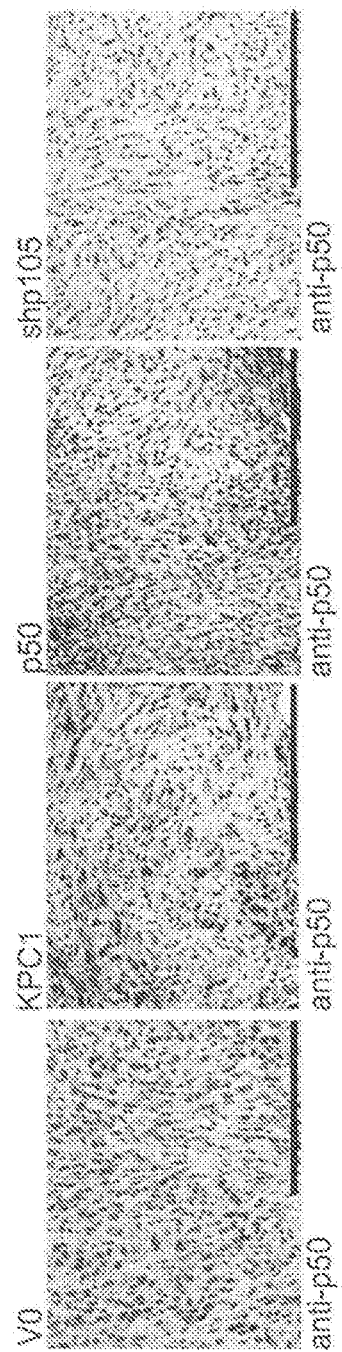
Figure 13C:
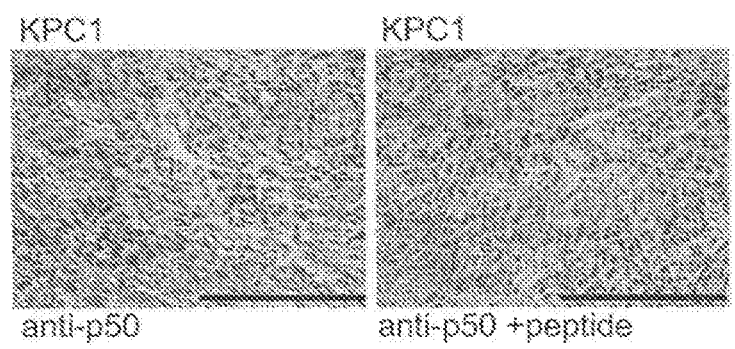

See also FIGS. 13 A, B and C.

FIG. 8 shows that p105 is a substrate of KPC1 and KPC2 ligase complex, related to FIG. 2A-J.

Figure 8A:
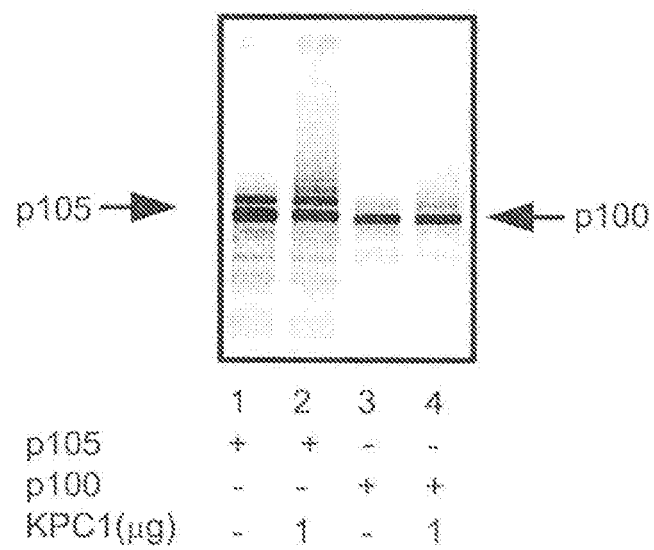

FIG. 8A is an autoradiography image showing ubiquitination of in vitro translated and 35S-labeled p105 and p100 by purified KPC1-FLAG-TEV-6×HIS in a reconstituted cell free system.

Figure 8B:
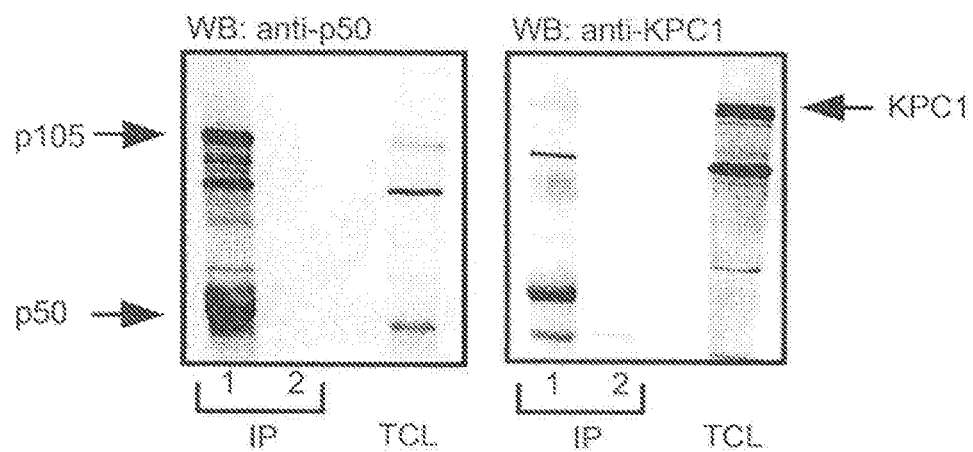

FIG. 8B is a western blot showing co-immunoprecipitation of endogenous p105 and KPC1. Endogenous p105 was immunoprecipitated from HeLa cell lysate using anti-p50 (lane 1) or Protein G-immobilized beads (lane 2). Proteins were resolved via SDS-PAGE, blotted onto nitrocellulose membrane, and p105 and p50 were detected using anti-p50 (Panel i), and KPC1 was detected using anti-KPC1 (Panel ii). An aliquot (10%) of the total cell lysate (TCL) was analyzed for expression of the proteins.

Figure 8C:
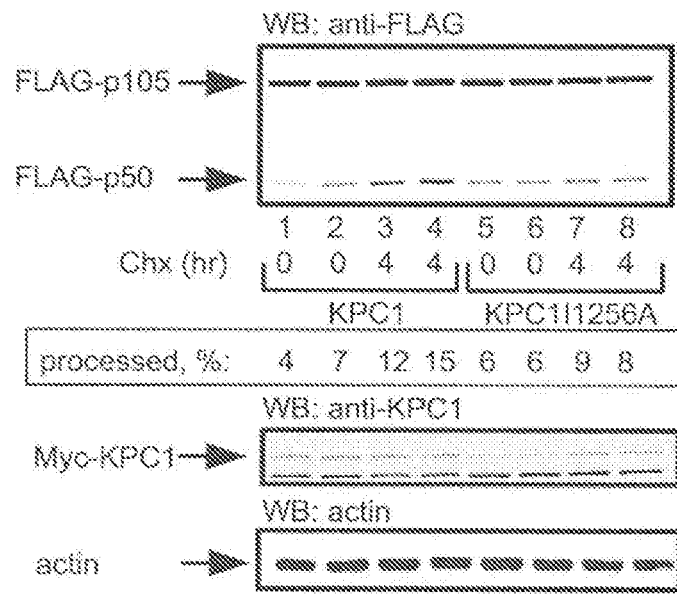

FIG. 8C is a western blot showing that cells expressing KPC1 RING domain-mutant process p105 less efficiently compared to those expressing WT KPC1. HEK293 cells were transfected with cDNAs coding for FLAG-p105 along with Myc-KPC1 or Myc-KPC1I1256A. 24 hr after transfection, cycloheximide was added for the indicated times, and cells were lysed, resolved via SDS-PAGE, and proteins visualized using anti-FLAG, anti-KPC1 or anti-actin as described under Experimental Procedures. Chx denotes cycloheximide. Actin was used to ascertain equal protein loading. Processing was assessed as described under FIG. 2E.

Figure 8D:
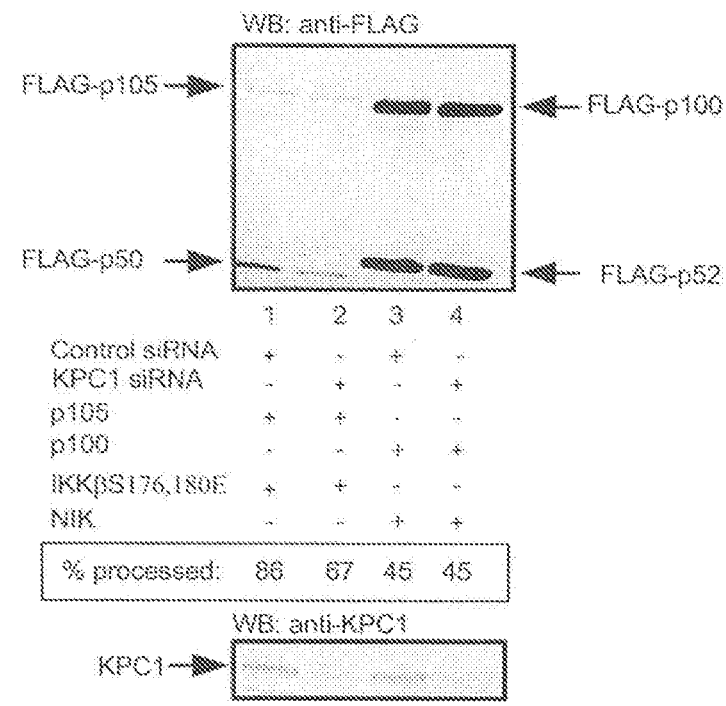

FIG. 8D is a western blot showing that silencing of KPC1 inhibits specifically signal-induced processing of p105 but not of p100. HEK293 cells were transfected with control siRNA (lanes 1, 3) or siRNA that targets KPC1 (lanes 2, 4). After 24 hr, cells were transfected with cDNAs coding for FLAG-p105, FLAG-p100, IKKβS176,180E or NIK, as indicated. After additional 24 hr, cells were lysed, resolved via SDS-PAGE, and proteins were visualized using anti-FLAG and anti-KPC1 as described under Experimental Procedures. Processing was assessed as described under FIG. 2E.

Figure 8E:
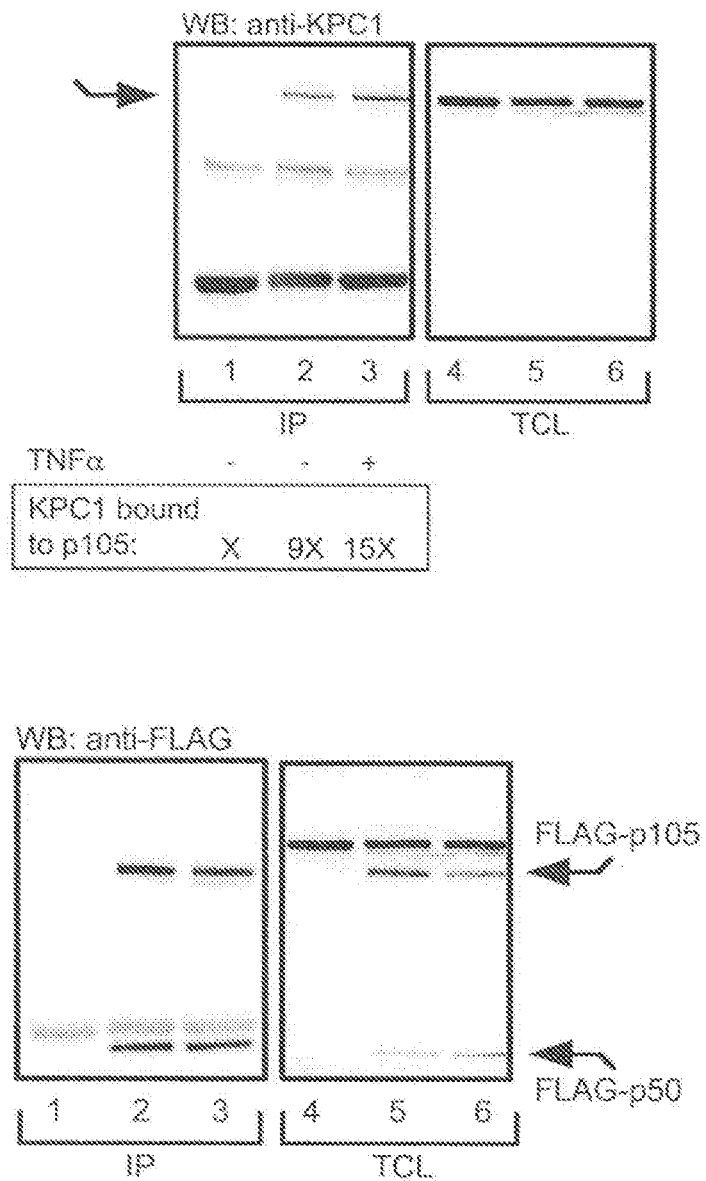

FIG. 8E are western blots showing that the interaction between p105 and KPC1 is stimulated by TNFα. HeLa cells were transfected with cDNAs coding for FLAG-p105 (lanes 2 and 3) along with Myc-KPC1 (lanes 1-3). After 24 hr, cells were treated with TNFα (50 ng/ml) for 30 min (lane 3). FLAG-p105 was immunoprecipitated from the cell lysate using immobilized anti-FLAG (IP; lanes 1-3), and the bound KPC1 was visualized using anti-KPC1 (upper western blot; IP). p105 was visualized using anti-FLAG (lower western blot; IP). 10% of the total cell lysates (TCL; lanes 4-6) were analyzed for the expression of Myc-KPC1 or FLAG-p105 using anti-KPC1 (FIG. 8E upper panel) or anti-FLAG (FIG. 8E lower panel), respectively.

Figure 8F:
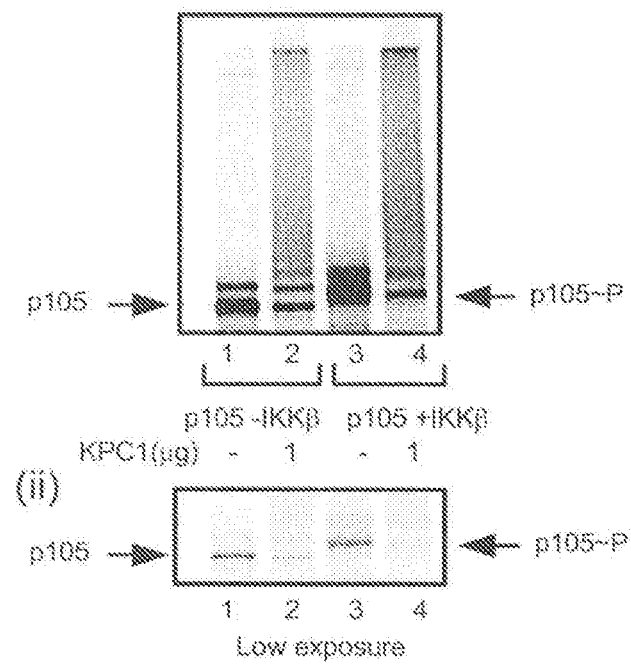

FIG. 8F is an autoradiography image showing that phosphorylation of p105 enhances its ubiquitination by KPC1. FIG. 8F upper panel shows ubiquitination of in vitro translated and 35S-labeled p105 or P-p105 (phosphorylated by IKKβS176,180E; 1 μg added 20 min prior to the addition of the ligase; ATP, creatine phosphate and creatine phosphokinase were present in concentration of 0.1 mM, 10 mM, and 0.5 μg, respectively) was carried out by KPC1-FLAG-TEV-6×HIS in a reconstituted cell free system. FIG. 8F lower panel shows the non-phosphorylated and phosphorylated forms of p105.

Figure 8G:
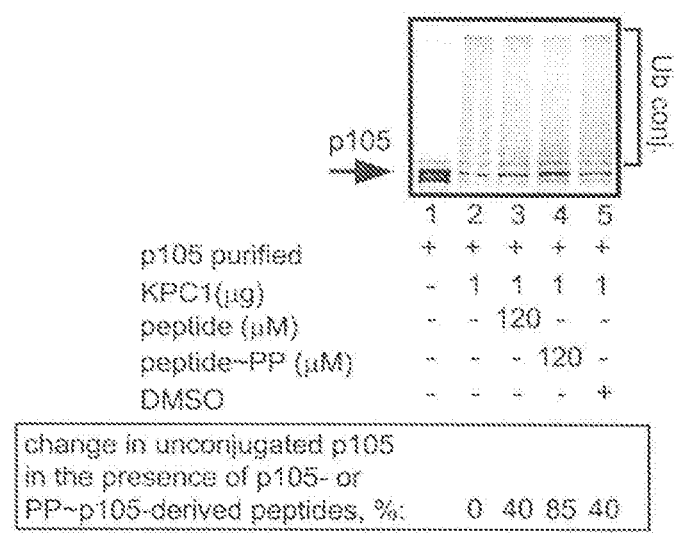

FIG. 8G is an autoradiography image showing that phosphorylated peptide corresponding to the signaled sequence in p105 inhibits ubiquitination of purified p105. In vitro translated and 35S-labeled FLAG-p105 (immunoprecipitated by FLAG-beads, washed and released by the FLAG peptide; 100 μg/ml) was ubiquitinated by purified KPC1-FLAG-TEV-6×HIS (lanes 2-5) in a reconstituted cell free system in the presence of non-phosphorylated (lane 3) or phosphorylated (lane 4) peptides derived from the signaled sequence of p105. Presented is the change (in %) of free unconjugated p105 remained following addition of the peptides (compared to a system to which a peptide was not added; lane 2).

FIG. 9 A-D demonstrate that KPC2 attenuates KPC1-mediated ubiquitination of p105 that occurs on lysine residues in the c-terminal segment of the precursor, related to FIG. 2A-J.

Figure 9A:
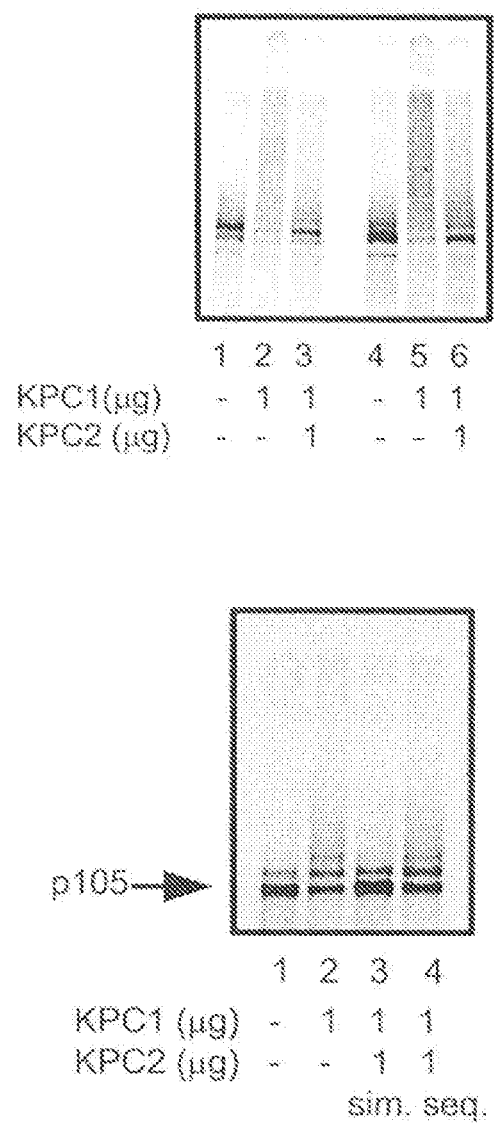

FIG. 9A are autoradiography image showing that purified KPC1 ubiquitinates purified p105, a modification that is attenuated by purified KPC2 (lanes 1-3).

FIG. 9A upper autoradiography image shows 35S-labeled and in vitro translated FLAG-p105 that were immunoprecipitated using FLAG-beads. The beads were washed and the translated protein was released by FLAG peptide (1000 g/ml). Purified KPC1-FLAG-TEV-6×HIS and purified 6×HIS-KPC2 were added as indicated. Purified E1, UbcH5c, and ubiquitin, along with other necessary components were added as described under Experimental Procedures. A similar reaction was carried out with labeled p105 still present in the lysate in which it was translated (lanes 4-6). FIG. 9A lower autoradiography image shows that attenuation of p105 ubiquitination by KPC2 is not attributed to a KPC2 deubiquitinating activity. In vitro translated and 35S-labeled p105 was subjected to ubiquitination by KPC1-FLAG-TEV-6×HIS in a cell free system. The reactions were carried out in the absence or presence of KPC2 that was added along with (sim.—simultaneously) or following the addition of KPC1 (seq.—sequentially).

Figure 9B:
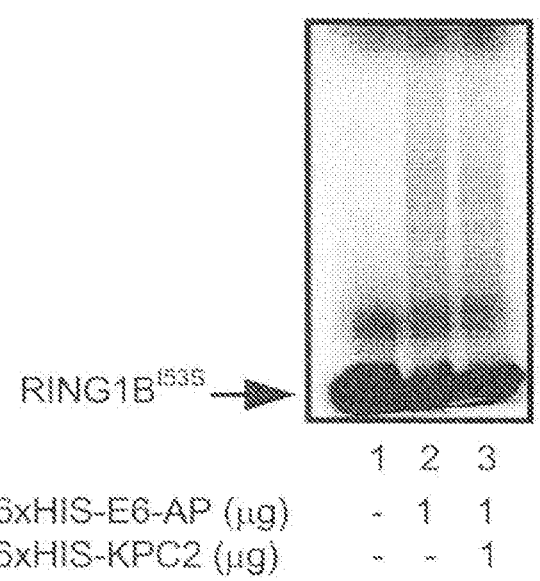

FIG. 9B is an autoradiography image showing ubiquitination of in vitro translated and 35S-labeled RING1BI53S by 6×HIS-E6-AP in the presence or absence of 6×HIS-KPC2 was carried out in a reconstituted cell free system.

Figure 9C:
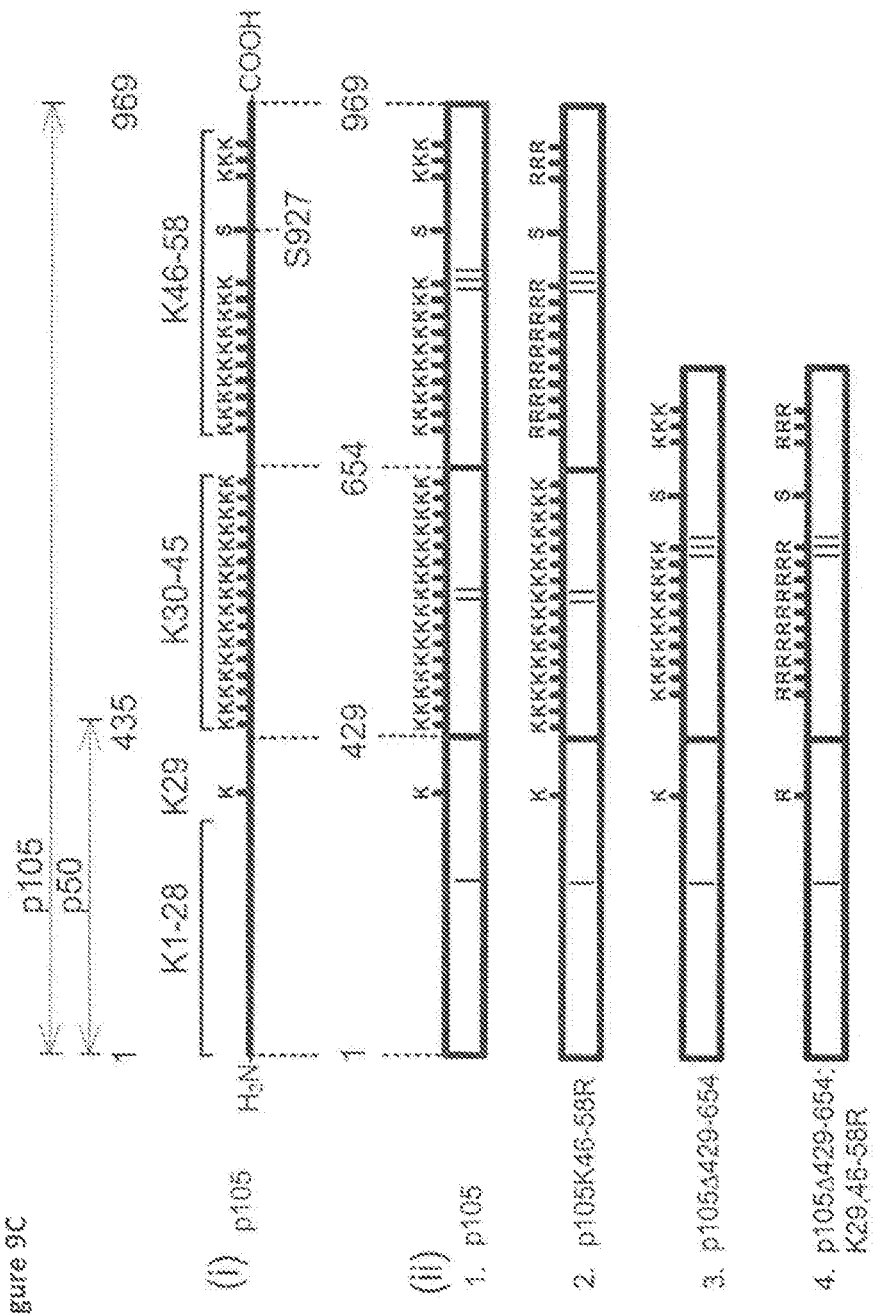

FIG. 9C is a schematic representation of lysine residues in p105, p105K46-58R, p105Δ429-654, and p105Δ429-654; K29,46-58R. Numbers denote the respective residue along the protein sequence, and numbers next to K denote the respective lysine residue (numbered from 1 to 58) along the protein sequence.

Figure 9D:
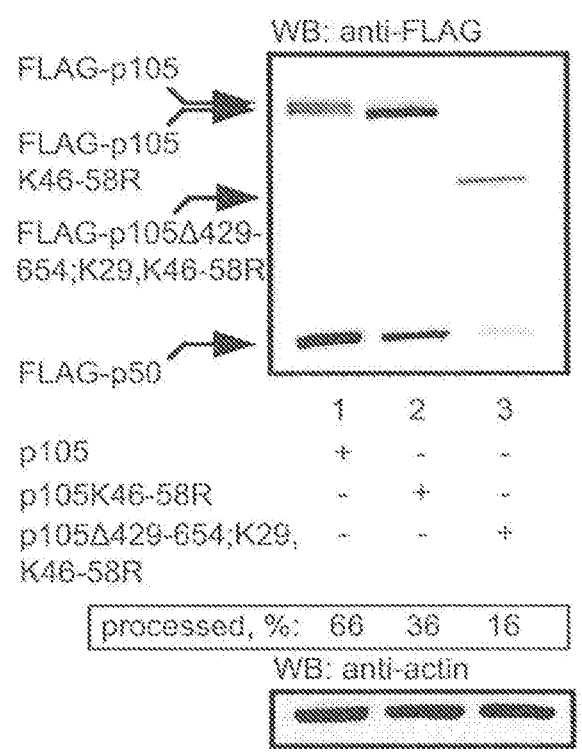

FIG. 9D is a western blot showing cellular processing of FLAG-p105 species mutated in the ubiquitination sites along the C-terminal segment. cDNAs coding for WT and the indicated p105 mutants were transfected to HEK293 cells. Following SDS-PAGE of cell lysates, p105 and processed p50 were detected using anti-FLAG. Processing was assessed as described under FIG. 2E.

Figure 10A:
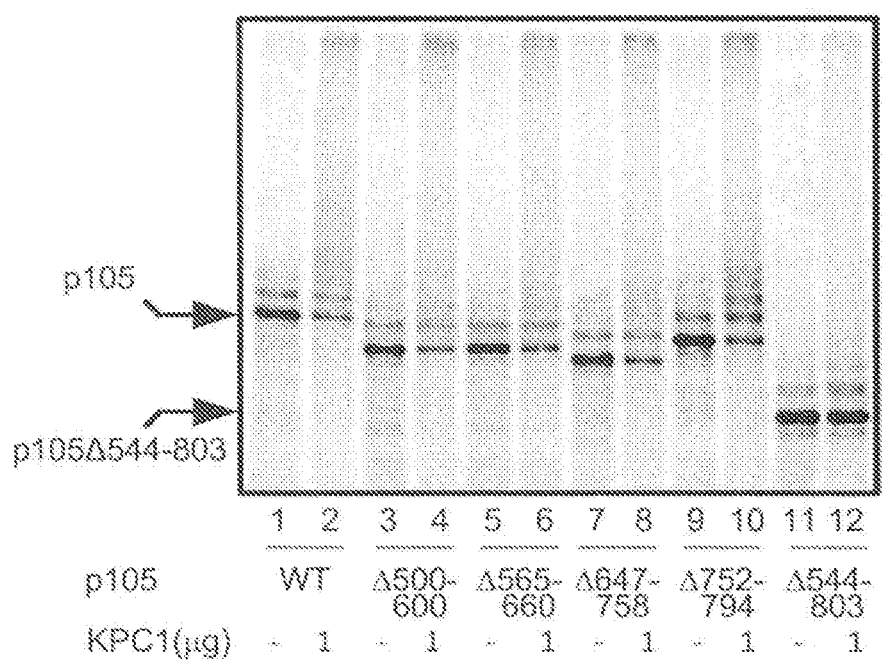
Figure 10B:
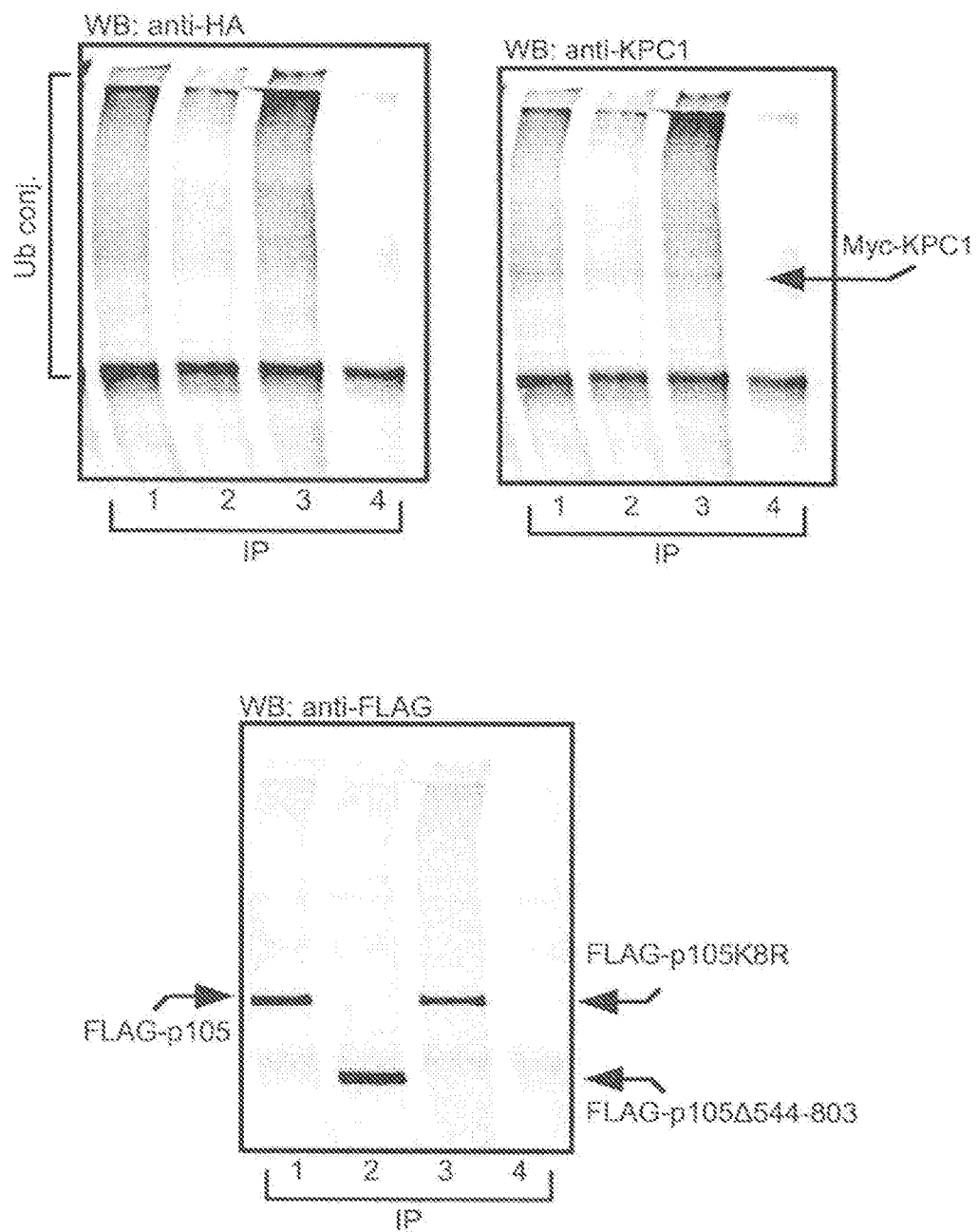
Figure 10C:
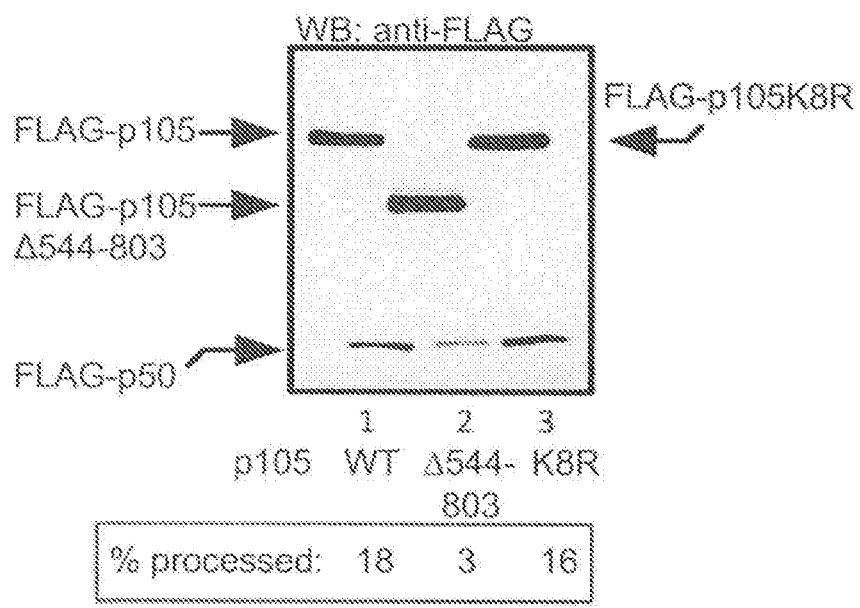

FIG. 10A-C demonstrates that the p105 ankyrin repeats are essential for its ubiquitination and processing, Related to FIG. 3A-F.

FIG. 10A is an autoradiography image showing that a single AR in p105 is dispensable for ubiquitination by KPC1 in a cell free system. The different deletion 35S-labeled p105 species were ubiquitinated in a cell free reconstituted system in the presence or absence of KPC1-FLAG-TEV-6×HIS as indicated. The SDS-PAGE-resolved labeled proteins were visualized as described under Experimental Procedures.

FIG. 10B are western blots showing that the internal lysines of the ARs are dispensable for ubiquitination of p105. HEK293 cells were transfected with cDNAs coding for FLAG-p105 (lane 1), FLAG-p105Δ544-803 (lane 2), or FLAG-p105K8R (lane 3; p105 in which all 8 lysines in the 6 ARs and in between them were substituted with arginines) along with Myc-KPC1 and HA-Ub (lanes 1-4). The different FLAG-p105 species were immunoprecipitated from cell lysates using immobilized anti-FLAG (IP; lanes 1-4), resolved via SDS-PAGE, and visualized using anti-HA (FIG. 10B upper left), anti-KPC1 (FIG. 10B upper right), or anti-FLAG (FIG. 10B lower).

FIG. 10C is a western blot showing that the internal lysines of the ARs are dispensable for processing of the molecule. HEK293 cells were transfected with cDNAs coding for FLAG-p105 (lane 1), FLAG-p105Δ544-803 (lane 2), or FLAG-p105K8R (lane 3). Proteins were resolved via SDS-PAGE, blotted onto nitrocellulose membrane, and p105 and p50 were detected using anti-FLAG. Processing was assessed as described under FIG. 2E.

FIG. 11 is a photograph showing the effect of overexpressed KPC1 and p50 on cleaved caspase 3 in cultured cells, Related to FIG. 4A-D. Anti-cleaved caspase 3 immunofluorescent staining of U87-MG cells stably overexpressing an empty vector (V0), Myc-KPC1, or FLAG-p50.

FIGS. 12 A and B demonstrate the analysis of U87-MG xenografts expressing V0, KPC1, or p50 for binding of NF-κB to its 'canonical' binding site, and for transcript levels of selected human genes, Related to FIGS. 5A-E and 6A-D.

Figure 12A:
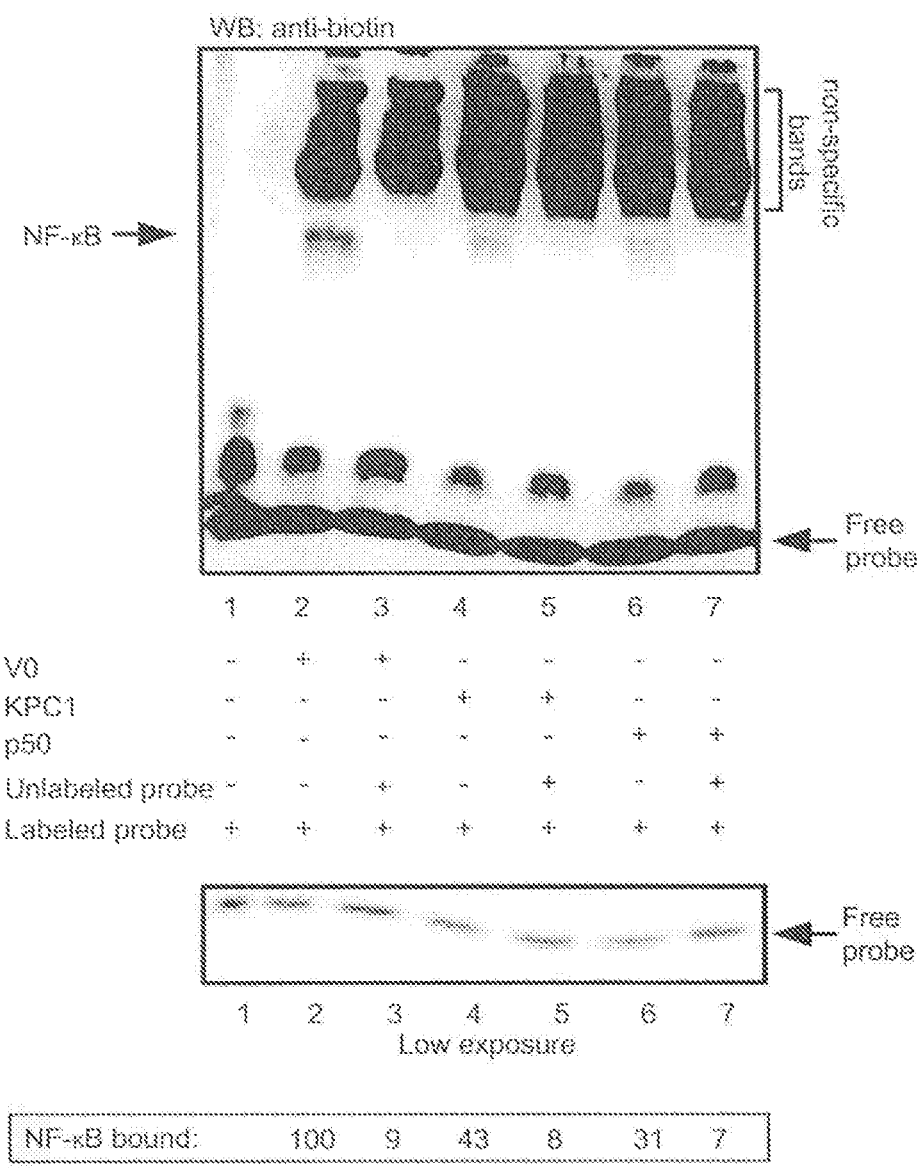

FIG. 12A are western blots. EMSA ElectroMobility Shift Assay was carried out as described under Experimental Procedures. Values represent bound NF-kB where 100 is the value measured in an extract derived from cells expressing an empty vector.

Figure 12B:
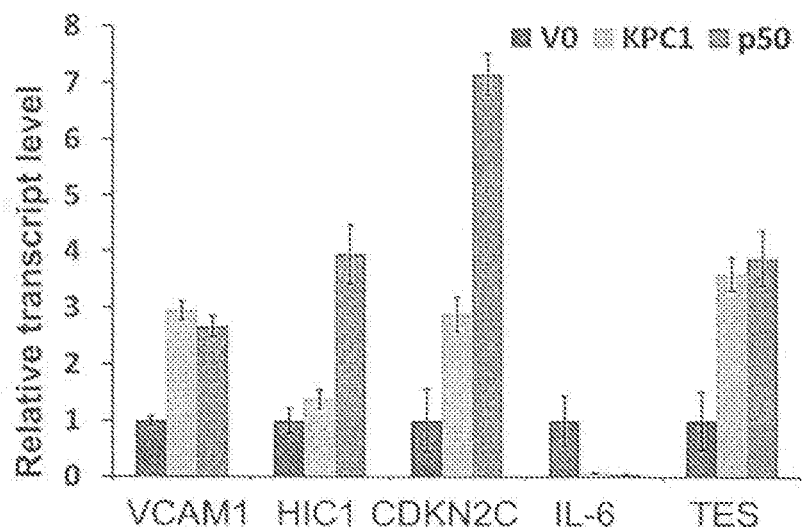

FIG. 12B is a graph showing the relative transcripts level of RNA isolated from U87-MG xenografts expressing V0, Myc-KPC1 or FLAG-p50. Expression of VCAM1, HIC1, CDKN2C, IL-6 and TES genes was analyzed using qRT-PCR as described under Experimental Procedures.

FIGS. 13 A, B and C are photographs showing that validation of the specificity of the antibodies to KPC1 and p50 used for Immunohistochemical staining of tumoral and normal human tissues, Related to FIG. 7A-C.

Validation of the specificity of the anti-KPC1 antibody. Immunohistochemistry of KPC1 in HEK293 cells that were transfected with control siRNA (left), siRNA to silence KPC1 (middle) or with Myc-KPC1 (right). All scale bars, 20 μm.

and (C) Validation of the specificity of the anti-p50 antibody. Upper panel: Immunohistochemistry of p50 in xenografts of U87-MG cells stably expressing V0, Myc-KPC1, FLAG-p50 or shRNA to p105. Lower panel: immunohistochemistry of p50 in xenografts of U87-MG cells stably expressing Myc-KPC1 in the presence or absence of a specific blocking peptide (10 μg/ml) to the anti-p50 antibody. All scale bars, 100 μm.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In an embodiment of the invention, NF-κB is a key transcriptional regulator involved in inflammation and cell proliferation, survival, and transformation. Several key steps in its activation are mediated by the ubiquitin (Ub) system. One uncharacterized step is limited proteasomal processing of the NF-κB1 precursor p105 to the p50 active subunit. In an embodiment of the invention, KPC1 as the Ub ligase (E3) that binds to the ankyrin repeats domain of p105, ubiquitinates it, and mediates its processing both under basal conditions and following signaling. In an embodiment of the invention, overexpression of KPC1 promotes inhibition of tumor growth mediated probably via excessive generation of p50. In an embodiment of the invention, excessive p50 down regulates p65, explaining the possible lack of the 'canonical', p50∩p65 tumor promoting NF-κB. Transcript analysis reveals increased expression of genes associated with tumor suppressive signals. Overall, in an embodiment of the invention, KPC1 regulation of NF-κB1 processing appears to constitute an important balancing step among the stimulatory and inhibitory activities of the transcription factor in cell growth control.

In an embodiment of the invention, KIP1 ubiquitination-promoting complex (KPC) was identified as the Ub ligase that is involved in both basal and signal-induced processing of p105. KPC is a heterodimer made of KPC1 (RNF123) and KPC2 (UBAC1). It was shown to degrade the cyclin-dependent kinase inhibitor p27KIP1 in the G1 phase of the cell cycle (Kamura et al., 2004). In an embodiment of the invention, KPC1 is a RING-finger protein that serves as the ligase. In an embodiment of the invention, KPC2 interacts with ubiquitinated proteins and with the proteasome via its two Ub-associated domains and a Ub-like domain, acting as a shuttle that promotes the degradation of p27KIP1. It was also shown to stabilize KPC1 (Hara et al., 2005).

The vast majority of substrates of the Ub proteasome system are completely degraded. One intriguing and exceptional case is that of the p105 precursor of NF-κB that can be either completely degraded or processed in a limited manner to yield the p50 active subunit of the transcription factor. The "decision-making" mechanism resulting in one of the two distinct processes has remained largely elusive. The βTrCP Ub ligase has been identified as the tagging enzyme involved in complete degradation of p105, whereas the ligase involved in processing has remained unknown. The KPC complex has been identified as the putative p105-processing ligase (FIGS. 1A-C, 2A-J and 3A-F).

Now that the two E3s involved in degradation and processing of p105 have been identified, it is still not known why ubiquitination by one enzyme results in a completely different fate of p105 than ubiquitination by the other, and what determines the timing of the two reactions. It is possible that the two ligases catalyze the formation of chains that differ in their anchoring sites, length and/or internal linkages. These in turn affect the recognition and mechanism of action of the 26S proteasome. As for timing, it can be that different physiological conditions and/or the degree of saturation of the ARs with bound p50s are involved in the "decision-making" process of whether the molecule will be processed or destroyed completely.

Studying the biological implications of manipulating KPC1 revealed that in one embodiment, suppresses anchorage-independent growth in a manner that is dependent on its ligase activity and the presence of p105. A corollary strong tumor suppressive effect was demonstrated in xenografts of human tumors (see in the Examples and FIGS. 4A-D, 5A-E and 6A-D). This effect is caused, in an embodiment of the invention, by a significant increase in an entire set of tumor suppressors. An important question relates to the transcriptional mechanism by which KPC1 and p50 exert their tumor suppressive effect. An obvious assumption is that the stoichiometric excess of p50 generated by KPC1 would generate mostly p50•p50 homodimers rather than the 'canonical' tumorigenic p50•p65 heterodimers. In line with this finding is also the observation that p65 level is decreased in KPC1— as well as in p50-overexpressing xenografts (FIG. 5D). It appears that each dimer of NF-κB family has unique and even opposing biological function(s), and regulates a distinct subset of downstream genes (Siggers, T., Chang, A. B., Teixeira, A., Wong, D., Williams, K. J., Ahmed, B., Ragoussis, J., Udalova, I. A., Smale, S. T., and Bulyk, M. L. (2012). Principles of dimer-specific gene regulation revealed by a comprehensive characterization of NF-kappaB family DNA binding. Nat. Immunol 13, 95-102). p50 homodimer is supposed to act as a transcriptional repressor because it does not contain a transactivation domain (May, M. J., and Ghosh, S. (1997). Rel/NF-kappa B and I kappa B proteins: an overview. Semin. Cancer Biol. 8, 63-73). However, studies in vitro have shown that p50 homodimer can interact with different transcriptional modulators, such as Bcl-3 (Fujita, T., Nolan, G. P., Liou, H. C., Scott, M. L., and Baltimore, D. (1993). The candidate proto-oncogene bcl-3 encodes a transcriptional coactivator that activates through NF-kappa B p50 homodimers. Genes Dev. 7, 1354-1363), p300 (Deng, W. G., and Wu, K. K. (2003). Regulation of inducible nitric oxide synthase expression by p300 and p50 acetylation. J. Immunol 171, 6581-6588) or HMGA1/2 (Perrella, M. A., Pellacani, A., Wiesel, P., Chin, M. T., Foster, L. C., Ibanez, M., Hsieh, C. M., Reeves, R., Yet, S. F., and Lee, M. E. (1999). High mobility group-I(Y) protein facilitates nuclear factor-kappaB binding and transactivation of the inducible nitric-oxide synthase promoter/enhancer. J. Biol. Chem. 274, 9045-9052) that are involved in chromatin remodeling. Disproportionate p50 may shift the composition of NF-κB dimers, resulting in overall tumor suppressive effect.

Indeed, following overexpression of KPC1 or p50, there is a decrease in the level of what is probably the 'canonical' tumorigenic NF-kB (p50•p65; FIG. 12A).

A strong correlation between the expression of KPC1 and that of p50 in human tumors has been found (FIGS. 7A and B). Moreover, a significant decrease in nuclear p50 and KPC1 staining intensity in tumors compared to non-malignant tissue was also found (FIG. 7C). This observation suggests that loss of nuclear p50 may trigger malignant transformation.

As shown in the Examples section, KPC1 promotes p105 NF-kB1 (SEQ ID No. 1) proteasomal processing to p50 (SEQ ID No. 3) which results in tumor suppression Further, overexpression of KPC1 (SEQ ID No. 4) or p50, suppresses tumor growth.

The amino acid sequence of p105 is as follows:

p105 human human protein
(SEQ ID No. 1)
MAEDDPYLGRPEQMFHLDPSLTHTIFNPEVFQPQMALPTADGPYLQILEQ

PKQRGFRFRYVCEGPSHGGLPGASSEKNKKSYPQVKICNYVGPAKVIVQL

VTNGKNIHLHAHSLVGKHCEDGICTVTAGPKDMVVGFANLGILHVTKKKV

FETLEARMTEACIRGYNPGLLVHPDLAYLQAEGGGDRQLGDREKELIRQA

ALQQTKEMDLSVVRLMFTAFLPDSTGSFTRRLEPVVSDAIYDSKAPNASN

LKIVRMDRTAGCVTGGEEIYLLCDKVQKDDIQIRFYEEEENGGVWEGFGD

FSPTDVHRQFAIVFKTPKYKDINITKPASVFVQLRRKSDLETSEPKPFLY

YPEIKDKEEVQRKRQKLMPNFSDSFGGGSGAGAGGGGMFGSGGGGGGTGS

TGPGYSFPHYGFPTYGGITFHPGTTKSNAGMKHGTMDTESKKDPEGCDKS

DDKNTVNLFGKVIETTEQDQEPSEATVGNGEVTLTYATGTKEESAGVQDN

LFLEKAMQLAKRHANALFDYAVTGDVKMLLAVQRHLTAVQDENGDSVLHL

AIIHLHSQLVRDLLEVTSGLISDDIINMRNDLYQTPLHLAVITKQEDVVE

DLLRAGADLSLLDRLGNSVLHLAAKEGHDKVLSILLKHKKAALLLDHPNG

DGLNAIHLAMMSNSLPCLLLLVAAGADVNAQEQKSGRTALHLAVEHDNIS

LAGCLLLEGDAHVDSTTYDGTTPLHIAAGRGSTRLAALLKAAGADPLVEN

FEPLYDLDDSWENAGEDEGVVPGTTPLDMATSWQVFDILNGKPYEPEFTS

DDLLAQGDMKQLAEDVKLQLYKLLEIPDPDKNWATLAQKLGLGILNNAFR

-continued

LSPAPSKTLMDNYEVSGGTVRELVEALRQMGYTEAIEVIQAASSPVKTTS

QAHSLPLSPASTRQQIDELRDSDSVCDSGVETSFRKLSFTESLTSGASLL

TLNKMPHDYGQEGPLEGKI

The nucleic acid sequence of p105 is as follows:

p105 human nucleotides
(SEQ ID No. 2)
atggcagaagatgatccatatttgggaaggcctgaacaaatgtttcatt tggatcctctttgactcatacaatatttaatccagaagtatttcaacc acagatggcactgccaacagcagatggcccataccttcaaatattagag caacctaaacagagaggatttcgtttccgttatgtatgtgaaggcccat cccatggtggactacctggtgcctctagtgaaaagaacaagaagtctta ccctcaggtcaaaatctgcaactatgtgggaccagcaaaggttattgtt cagttggtcacaaatggaaaaaatatccacctgcatgcccacagcctgg tgggaaaacactgtgaggatgggatctgcactgtaactgctggacccaa ggacatggtggtcggcttcgcaaacctgggtatacttcatgtgacaaag aaaaaagtatttgaaacactggaagcacgaatgacagaggcgtgtataa ggggctataatcctggactcttggtgcaccctgaccttgcctatttgca agcagaaggtggaggggaccggcagctgggagatcgggaaaaagagcta atccgccaagcagctctgcagcagaccaaggagatggacctcagcgtgg tgcggctcatgtttacagcttttcttccggatagcactggcagcttcac aaggcgcctggaacccgtggtatcagacgccatctatgacagtaaagcc cccaatgcatccaacttgaaaattgtaagaatggacaggacagctggat gtgtgactggaggggaggaaatttatcttctttgtgacaaagttcagaa agatgacatccagattcgattttatgaagaggaagaaaatggtggagtc tgggaaggatttggagattttccccacagatgttcatagacaatttg ccattgtcttcaaaactccaaagtataaagatattaatattacaaaacc agcctctgtgtttgtccagcttcggaggaaatctgacttggaaactagt gaaccaaaaccttttcctctactatcctgaaatcaaagataagaagaag tgcagaggaaacgtcagaagctcatgcccaatttttcggatagtttcgg cggtggtagtggtgctggagctggaggcggaggcatgtttggtagtggc ggtggaggaggggggcactggaagtacaggtccagggtatagcttcccac actatggatttcctacttatggtgggattactttccatcctggaactac taaatctaatgctgggatgaagcatggaaccatggacactgaatctaaa aaggaccctgaaggttgtgacaaagtgatgacaaaaacactgtaaacc tctttgggaaagttattgaaaccacagagcaagatcaggagcccagcga ggccaccgttgggaatggtgaggtcactctaacgtatgcaacaggaaca aaagaagagtgctggagttcaggataacctctttctagagaaggcta tgcagcttgcaaagaggcatgccaatgccctttcgactacgcggtgac aggagacgtgaagatgctgctggccgtccagcgccatctcactgctgtg caggatgagaatggggacagtgtcttacacttagcaatcatccaccttc

```
attctcaacttgtgagggatctactagaagtcacatctggtttgatttc
tgatgacattatcaacatgagaaatgatctgtaccagacgcccttgcac
ttggcagtgatcactaagcaggaagatgtggtggaggatttgctgaggg
ctggggccgacctgagccttctggaccgcttgggtaactctgttttgca
cctagctgccaaagaaggacatgataaagttctcagtatcttactcaag
cacaaaaaggcagcactacttcttgaccaccccaacggggacggtctga
atgccattcatctagccatgatgagcaatagcctgccatgtttgctgct
gctggtggccgctgggctgacgtcaatgctcaggagcagaagtccggg
cgcacagcactgcacctggctgtggagcacgacaacatctcattggcag
gctgcctgctcctggagggtgatgcccatgtggacagtactacctacga
tggaaccacacccctgcatatagcagctgggagagggtccaccaggctg
gcagctcttctcaaagcagcaggagcagatcccctggtggagaactttg
agcctctctatgacctggatgactctgggaaaatgcaggagaggatga
aggagttgtgcctggaaccacgcctctagatatggccaccagctggcag
gtatttgacatatttaaatgggaaccatatgagccagagtttacatctg
atgatttactagcacaaggagacatgaaacagctggctgaagatgtgaa
gctgcagctgtataagttactagaaattcctgatccagacaaaaactgg
gctactctggcgcagaaattaggtctggggatacttaataatgccttcc
ggctgagtcctgctccttccaaaacacttatggacaactatgaggtctc tgggggtacagtcagagagctggtggaggccctgagacaaatgggctac
accgaagcaattgaagtgatccaggcagcctccagcccagtgaagacca
cctctcaggcccactcgctgcctctctcgcctgcctccacaaggcagca
aatagacgagctccgagacagtgacagtgtctgcgacagcggcgtggag
acatccttccgcaaactcagctttaccgagtctctgaccagtggtgcct
cactgctaactctcaacaaaatgcccatgattatgggcaggaaggacc
tctagaaggcaaaatttag
```

The amino acid sequence of p50 is as follows:

```
p50 human
                                              (SEQ ID No. 3)
MAEDDPYLGRPEQMFHLDPSLTHTIFNPEVFQPQMALPTADGPYLQILEQ
PKQRGFRFRYVCEGPSHGGLPGASSEKNKKSYPQVKICNYVGPAKVIVQ
LVTNGKNIHLHAHSLVGKHCEDGICTVTAGPKDMVVGFANLGILHVTKKK
VFETLEARMTEACIRGYNPGLLVHPDLAYLQAEGGGDRQLGDREKELIRQ
AALQQTKEMDLSVVRLMFTAFLPDSTGSFTRRLEPVVSDAIYDSKAPNAS
NLKIVRMDRTAGCVTGGEEIYLLCDKVQKDDIQIRFYEEEENGGVWEGFG
DFSPTDVHRQFAIVFKTPKYKDINITKPASVFVQLRRKSDLETSEPKPFL
YYPEIKDKEEVQRKRQKLPNFSDSFGGGSGAGAGGGGMFGSGGGGGTGS
TGPGYSFPHYGFPTYGGITFHPGTTKSNAGMKHGT
```

The amino acid sequence of KPC1 (human) is as follows:

```
KPC1 human
                                              (SEQ ID No. 4)
MASKGAGMSFSRKSYRLTSDAEKSRVTGIVQEKLLNDYLNRIFSSSEHAPPAATS
RKPLNFQNLPEHLDQLLQVDNEEEESQGQVEGRLGPSTVVLDHTGGFEGLLLVD
D DLLGVIGHSN FGTIRSTTCV YKGKWLYEVL ISSQGLMQIG
WCTISCRFNQEEGVGDTHNSYAYDGNRVRKWNVTTTNYGKAWAAGDIVSCLID
LDDGTLS FCLNGVSLGT AFENLSRGLG MAYFPAIS LS FKESVAFNFG
SRPLRYPVAG YRPLQDPPSA DLVRAQRLLG CFRAVLSVEL DPVEGRLLDK
ESSKWRLRGQ PTVLLTLAHI FHHFAPLLRK VYLVEAVLMS FLLGIVEKGT
PTQAQSVVHQ VLDLLWLFME DYEVQDCLKQ LMMSLLRLYR FSPIVPDLGL
QIHYLRLTIA ILRHEKSRKF LLSNVLFDVL RSVVFFYIKS PLRVEEAGLQ
ELIPTTWWPH CSSREGKEST EMKEETAEER LRRRAYERGC QRLRKRIEVV
EELQVQILKL LLDNKDDNGG EASRYIFLTK FRKFLQENAS GRGNMPMLCP
PEYMVCFLHR LISALRYYWD EYKASNPHAS FSEEAYIPPQ VFYNGKVDYF
DLQRLGGLLS HLRKTLKDDL ASKANIVIDP LELQSTAMDD LDEDEEPAPA
MAQRPMQALA VGGPLPLPRP GWLSSPTLGR ANRFLSTAAV SLMTPRRPLS
TSEKVKVRTL SVEQRTREDI EGSHWNEGLL LGRPPEEPEQ PLTENSLLEV
LDGAVMMYNL SVHQQLGKMV GVSDDVNEYA MALRDTEDKL RRCPKRRKDI
LAELTKSQKV FSEKLDHLSR RLAWVHATVY SQEKMLDIYW LLRVCLRTIE
HGDRTGSLFA FMPEFYLSVA INSYSALKNY FGPVHSMEEL PGYEETLTRL
AAILAKHFAD ARIVGTDIRD SLMQALASYV CYPHSLRAVE RIPEEQRIAM
```

VRNLLAPYEQ RPWAQTNWIL VRLWRGCGFG YRYTRLPHLL KTKLEDANLP

SLQKPCPSTL LQQHMADLLQ QGPDVAPSFL NSVLNQLNWA FSEFIGMIQE

IQQAAERLER NFVDSRQLKV CATCFDLSVS LLRVLEMTIT LVPEIFLDWT

RPTSEMLLRR LAQLLNQVLN RVTAERNLFD RVVTLRLPGL ESVDHYPILV

AVTGILVQLL VRGPASEREQ ATSVLLADPC FQLRSICYLL GQPEPPAPGT

ALPAPDRKRF SLQSYADYIS ADELAQVEQM LAHLTS AS AQ AAAASLPTSE

EDLCPICYAH PISAVFQPCG HKSCKACINQ HLMNNKDCFF CKTTIVSVED

WEKGANTSTT SSAA

KPC1 human protein is encoded by the following nucleotides sequence:

(SEQ ID No. 5)

ATGG CATCCAAGGG GGCCGGCATG TCTTTCTCCC GCAAGAGCTA

TAGGCTGACC TCAGATGCTG AGAAATCCAG GGTCACAGGC ATTGTGCAGG

AGAAGCTGCT GAATGACTAC CTGAACCGCA TCTTTTCCTC TTCTGAACAT

GCACCCCCAG CAGCCACCAG CAGGAAACCC CTGAACTTCC AGAACCTGCC

AGAACATTTG GACCAGTTGC TACAGGTGGA CAATGAGGAG GAGGAAAGCC

AGGGACAGGT TGAAGGGCGG CTTGGCCCAT CCACTGTGGT CCTGGACCAC

ACAGGCGGCT TTGAGGGGCT TCTCCTGGTG GATGATGACC TGCTGGGGGT

GATTGGACAC AGCAACTTTG CACCATCCG CTCTACCACA TGCGTGTACA

AAGGGAAATG GCTCTACGAG GTCCTCATCT CCTCCCAGGG GCTCATGCAG

ATCGGCTGGT GCACCATCAG CTGCCGCTTC AACCAGGAGG AGGGGGTTGG

AGATACACAC AACTCCTATG CCTATGATGG CAACCGCGTG CGCAAGTGGA

ATGTGACCAC AACGAATTAT GGCAAGGCGT GGGCAGCGGG GGACATCGTG

AGCTGCCTGA TTGACCTGGA TGATGGCACT CTGTCCTTCT GCCTGAACGG

TGTATCACTG GCACTGCCT TTGAGAACCT GTCCAGGGGC CTGGGTATGG

CCTACTTCCC AGCCATCAGC CTCTCTTTCA AGGAGTCCGT GGCCTTCAAC

TTTGGCAGCC GTCCTCTGCG CTACCCAGTG GCAGGCTACC GGCCCCTGCA

GGACCCACCG AGTGCTGACC TGGTGCGGGC ACAGAGGTTG CTGGGCTGCT

TCCGGGCAGT GCTGAGTGTG GAGCTGGACC CTGTGGAGGG GCGGCTGTTG

GACAAGGAGA GCTCCAAGTG GCGGTTGCGG GGCCAGCCCA CCGTCCTCCT

CACACTGGCC CACATCTTCC ATCACTTTGC ACCGCTTCTG CGCAAGGTGT

ATCTGGTGGA GGCTGTGCTC ATGAGCTTCT TGCTGGGCAT CGTGGAGAAG

GGCACACCCA CACAGGCACA GTCCGTGGTG CACCAGGTCC TGGACCTCTT

GTGGCTCTTC ATGGAGGACT ACGAGGTACA AGATTGCCTC AAGCAGTTGA

TGATGTCTCT GCTTCGGCTG TACCGATTCT CACCCATTGT CCCAGACCTG

GGCCTACAGA TCCATTACCT GCGGCTCACT ATCGCCATCC TGAGGCATGA

GAAGTCCCGC AAGTTTCTGC TTAGCAATGT CCTCTTCGAC GTGCTCCGCT

CCGTCGTCTT CTTTTACATC AAGAGCCCCC TGCGTGTGGA GGAGGCCGGC

CTGCAGGAGC TCATTCCCAC CACCTGGTGG CCCCACTGCT CCAGTAGGGA

GGGCAAAGAG AGCACGGAGA TGAAGGAGGA GACCGCAGAG

GAGCGGCTGC GGCGGCGAGC CTACGAACGG GGCTGTCAGC GGCTCAGGAA

GCGCATCGAA GTGGTGGAAG AACTACAGGT CCAGATCCTG AAGCTGCTGC

```
TGGACAATAA AGATGACAAT GGGGGTGAAG CTTCTAGGTA TATCTTCCTG

ACCAAGTTTC GCAAGTTTCT GCAGGAGAAC GCCAGTGGCC GGGGGAACAT

GCCCATGCTC TGCCCCCCTG AGTACATGGT CTGCTTCTTA CACCGGCTGA

TCTCTGCCCT GCGCTACTAT TGGGATGAAT ACAAGGCTTC CAATCCTCAT

GCTTCCTTCA GTGAGGAGGC CTACATCCCG CCCCAGGTCT TCTATAATGG

CAAGGTGGAC TACTTTGACC TGCAGCGCCT GGGGGGCCTC CTCTCGCACC

TGCGGAAGAC CCTCAAAGAT GACCTTGCTT CCAAAGCCAA CATTGTGATC

GACCCACTGG AGCTCCAGTC AACCGCCATG GATGACCTAG ATGAGGATGA

GGAGCCAGCC CCAGCTATGG CCCAGCGCCC CATGCAGGCC CTGGCTGTTG

GGGGGCCACT GCCCCTGCCC CGGCCCGGCT GGCTCAGTTC TCCAACTTTG

GGCCGAGCCA ACCGCTTCCT CAGCACAGCG GCTGTGAGCC TCATGACCCC

ACGGCGGCCT CTGAGCACCT CGGAGAAAGT GAAGGTCCGC ACGCTGAGCG

TGGAGCAGAG GACCCGTGAG GACATTGAAG GCAGCCACTG GAATGAGGGC

TTGCTGCTGG GGCGGCCCCC CGAGGAGCCT GAGCAGCCCC TCACCGAGAA

CTCGCTGCTG GAAGTCCTGG ATGGGCGGT CATGATGTAC AACCTCAGCG

TACACCAGCA GCTGGGCAAG ATGGTGGGTG TCTCCGATGA TGTCAATGAA

TACGCTATGG CTCTGAGGGA CACAGAGGAC AAGCTCCGCC GGTGCCCCAA

GAGGAGGAAG GACATCCTTG CAGAGTTGAC CAAGAGCCAG AAGGTTTTCT

CAGAAAAGCT GGACCACCTG AGCCGCCGTC TTGCCTGGGT CCATGCCACT

GTCTACTCCC AGGAGAAGAT GCTGGACATC TACTGGCTGC TGCGCGTCTG

CCTGCGGACC ATTGAGCACG GTGATCGCAC AGGGTCTCTC TTTGCCTTCA

TGCCCGAGTT CTACCTGAGC GTGGCCATCA ACAGCTACAG TGCTCTCAAG

AATTACTTTG GTCCCGTGCA CAGCATGGAG GAGCTCCCAG CTATGAAGA

GACCCTGACC CGCCTGGCTG CCATTCTCGC CAAACACTTT GCCGACGCAC

GCATTGTGGG CACTGACATC CGAGACTCAC TGATGCAGGC CCTGGCCAGC

TACGTGTGCT ACCCACACTC CCTGCGGGCT GTGGAGCGAA TCCCCGAGGA

GCAGCGTATC GCCATGGTGA GGAACCTCCT GGCGCCCTAT GAGCAGCGGC

CCTGGGCCCA GACCAACTGG ATCCTGGTGC GGCTCTGGAG GGGCTGTGGC

TTCGGGTACC GCTATACACG GCTGCCACAT CTGCTGAAAA CCAAACTTGA

GGACGCCAAT TTGCCCAGCC TCCAGAAGCC CTGCCCTTCC ACCCTGCTGC

AGCAGCACAT GGCGGACCTC CTACAGCAGG GTCCTGATGT GGCACCCAGC

TTCCTCAACA GCGTCCTCAA TCAGCTCAAC TGGGCCTTCT CTGAATTCAT

TGGCATGATC CAAGAGATCC AGCAGGCTGC TGAGCGCCTG GAGCGGAACT

TTGTGGACAG CCGGCAGCTC AAGGTATGTG CCACCTGCTT TGACCTCTCG

GTCAGCCTGC TGCGTGTCTT GGAGATGACT ATCACACTGG TGCCTGAGAT

ATTCCTTGAC TGGACCCGGC CTACCTCTGA GATGCTGCTG CGGCGTCTTG

CACAGCTGCT AAACCAGGTG CTGAACCGGG TGACAGCTGA GAGGAACCTG

TTTGATCGTG TGGTCACCCT ACGGCTGCCT GGCCTAGAGA GCGTGGACCA

CTATCCCATT CTGGTGGCAG TGACGGGCAT CCTGGTGCAG CTCCTGGTGC

GTGGCCCAGC CTCAGAGAGA GAGCAAGCCA CATCAGTGCT CCTGGCAGAT
```

-continued

```
CCCTGCTTCC AGCTACGCTC AATATGCTAT CTCCTGGGAC AGCCAGAGCC

CCCAGCACCT GGCACTGCTC TGCCAGCCCC TGACCGGAAG CGCTTCTCCC

TGCAGAGCTA TGCGGATTAT ATCAGTGCCG ATGAGCTGGC CCAAGTGGAA

CAGATGCTGG CGCACCTGAC CTCTGCATCT GCCCAGGCAG CAGCTGCCTC

CCTGCCCACC AGTGAGGAGG ACCTCTGCCC CATCTGCTAT GCCCACCCCA

TCTCTGCTGT GTTCCAGCCC TGTGGCCACA AGTCCTGCAA AGCCTGTATC

AACCAGCACC TGATGAACAA CAAGGACTGC TTCTTCTGCA AAACCACCAT

CGTGTCTGTA GAGGACTGGG AGAAGGGAGC CAATACGAGT ACTACCTCCT

CAGCTGCCTA G
```

For example, mouse (*Mus musculus*) KPC1 (SEQ ID No. 6) is as follows:

MASKGTGMSFSRKSYRLTSDAEKSRVTGIVQEKLLSDYLYRIFSPPDRGP
AAATSRKPLNFHNLPEHVDQLLQVDSEDNESQGQVEGRLGPSTVVLDHTG
GFEGLLLVDDDLLGVIGHSNFGTIRSTTCVYKGKWVYEVLISSQGLMQIG
WCTINCRFNQEEGVGDTHNSYAYDGNRVRKWNVTTTNYGKAWAAGDIVSC
LIDLDDGTLSFCLNGVSLGTAFENLSRGLGMAYFPAISLSFKESVAFNFG
SRPLRYPVAGFRPLQDPPFADLVRAQRLLGCFQAVLSVELDPVEGRLVET
ESSEWQLQGQPTVLLTLAHIFHHFAPLLRKVYLVEAVLMSFLLGVVEKGT
PEQAQSVVHQILDLLWLFMEDYEVQDCLKQLMMSLLRLYRFSPIVPDLGL
QIHYLRLTMSILRHEKSRKFLLSNVLFDMLRSVVFFYIKSPLRVEEAGLK
ELIPTTWWPHRSSRESRDGKEAREETTEERQRRAYERGCQRLKKRIEVV
EELQVQILKLLLDNKDDNGGEASRYIFLTKFRKFLQENASGRGNTPVLCP
PEYMVCFLHRLVSALRFYWDEYKASNPRASFSEEAYIPPQIFYNGKVDYF
DLQRLGGLLSHLRKTLKDDLASKANIVIDPLELQAATMDDLDEDEEPAPS
AAQVWQEGQRPMQALAIGGALPLPRPGWLSSPTLGRANRFLSTAAVSLMT
PRRLLSTMEKVKVRSLNVEQRTREDIEGSHWNEGLLLGRPPEEPEQPLTE
NSLLEVLDGTVMMYNLSVHQQLGKMVGVSDDVNEYAMALRDTEDKLRRCP
KRRKDILAELTKSQKVFSEKLDHLSRRLAWVHATVYSQEKMLDIYWLLRV
CLRTIEHGDRTGSLFAFMPEFYLSVAINSYSALKNYFGPVHSMEELPGYE
ETLTRLAAILAKHFADPRIVGTDIRDSLMQALASYVCYPHSLRAVERIPE
EQRIAMVRNLLAPYEQRPWAQTNWILVRLWRGCGFGYRYTRLPHLLKTKP
EDANLPSLQKPCPSTLLQQHMADLLRQGSDVAPSFLNSVLNQLNWAFSEF
IGMIQEIQQAAERLERNFVDSRQLKVCATCFDLSVSLLRVLEMTITLVPE
IFLDWSRPTSEMLLRRLAQLLNQVLNRVTAERNLFDRVVTLRLPGLESVD
HYPILVAVTGILVRLLVHGPTSETEQATSVLLADPCFQLRSICYLLGQPE
PLAPGTTLPAPDRKRFSLQSYTDYISAEELAQVEQMLAHLTAASAQAAAA
SLPTNEEDLCPICYAHPISAVFQPCGHKSCKACINQHLMNNKDCFFCKAT
IVSVEDWDKAANTSAMSSAA

The mouse (*Mus musculus*) KPC1 (SEQ ID No. 6) is encoded by SEQ ID No. 7:

KPC1 mice nucleotides
```
ATGGCGTCCAAGGGGACTGGCATGTCGTTCTCCCGAAAGAGCTATAGGCT
GACCTCAGATGCTGAGAAGTCCAGGGTCACAGGCATCGTGCAAGAGAAAC
TACTGAGCGACTATCTGTACCGCATCTTTTCCCCTCCTGACCGTGGACCC
GCCGCAGCCACCAGCAGGAAACCGCTAAACTTCCATAACCTGCCTGAGCA
CGTGGACCAGCTGCTACAGGTGGACAGTGAAGACAACGAGAGCCAGGGAC
AAGTTGAAGGTCGACTTGGCCCATCTACTGTGGTCCTAGACCACACAGGA
GGCTTTGAGGGGCTTCTCCTTGTGGATGATGACCTCCTGGGGGTGATTGG
ACACAGCAACTTTGGCACTATCCGTTCTACCACATGTGTGTACAAAGGGA
AGTGGGTCTACGAGGTGCTCATCTCCTCCCAGGGCCTCATGCAGATCGGC
TGGTGCACCATCAACTGCCGCTTTAATCAGGAGGAAGGGGTTGGAGACAC
ACATAACTCCTATGCCTATGACGGCAACCGAGTGCGCAAGTGGAATGTTA
CCACCACGAATTATGGCAAGGCGTGGGCTGCGGGGGACATTGTCAGCTGC
CTAATTGATCTGGATGATGGGACTCTGTCCTTCTGCCTGAATGGCGTGTC
ACTGGGCACTGCCTTCGAGAACCTTTCCAGGGGCCTAGGAATGGCGTACT
TCCCAGCCATCAGCCTGTCATTCAAGGAGTCTGTGGCATTCAACTTTGGC
AGCCGTCCTTTGCGCTACCCAGTTGCGGGCTTCCGGCCCCTGCAGGACCC
TCCGTTTGCTGACCTGGTCCGGGCACAGAGGTTGCTGGGCTGCTTCCAGG
CAGTGCTAAGTGTGGAGCTGGACCCTGTGGAAGGGCGGCTGGTGGAGACG
GAGAGCTCTGAGTGGCAGCTGCAAGGGCAGCCCACTGTCCTCCTCACGCT
GGCCCACATCTTCCATCACTTTGCACCACTGCTGCGCAAGGTATACCTGG
TGGAGGCTGTGCTAATGAGCTTCCTGCTGGGCGTTGTGGAGAAGGGCACA
CCAGAGCAGGCGCAGTCTGTGGTACACCAGATCTTGGACCTCTTGTGGCT
CTTCATGGAGGACTATGAGGTACAGGATTGCCTGAAGCAGTTGATGATGT
CACTTCTACGTCTCTACCGATTCTCGCCTATTGTCCCAGACCTGGGTCTA
CAGATCCACTACCTGCGCCTCACTATGTCCATCCTGAGACACGAGAAGTC
CCGCAAGTTCCTGCTTAGCAATGTCCTTTTTGACATGCTCCGGTCCGTGG
TCTTCTTTTATATTAAGAGTCCCCTGCGTGTGGAGGAAGCTGGCCTGAAG
GAACTCATTCCCACCACCTGGTGGCCCCATCGCTCCAGCAGGGAGAGCAG

```
AGACGGTAAGGAAGCAAGGGAGGAGACCACCGAAGAGCGGCAGCGGAGGC
GAGCCTATGAGCGTGGCTGCCAAAGACTCAAGAAACGCATTGAAGTGGTG
GAAGAACTGCAGGTCCAGATCCTGAAGCTGCTGTTGGACAATAAAGATGA
CAATGGGGGTGAAGCTTCTAGGTACATCTTTCTGACAAAATTCCGAAAGT
TCCTGCAGGAGAATGCCAGCGGCCGGGGGAACACACCCGTGCTCTGCCCC
CCTGAGTACATGGTCTGCTTCCTACACCGGCTGGTGTCTGCCTTGCGCTT
CTATTGGGATGAATACAAAGCTTCCAACCCCCGTGCTTCCTTCAGTGAGG
AGGCTTACATCCCGCCCCAGATCTTCTATAATGGCAAGGTGGACTACTTT
GACCTTCAGCGCCTTGGGGGCCTCCTCTCACACCTTCGAAAGACCCTTAA
AGATGACCTTGCTTCCAAAGCCAACATCGTGATCGACCCCCTGGAGCTCC
AGGCAGCCACCATGGATGACCTGGATGAGGATGAAGAGCCTGCCCCCTCA
GCGGCCCAGCGTCCGATGCAAGCCCTGGCCATCGGAGGGGCACTGCCCCT
GCCCCGGCCAGGCTGGCTCAGTTCTCCAACCCTGGGCAGAGCCAACCGCT
TCCTCAGCACGGCAGCTGTGAGCCTCATGACCCCACGGCGGCTTCTGAGC
ACCATGGAGAAAGTCAAAGTTCGCTCACTGAATGTGGAACAGAGGACCCG
TGAGGACATTGAGGGCAGCCACTGGAATGAGGGCCTGCTGTTGGGGAGGC
CCCCTGAAGAGCCTGAGCAGCCGCTTACCGAGAACTCGCTGTTGGAAGTC
CTGGATGGCACAGTCATGATGTATAACCTCAGCGTTCACCAGCAGCTGGG
CAAGATGGTGGGTGTGTCTGATGATGTCAACGAGTATGCAATGGCCCTAA
GAGACACAGAGGACAAGCTCCGTCGGTGCCCTAAGAGGAGGAAGGATATC
CTTGCAGAGTTGACCAAGAGCCAGAAGGTTTTCTCAGAAAAGCTGGACCA
CCTGAGCCGCAGGCTTGCCTGGGTCCACGCCACAGTCTACTCACAGGAGA
AAATGCTGGATATCTACTGGTTACTGCGTGTCTGCCTACGGACCATTGAG
CATGGGACCGCACGGGGTCTCTCTTTGCCTTCATGCCTGAGTTCTACCT
AAGTGTGGCTATCAACAGCTACAGTGCCCTGAAGAACTATTTTGGCCCTG
TGCACAGCATGGAGGAACTCCCAGGCTATGAAGAGACCCTGACACGCTTA
GCTGCCATCCTCGCCAAACACTTTGCTGACCCTCGAATAGTAGGCACTGA
TATTCGAGACTCACTGATGCAGGCCCTGGCCAGCTATGTGTGCTACCCAC
ACTCCCTGCGGGCTGTGGAACGGATTCCTGAGGAACAGCGCATCGCCATG
GTGAGGAACCTTTTGGCACCCTATGAGCAACGGCCCTGGGCCCAGACCAA
CTGGATCCTGGTGCGGCTTTGGAGGGGCTGTGGGTTTGGGTACCGCTATA
CACGGCTGCCACATCTGCTGAAAACCAAGCCAGAGGATGCCAATTTGCCC
AGCCTCCAAAAGCCCTGCCCTTCGACCTTGCTACAGCAGCACATGGCGGA
CCTGCTGCGACAAGGGTCTGATGTGGCACCGAGCTTCCTCAACAGTGTCC
TTAACCAGCTCAACTGGGCCTTCTCTGAGTTCATCGGCATGATCCAGGAG
ATTCAACAGGCTGCTGAACGCCTGGAGCGGAACTTTGTGGACAGCCGACA
GCTCAAGGTCTGTGCCACCTGCTTTGACCTGTCGGTCAGCTTGTTGCGCG
TCTTGGAAATGACCATCACGCTGGTACCTGAAATATTCCTTGACTGGTCC
CGCCCTACCTCTGAGATGCTGCTTCGGCGTCTGGCACAGCTGCTGAACCA
GGTGCTGAACCGGGTGACAGCTGAGAGGAACCTGTTTGACCGTGTAGTTA
CCCTACGGCTACCTGGGCTGGAGAGTGTGGACCACTACCCTATCCTGGTG
GCAGTGACTGGCATCCTGGTACGCCTCCTGGTGCACGGCCCAACCTCAGA
GACAGAGCAAGCCACCTCTGTGCTCCTGGCTGATCCCTGCTTCCAGCTTC
GTTCCATATGCTATCTCCTGGGGCAGCCAGAGCCCCTAGCACCTGGCACT
ACCTTGCCTGCCCCTGACCGGAAACGCTTCTCTCTACAGAGTTATACAGA
TTATATCAGCGCTGAGGAGCTGGCCCAGGTGGAACAGATGCTGGCTCACC
TGACCGCTGCATCTGCCCAGGCGGCCGCCGCCTCCCTGCCCACCAATGAA
GAGGACCTCTGCCCAATCTGCTACGCCCACCCCATCTCTGCTGTGTTCCA
GCCTTGTGGTCACAAATCCTGCAAAGCCTGCATCAACCAGCACCTGATGA
ACAACAAGGACTGCTTCTTCTGCAAAGCCACCATTGTATCTGTAGAGGAC
TGGGACAAGGCAGCCAACACAAGCGCCATGTCCTCAGCTGCCTAG
```

In some embodiments of the invention, there is provided a method for treating cancer comprising the step of administering a therapeutically effective amount of KPC1, a peptide which is at least about 70% homologous to the KPC1 sequence as set forth in SEQ ID No. 4 or an agent which up-regulates KPC1; a fused protein comprising KPC1, the peptide which is at least about 70% homologous to the KPC1 sequence as set forth in SEQ ID No. 4 or the agent which up-regulates KPC1; or a complex comprising KPC1, the peptide which is at least about 70% homologous to the KPC1 sequence as set forth in SEQ ID No. 4, or the agent that upregulates KPC1; or the fused protein that comprises KPC1 or the peptide which is at least about 70% homologous to the KPC1 sequence as set forth in SEQ ID No. 4 or the agent which up-regulates KPC1, to a subject in need, thereby treating cancer.

In some embodiments of the invention, there is provided a method for treating cancer comprising the step of administering a therapeutically effective amount of functionally related variant of the KPC1 or a functionally active fragment of KPC1, a fused protein comprising the functionally related variant of the KPC1 or the functionally active fragment of KPC1 or a complex comprising the functionally related variant of the KPC1 or the functionally active fragment of KPC1, or the fused protein that comprises the functionally related variant of the KPC1 or the functionally active fragment of KPC1, to a subject in need, thereby treating cancer.

In some embodiments of the invention, there is provided a method for treating cancer comprising the step of administering a therapeutically effective amount of p50, a peptide which is at least about 70% homologous to the p50 sequence as set forth in SEQ ID No. 3 or an agent which upregulates p50; a fused protein comprising p50 or the peptide which is at least about 70% homologous to the p50 sequence as set forth in SEQ ID No. 3, or the agent which up-regulates p50; or a complex comprising p50, the peptide which is at least about 70% homologous to the p50 sequence as set forth in SEQ ID No. 3 or the agent which upregulates p50, or the fused protein that comprises p50, the peptide which is at least about 70% homologous to the p50 sequence as set forth in SEQ ID No. 3 or the agent which upregulates p50, to a subject in need, thereby treating cancer.

In some embodiments of the invention, there is provided a method for treating cancer comprising the step of administering a therapeutically effective amount of functionally related variant of the p50 or a functionally active fragment of p50, a fused protein comprising the functionally related variant of the p50 or the functionally active fragment of p50 or a complex comprising either the functionally related variant of the p50 or the functionally active fragment of p50, the fused protein that comprises the functionally related variant of the p50 or the functionally active fragment of p50 to a subject in need, thereby treating cancer.

In some embodiments of the invention, there is provided a functionally equivalent molecule that mimics a functional activity of the KPC1 or the functionally related variant thereof, wherein the molecule is a peptidomimetic or a stapled peptide or a chemical compound.

In some embodiments of the invention, there is provided a functionally equivalent molecule that mimics a functional activity of the p50 or the functionally related variant thereof wherein the molecule is a peptidomimetic or a stapled peptide or a chemical compound.

As used in the term "protein(s) of the invention" peptide(s) of the invention", active ingredient(s) of the invention", "the peptide(s)", "the protein (s)", the "active ingredient(s)" refers inter-alia to any of the following:

KPC1, a peptide which is at least about 70% homologous to the KPC1 sequence as set forth in SEQ ID No. 4, an agent which upregulates KPC1; a fused protein comprising KPC1, the peptide which is at least about 70% homologous to the KPC1 sequence as set forth in SEQ ID No. 4 or the agent which up-regulates KPC1, or a complex comprising either KPC1, the peptide which is at least about 70% homologous to the KPC1 sequence as set forth in SEQ ID No. 4 or the agent which upregulates KPC1, or a fused protein that comprises KPC1, the peptide which is at least about 70% homologous to the KPC1 sequence as set forth in SEQ ID No. 4 or the agent which upregulates KPC1; a functionally related variant of the KPC1 or a functionally active fragment of KPC1 or a fused protein comprising them, p50, a peptide which is at least about 70% homologous to the p50 sequence as set forth in SEQ ID No. 3 or an agent which upregulates p50; or a fused protein or a complex comprising them; a functionally related variant of the p50 or the functionally active fragment of p50 or a fused protein or a complex comprising them. Further included is a functionally equivalent molecule that mimics a functional activity of these proteins or peptides.

In one embodiment of the invention, this invention provides a functionally equivalent molecule that mimics the functional activity of any of the peptide or peptide variants provided in this invention. The term "functionally equivalent molecule" refers in the application to any compound such as but not restricted to peptidomimetic or stapled peptide. The functionally equivalent molecule may be obtained by retro-inverso or D-retro-enantiomer peptide technique, consisting of D-amino acids in the reversed sequence. The functionally equivalent molecule may be obtained by using amino acid derivative.

In some embodiments of the invention, there is provided a method for treating cancer comprising the step of contacting cancerous cells of the subject with a therapeutically effective amount of KPC1, a peptide which is at least about 70% homologous to the KPC1 sequence as set forth in SEQ ID No. 4 or an agent which up-regulates KPC1, a fused protein comprising KPC1, the peptide which is at least about 70% homologous to the KPC1 sequence as set forth in SEQ ID No. 4 or the agent which up-regulates KPC1, or a complex comprising, KPC1 or the peptide which is at least about 70% homologous to the KPC1 sequence as set forth in SEQ ID No. 4 or the fused protein that comprises KPC1 or the peptide which is at least about 70% homologous to the KPC1 sequence as set forth in SEQ ID No. 4 or the agent which up-regulates KPC1, to a subject in need, thereby treating cancer.

According to some embodiments of the invention, the contacting is effected in-vivo.

According to some embodiments of the invention, the contacting is effected ex-vivo.

As used herein the term "treating cancer" refers to preventing, curing, reversing, attenuating, alleviating, minimizing or suppressing the cancer, as well as resulting in one or more of the following parameters: reduction in tumor size or burden, blocking of tumor growth, shifting the phenotype of the macrophage from M2 to M1, reduction in tumor-associated pain, long-term non-progression, induction of remission, reduction of metastasis, or increased patient survival.

As used herein the term "cancer" refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Typically, the cancer cells are in the form of a tumor; existing locally within an animal, or circulating in the blood stream as independent cells, for example, leukemic cells.

In some embodiments of the invention, the cancer is an oral cancer, oropharyngeal cancer, nasopharyngeal cancer, respiratory cancer, a urogenital cancer, a gastrointestinal cancer, a central or peripheral nervous system tissue cancer, an endocrine or neuroendocrine cancer or a hematopoietic cancer.

According to some embodiments of the invention, the cancer is a glioma, a sarcoma, a carcinoma, a lymphoma, a melanoma, a fibroma, or a meningioma.

According to some embodiments of the invention, the cancer is brain cancer, oropharyngeal cancer, nasopharyngeal cancer, renal cancer, biliary cancer, prostatic cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer.

In some embodiments of the invention, the cancer is a breast cancer, a pancreatic cancer or a lung cancer.

In some embodiment the cancer is breast cancer, bone osteosarcoma or glioblastoma.

In some embodiments of the invention, there is provided a method of preventing or reducing metastasis comprising the step of administering a therapeutically effective amount of KPC1, a peptide which is at least about 70% homologous to the KPC1 sequence as set forth in SEQ ID No. 4 or an agent which up-regulates KPC1; a fused protein comprising KPC1, the peptide which is at least about 70% homologous to the KPC1 sequence as set forth in SEQ ID No. 4 or the agent which up-regulates KPC1; or a complex comprising KPC1 or the peptide which is at least about 70% homologous to the KPC1 sequence as set forth in SEQ ID No. 4 or the fused protein that comprises KPC1 or the peptide which is at least about 70% homologous to the KPC1 sequence as set forth in SEQ ID No. 4 or the agent which up-regulates KPC1, to a subject in need.

In some embodiments of the invention, there is provided a method of preventing or reducing metastasis comprising the step of administering a therapeutically effective amount of p50, a peptide which is at least about 70% homologous to the p50 sequence as set forth in SEQ ID No. 3 or an agent which upregulates p50; a fused protein comprising p50, the peptide which is at least about 70% homologous to the p50 sequence as set forth in SEQ ID No. 3 or the agent which up-regulates p50, or a complex comprising p50, the peptide which is at least about 70% homologous to the p50 sequence as set forth in SEQ ID No. 3 or the agent which upregulates p50 or a fused protein that comprises p50, the peptide which is at least about 70% homologous to the p50 sequence as set forth in SEQ ID No. 3 or the agent which upregulates p50.

In some embodiments there is provided a method of treating cancer by administering a therapeutically effective amount of a nucleic acid sequence that encodes to KPC1, or to a peptide which is at least about 70% homologous to the KPC1 sequence as set forth in SEQ ID No. 4, or a nucleic acid that encodes to a fused protein comprising KPC1 or peptide which is at least about 70% homologous to the KPC1 sequence as set forth in SEQ ID No. 4 or a nucleic acid that encodes to an agent which up-regulates KPC1 or the fusion protein comprising the same. In some embodiments, the nucleic acid is as set for in SEQ ID. No. 5.

In some embodiments there is provided a method of treating cancer by administering a therapeutically effective amount of a nucleic acid sequence that encodes to p50 or to a peptide which is at least about 70% homologous to the p50 sequence as set forth in SEQ ID No. 3, or a nucleic acid that encodes to a fused protein comprising p50 or peptide which is at least about 70% homologous to the p50 sequence as set forth in SEQ ID No. 3 or a nucleic acid that encodes to an agent which up-regulates the processing of p105 to p50.

The method may further comprise administering a second anti-cancer therapy or a third anti-cancer therapy to the treated subject. The second and third anti-cancer therapies may be one or two or more of chemotherapy, radiotherapy, hormonal therapy, cytokine therapy, immunotherapy, targeted therapy, e.g., bortezomib, sunitinib, Herceptin, sorafenib and/or surgery. The second and third anti-cancer therapy may be administered to the subject prior to or after the KPC1 treatment or concurrent with the KPC1 treatment.

In some embodiments, the method of treatment may further comprise assessing the efficacy of the treatment by performing a PET scan on said subject or measuring the level of the relevant bio-markers.

Specifically, KPC1 SEQ ID. No. 4, or p50 SEQ ID No. 3, which form a part of the invention also refers to homologs (e.g., polypeptides), which are at least about 50%, at least about 55%, at least about 60%, at least about 65%, at least about 70%, at least about 75%, at least about 80%, at least about 85%, at least about 87%, at least about 89%, at least about 91%, at least about 93%, at least about 95%, at least about 97% or more, homologous to the KPC1 sequence as set forth in SEQ ID No. 4 or homologous to the p50 sequence as set forth in SEQ ID No. 3 listed herein, as determined using any appropriate means, including BlastP software of the National Center of Biotechnology Information (NCBI) using default parameters). The homolog may also refer to a deletion, insertion, or substitution variant, including an amino acid substitution, thereof and biologically active polypeptide fragments thereof.

As used herein the term "about" refers to ±10%.

As used herein, in one embodiment, the term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NH-G(Sc)—C(0)-Q or —OC(0)G(Sc)-Q, wherein Q is —SR, —NRR or alkoxyl, R is hydrogen or alkyl, Sc is a side chain of a naturally occurring or non-naturally occurring amino acid and G is C1-C2 alkyl. In certain embodiments, G is Ci alkyl and Sc is selected from the group consisting of hydrogen, alkyl, heteroalkyl, arylalkyl and heteroarylalkyl.

As used herein, in one embodiment, the term "peptide" may be derived from a natural biological source, synthesized, or produced by recombinant technology. It may be generated in any manner, including by chemical synthesis. One or more of the amino acids may be modified, for example, by the addition of a chemical entity such as a carbohydrate group, a phosphate group, a farnesyl group, an isofarnesyt group, a fatty acid group, an acyl group (e.g., acetyl group), a linker for conjugation, functionalization, or other known protecting/blocking groups.

As used herein, in one embodiment, the term "peptide," may be fragments, derivatives, analogs, or variants of the foregoing peptides, and any combination thereof. Fragments of peptides, as that term or phrase is used herein, include proteolytic fragments, as well as deletion fragments. Variants of peptides include fragments and peptides with altered amino acid sequences due to amino acid substitutions, deletions, or insertions.

Variants may occur naturally or be non-naturally occurring. Examples include fusion proteins, peptides having one or more residues chemically derivatized by reaction of a functional side group, and peptides that contain one or more naturally occurring amino acid derivatives of the twenty standard amino acids. These modifications may also include the incorporation of D-amino acids, or other non-encoded amino-acids. In one embodiment, none of the modifications should substantially interfere with the desired biological activity of the peptide, fragment thereof. In another embodiment, modifications may alter a characteristic of the peptide, fragment thereof, for instance stability or half-life, without interfering with the desired biological activity of the peptide, fragment thereof. In one embodiment, as used herein the terms "peptide" and "protein" may be used interchangeably having all the same meanings and qualities.

In one embodiment, peptide of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide of the present invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the peptide of the present invention is retrieved in a substantially pure form.

In one embodiment, the phrase "substantially pure" refers to a purity that allows for the effective use of the protein in the applications described herein.

In one embodiment, the peptide of the present invention can also be synthesized using in vitro expression systems. In one embodiment, in vitro synthesis methods are well known in the art and the components of the system are commercially available.

In one embodiment, production of a peptide of this invention is using recombinant DNA technology. A "recombinant" peptide, or protein refers to a peptide, or protein produced by recombinant DNA techniques; i.e., produced from cells transformed by an exogenous DNA construct encoding the desired peptide or protein.

In some embodiments, the recombinant peptides, fragments thereof or peptides are synthesized and purified; their therapeutic efficacy can be assayed either in vivo or in vitro. In one embodiment, the activities of the recombinant fragments or peptides of the present invention can be ascertained using various assays including cell viability, survival of transgenic mice, and expression of megakaryocytic and lymphoid RNA markers.

In one embodiment, a peptide of this invention comprises at least 3 amino acids. In another embodiment, a peptide comprises at least 5 amino acids. In another embodiment, a peptide comprises at least 10 amino acids. In another embodiment, a peptide comprises at least 20 amino acids. In another embodiment, a peptide comprises at least 25 amino acids. In other embodiments, a peptide comprises at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists essentially of at least 5 amino acids. In another embodiment, a peptide consists essentially of at least 10 amino acids. In other embodiments, a peptide consists essentially of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids. In one embodiment, a peptide of this invention consists of at least 5 amino acids. In another embodiment, a peptide consists of at least 10 amino acids. In other embodiments, a peptide consists of at least 30 amino acids or at least 50 amino acids or 75 amino acids, or 100 amino acids, or 125 amino acids, or 150 amino acids, or 200 amino acids, or 250 amino acids or 300 amino acids or 350 amino acids or 400 amino acids.

As used herein, in one embodiment, the terms "peptide" and "fragment" may be used interchangeably having all the same meanings and qualities. As used herein in, in one embodiment the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylalanine (Nol), ring-methylated derivatives of Phe, halogenated derivatives of Phe or o-methyl-Tyr.

As used herein, in one embodiment the term "amino acid" refers to naturally occurring and synthetic α, βγ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. As used herein, in one embodiment the phrase "Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art. Guidance concerning which amino acid changes are likely to be phenotypically silent can also be found in Bowie et al., 1990, Science 247: 1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine (S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

As used herein a "pharmaceutical composition" refers to a preparation of one or more of the active ingredients described herein with other chemical components such as physiologically or pharmaceutically suitable carriers and excipients. The purpose of a pharmaceutical composition is to facilitate administration of a compound to an organism.

Further included are constructs which include nucleic acid encoding the same the proteins of the invention.

Hereinafter, the phrases "physiologically acceptable carrier" and "pharmaceutically acceptable carrier", which may be interchangeably used, refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

In some embodiments, the invention further envisages inclusion of the proteins of the invention sequence or a fused protein thereof in a complex where it is attached to proteinaceous (e.g., heterologous amino acid sequence) or non-proteinaceous moieties (e.g., PEG), each of which being capable of prolonging the half-life of the composition while in circulation.

Such a molecule is highly stable (resistant to in-vivo proteaolytic activity, probably due to steric hindrance conferred by the non-proteinaceous moiety) and may be produced using common solid phase synthesis. Further recombinant techniques may still be used, whereby the recombinant peptide product is subjected to in-vitro modification (e.g., PEGylation as further described herein below).

The phrase "non-proteinaceous moiety" as used herein refers to a molecule not including peptide bonded amino acids that is attached to the above-described KPC1 or p50 amino acid sequence. According to some embodiments, the non-proteinaceous moiety may be a polymer or a co-polymer (synthetic or natural). Non-limiting examples of the non-proteinaceous moiety of the present invention include polyethylene glycol (PEG) or derivative thereof, Polyvinyl pyrrolidone (PVP), albumin, divinyl ether and maleic anhydride copolymer (DIVEMA); polysialic acid (PSA) and/or poly(styrene comaleic anhydride) (SMA). Additionally, complexes which can protect KPC1 or p50 from the environment and thus keep its stability may be used, including, for example, liposomes or micelles containing the active ingredient of the invention or a fused protein comprising thereof are also included in the invention.

According to some embodiments of the invention, the active ingredient of the invention or the fused protein comprising the active ingredient of the invention is attached to a non-proteinaceous moiety, which may act as a sustained-release enhancing agent. Exemplary sustained-release enhancing agents include, but are not limited to hyaluronic acid (HA), alginic acid (AA), polyhydroxyethyl methacrylate (Poly-HEMA), glyme and polyisopropylacrylamide.

Attaching the amino acid sequence component of the active ingredient of the invention or the fused protein comprising thereof of the invention to other non-amino acid agents may be by covalent linking or by non-covalent complexion, for example, by complexion to a hydrophobic polymer, which can be degraded or cleaved producing a compound capable of sustained release; by entrapping the amino acid part of the active ingredient of the invention or the fused protein comprising thereof in liposomes or micelles to produce a complex comprising the active ingredient of the invention or the fused protein comprising the same. The association may be by the entrapment of the amino acid sequence within the other component (liposome, micelle) or the impregnation of the amino acid sequence within a polymer to produce the final peptide of the invention.

In some embodiments, the PEG derivative is N-hydroxysuccinimide (NHS) esters of PEG carboxylic acids, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldiimidazole-activated PEGs, PEG-thiol, PEG-maleimide. PEG-maleimide, PEG-vinylsulfone (VS), PEG-acrylate (AC) or PEG-orthopyridyl disulfide may be also used.

The non-proteinaceous moiety may be attached to the active ingredient of the invention amino acid sequence in any chosen position, provided that the therapeutic activity of the proteins of the invention (which may be in some embodiments KPC1 or p50) is retained.

In some embodiments, the conjugated active ingredient of the invention molecules are separated, purified and qualified using e.g., high-performance liquid chromatography (HPLC).

Molecules of this aspect of the present invention may be biochemically synthesized such as by using standard solid phase techniques. These methods include exclusive solid phase synthesis, partial solid phase synthesis methods, fragment condensation and classical solution synthesis.

Solid phase peptide synthesis procedures are well known in the art and further described by John Morrow Stewart and Janis Dillaha Young, Solid Phase Peptide Syntheses (2nd Ed., Pierce Chemical Company, 1984).

In instances where large amounts of the peptides of the present invention are desired, they may be produced using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988&, Methods for Plant Molecular Biology, Academic Press, NY, Section VIII, pp 421-463.

In some embodiments of the invention, there is provided a fused protein that comprises KPC1 or p50 as defined herein together with one or more molecule which extend the half life of KPC1 or p50 in the plasma. In some embodiments, the fused protein further comprises a linker. In some embodiments of the invention, there is provided a fused protein that comprises KPC1 or p50 as defined herein and a protein that stabilizes KPC1 or p50 as defined herein or protect it in the blood stream or at the tissue. In some embodiments the fused protein comprises KPC1 or p50 as defined herein attached to a heterologous amino acid sequence. In some embodiments, the heterologous amino acid sequence comprises an immunoglobulin amino acid sequence.

In some embodiments of the invention, there is provided a fused protein that comprises KPC1 or p50 as defined herein and IgG. The IgG may any subclasses or isotypes thereof, e.g., IgG1, IgG2, IgG3, IgG4. In some embodiments any other immunoglobulin region may be used.

In some embodiments, the term "antibody" refers to the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In each pair, the light and heavy chain variable regions (VL and VH) are together responsible for binding to an antigen, and the constant regions (CL, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains VH, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to VH, Cγ1, Cγ2, Cγ3, VL, CL, Fab and Fc fragments.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

In some embodiments, a construct which includes a nucleic acid sequence for KMPC1 as defined herein, for example, SEQ ID. No. 5, and a nucleic acid sequence for IgG may be used in the construct. In some embodiments of the invention, the KPC1 or p50 as defined herein and the IgG are directly fused to each other.

Serum albumin can also be engaged in half-life extension through modules with the capacity to non-covalently interact with albumin. In these approaches, an albumin-binding moiety is either conjugated or genetically fused to the therapeutic protein Proteins with albumin-binding activity are known from certain bacteria. For example, streptococcal protein G contains several small albumin-binding domains (ABD) composed of roughly 50 amino acid residues (6 kDa). Fusion of an ABD to a protein results in a strongly extended half-life (see Roland E Kontermann, strategies for extended serum half-life of protein therapeutics, Current Opinion in Biotechnology 2011, 22:868-876.

Furthermore, the present invention encompasses nucleic acids encoding the fusion proteins described herein. In addition, vectors comprising these nucleic acids and cells transformed with theses vectors are encompassed by the present invention.

Briefly, the fused protein is prepared as follows: an expression construct (i.e., expression vector), which includes an isolated polynucleotide (i.e., isolated from a naturally occurring source thereof that comprises a nucleic acid sequence encoding the KPC1 or p50 as defined herein amino acid sequence fused (optionally including a linker) in frame to a nucleic acid sequence encoding the IgG amino acid sequence e.g., AB776838 (for human, NCBI database) or DQ38154 (for mouse, NCBI database), positioned under the transcriptional control of a regulatory element, such as a promoter, is introduced into host cells.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local, rather than systemic, manner, for example, via injection of the pharmaceutical composition directly into a specific tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with fillers such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

According to some embodiments of the invention, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (angiogenesis related disease or cancer) or prolong the survival of the subject being treated.

Determination of a therapeutically effective amount is well within the capability of those skilled in the art, and depends on the severity of the disease, its type, the mode of administration and the like.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The invention is further related to the treatment of diseases that are associated or augmented by inflammation, bacterial translocation and or gut flora derangement, such as, for example, without being limited, chronic liver diseases and Alzheimer disease, hepatic encephalopathy, ADHD, metabolic syndrome, diabetes both type 1 and type 2, atherosclerosis or chronic fatigue syndrome, NASH, obesity, hepatic encephalopathy and potentially several immune mediated disorders among them Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

In some embodiments of the invention, as can be seen from Examples, the inflammation is related to gastrointestinal inflammation, such as, inflammatory bowel disease (IBD), ulcerative colitis (UC) or Crohn's disease (CD).

In some embodiments of the invention, there is provided a method for producing p50 comprising contacting a cell culture preparation which expresses p105 with KPC1, a peptide which is at least about 70% homologous to the KPC1 sequence as set forth in SEQ ID No. 4 or an agent which up-regulates KPC1, thereby producing p50. In some embodiments, the cells are cells that secrete the p105 into the medium.

In some embodiments of the invention, there is provided a method for screening a potential cancer therapeutic, comprising:

(i) contacting p105 with KPC1 under conditions where p105 is cleaved to p50 by KPC; (ii) contacting p105 with KPC1 and with a test compound suspected of being a cancer therapeutic under conditions where p105 is cleaved to p50 by KPC1;

(iii) measuring the amount of p105 cleaved to p50 by KPC1 in the presence and in the absence and the test compound; and (iv) comparing the amount of p105 cleaved to p50 by KPC1 in the presence and in the absence and the test compound, wherein an increase in cleavage in the presence of the test compound is indicative of a cancer therapeutic.

In some embodiments, the test compound act synergistically with KPC1.

EXAMPLES

Experimental Procedures

Materials, Plasmids, Expressed Proteins, and Cells

All materials (including plasmids and their construction, expression of proteins and their purification, and cultured cells and their manipulation), are described under Supplemental Information.

Preparation and Fractionation of Crude Reticulocyte Lysate

Reticulocytes were induced in rabbits and lysates were prepared and fractionated over DEAE cellulose to Fraction I (unabsorbed material) and Fraction II (high salt eluate) as described (Hershko, A., Heller, H., Elias, S., and Ciechanover, A. (1983). Components of ubiquitin-protein ligase system. Resolution, affinity purification, and role in protein breakdown. J. Biol. Chem. 258, 8206-8214). Fraction II (~200 mg) was further resolved using different successive chromatographic methods as described under Supplemental Information.

In Vitro Translation p105 or p100 were translated in vitro in the presence of L-[$^{35}$S]methionine using the TNT® T7 Quick reticulocyte lysate-based coupled transcription-translation kit according to the manufacturer's instructions.

In Vitro Conjugation and Processing of p105

Ub conjugation and processing of $^{35}$S-labeled p105 were carried out in a reconstituted cell free system containing crude Fraction II as described (Kravtsova-Ivantsiv, Y., Cohen, S., and Ciechanover, A. (2009). Modification by single ubiquitin moieties rather than polyubiquitination is sufficient for proteasomal processing of the p105 NF-kappaB precursor. Mol. Cell 33, 496-504). For conjugation, 1 μg of purified Kpc1-FLAG-TEV-6×HIS, Kpc1I1256A-FLAG-TEV-6×HIS, or 6×His-KPC2 were added as indicated, instead of Fraction II.

Ub Conjugates in Cells

HEK293 cells were transfected with control siRNA or siRNA against KPC1 as described herein. After 24 hr, the cells were transfected with cDNAs coding for FLAG-p105 proteins along with cDNAs coding for HA-Ub and Myc-KPC1, or with an empty vector. After additional 24 hr, the proteasome inhibitor MG132 (20 µM) was added for 3 hr, and the cells were lysed with RIPA buffer supplemented with freshly dissolved iodoacetamide and N-ethylmaleimide (5 mM each) to inhibit deubiquitinating enzymes. p105 (both free and ubiquitinated) and free p50 were immunoprecipitated with immobilized anti-FLAG. The beads were washed five times with RIPA buffer and proteins were resolved by SDS-PAGE. Free and conjugated p105 (and free p50) were visualized using anti-FLAG.

Tumorigenicity

Cell-based (soft agar) and animal (mice xenografts) tumorigenicity assays are described under Supplemental Information.

RNASeq Analysis

RNA from U87-MG xenografts was isolated using RNA purification kit and analyzed using the Illumina HiSeq 2500 analyzer. Identification and clustering of the human genes are described under Supplemental Information.

Immunohistochemistry and Statistical Analysis

The staining technique and statistical analysis of the staining data of SCCHN, breast cancer and glioblastoma were performed as described under Supplemental Information.

Supplemental Information

Extended Experimental Procedures

Materials

Materials for SDS-PAGE and Bradford reagent were from Bio-Rad. L-[$^{35}$S]methionine and pre-stained MW markers were from GE Healthcare. Tissue culture sera, media, and supplements, were from Sigma or from Biological Industries [Bet HaEmek, Israel; except for the FCS used for growing Sf9 cells that was from Hyclone, and Iscove's Modified Dulbecco's Medium (IMDM) for growing HAP1 cells that was from Gibco®]. HAP1 control cells (Carette et al., 2011) and HAP1 cells knocked out for KPC1 [1 bp insertion (nucleotide is underlined and bolded) in exon 4 (NM_022064; 192-CCAGAACATTTGGACCAGTT GGCTACAGGTGGACAATGAGG-232 (SEQ ID No. 8); the insertion results in a frameshift] or KPC2 [1 bp insertion (nucleotide is underlined and bolded) in exon 2 (NM_016172; 210-GTGCTGAGT GATGCCAGGAC ACATCCTGGAAGAGAACATCC-250 (SEQ ID No. 9); the insertion results in a frameshift] were generated by Haplogen Genomics GmbH (Vienna, Austria), using the Crispr-CAS technology. Collagenase I was from Sigma and Dispase II from Roche. Free and immobilized mouse anti-FLAG (M2), rabbit anti-p50 Prestige Antibodies® (for immunoprecipitation and Western blot), and FLAG® peptide, were from Sigma. Mouse anti-HA (16B12) was from Covance, and rabbit anti-p50 (NLS) and its blocking peptide, mouse anti-KPC1 (267.1 for Western blot), anti-p65 (A), anti-p27 (C-19) and anti-GFAP (H-50), were from Santa Cruz. Anti-KPC1 (ab57549 for immunohistochemistry and for Western blot) was from Abcam, whereas anti-cleaved caspase 3 (D175) was from Cell Signaling. Anti-ki-67 (MIB-1) was from DAKO, and anti-actin was from Millipore. Peroxidase-conjugated (for Western blotting) and Rhodamine Red™-X-conjugated goat anti-rabbit (for immunofluorescence) secondary antibody were from Jackson ImmunoResearch Laboratories. VECTASHIELD® Mounting Medium with DAPI was from Vector Laboratories. Secondary HRP-conjugated antibody HISTOFINE® Simple Stain™, Max Po Universal Immuno Peroxidase Polymer anti-rabbit/anti-mouse, and HISTOFINE® Simple Stain™ AEC solution for immunohistochemistry, were from Nichirei Biosciences. Ubiquitin, dithiothreitol (DTT), phosphocreatine, creatine phosphokinase, adenosine 5'-triphosphate (ATP), adenosine 5'-[γ-thiotriphosphate] (ATPγ S), iodoacetamide, N-ethylmaleimide, Tris and HEPES buffers, paraformaldehyde, crystal violet, and O-nitrophenyl-beta-D-galactopyranoside (ONPG), were from Sigma. Protease inhibitors mixture and N-carbobenzoxy-L-leucyl-L-leucyl-leucinal (MG132) were from Calbiochem. Ub aldehyde (UbA1) was from BIOMOL. Reagents for enhanced chemiluminescence (ECL) were from Pierce. TNT® T7 Quick reticulocyte lysate-based coupled transcription/translation kit and the luciferase reporter 1000 assay system were from Promega. JetPEI™ cell transfection reagent was from Polyplus. Lipofectamine® RNAiMAX and Lipofectamine® 2000 transfection reagents for siRNA and for DNA transfection, respectively, and Bac-to-Bac® baculovirus expression system, were from Invitrogen. siRNAs were synthesized by Dharmacon. shRNAs, RevertAid H Minus First Strand cDNA Synthesis Kit, Shandon Immune-Mount™, and LightShift® Chemiluminescent ElectroMobility Shift Assay (EMSA) kit, were from Thermo Scientific. TaqMan Fast Universal PCR Master Mix and TaqMan Gene Expression Assay were from Applied Biosystems. Restriction and modifying enzymes were from New England Biolabs. Oligonucleotides were synthesized by Syntezza Bioscience or by Sigma. All the chromatographic columns were purchased from GE Healthcare except for the hydroxyapatite column that was from BioRad. Low Melt Agarose and mini-PROTEAN® TBE precast gel (5%, for separation of dsDNA) were from Bio-Rad. DEAE cellulose was purchased from Whatman. Ni-NTA resin was from QIAGEN. Glioblastoma and breast tissue microarrays were from US Biomax, Inc. NucleoSpin® Kit for RNA purification was from Macherey-Nagel. All other reagents were of high analytical grade.

Plasmid Construction cDNAs coding for human p105 and p105S927A for in vitro translation (in pT7β-6×HIS) and transient transfection in cells (in pFLAG-CMV2), were described previously (Cohen, S., Achbert-Weiner, H., and Ciechanover, A. (2004). Dual effects of IkappaB kinase beta-mediated phosphorylation on p105 Fate: SCF(beta-TrCP)-dependent degradation and SCF(beta-TrCP)-independent processing. Mol. Cell Biol. 24, 475-486; Cohen, S., Lahav-Baratz, S., and Ciechanover, A. (2006). Two distinct ubiquitin-dependent mechanisms are involved in NF-kappaB p105 proteolysis. Biochem. Biophys. Res. Commun. 345, 7-13). For in vitro translation of deleted species of p105 (p105Δ500-600, p105Δ565-660, p105Δ647-758, p105Δ752-794, p105Δ544-803), the corresponding cDNAs were generated by PCR and cloned into the pT7β-6×HIS BamHI and EcoRI restriction sites. For transient transfection of the deleted species of p105 in cells, the cDNA fragments with the deletions that were cloned initially into pT7β-6×HIS, were sub-cloned into the PstI restriction site in pFLAG-CMV2p105 or pFLAG-CMV2p105S927A. FLAG-p105K594,625,630,637,639, 640,684,740R (FLAG-p105K8R; where all the lysine residues in the ankyrin repeats and in between them were substituted with arginines) in pFLAG-CMV2, was generated by site-directed mutagenesis. FLAG-p105Δ574-803 (in which all but one of the ankyrin repeats were deleted) was generated by PCR and was cloned into the pFLAG-CMV2 NotI restriction site. cDNA coding for p100 was amplified with primers flanked with HindIII and BamHI restriction sites, and was cloned into pFLAG-CMV2.

cDNAs coding for human p105K46-58R, p105Δ429-654, and p105Δ429-654;K29,K46-58R for in vitro translation (in pT7β-6×HIS), and p105Δ429-654 and p105Δ429-654;K29, K46-58R for transient transfection (in pFLAG-CMV2), were described previously (Cohen, S., Achbert-Weiner, H., and Ciechanover, A. (2004). Dual effects of IkappaB kinase beta-mediated phosphorylation on p105 Fate: SCF(beta-TrCP)-dependent degradation and SCF(beta-TrCP)-independent processing. Mol. Cell Biol. 24, 475-486; Cohen, S., Lahav-Baratz, S., and Ciechanover, A. (2006). Two distinct ubiquitin-dependent mechanisms are involved in NF-kappaB p105 proteolysis. Biochem. Biophys. Res. Commun. 345, 7-13). The cDNA coding for p105K46-58R was amplified (using pT7βp105K46-58R as a template) with primers flanked with NotI restriction site, and was cloned into pFLAG-CMV2.

cDNAs coding for HA-Ub, Myc-KPC1, and Myc-KPC1I1256A for expression in mammalian cells sub-cloned into pCAGGS (Niwa, H., Yamamura, K., and Miyazaki, J. (1991). Efficient selection for high-expression transfectants with a novel eukaryotic vector. Gene 108, 193-199), were provided by Dr. Kazuhiro Iwai.

KPC1-FLAG-TEV-6×HIS and KPC1I1256A-FLAG-TEV-6×HIS for expression in insect cells were cloned into pFastBac™ via several steps. Initially, the N-terminal segment of KPC1 was amplified with primers flanked with BsshII and EcoRI, and the C-terminal segment of KPC1 was amplified with primers flanked with EcoRI and SalI. The two fragments were sub-cloned into the appropriate restriction sites of pFastBac™. Finally, FLAG-TEV-6×HIS was introduced into pFastBac™ using the SalI restriction site.

cDNA coding for KPC2 for expression in bacterial cells was amplified with primers flanked with EcoRI and HindIII restriction sites, and was sub-cloned into pT73-6×HIS.

cDNAs coding for FLAG-IKKβ and the constitutively active FLAG-IKKβS176,180E were as described (Mercurio, F., Zhu, H., Murray, B. W., Shevchenko, A., Bennett, B. L., Li, J., Young, D. B., Barbosa, M., Mann, M., Manning, A., and Rao, A. (1997). IKK-1 and IKK-2: cytokine-activated IkappaB kinases essential for NF-kappaB activation. Science 278, 860-866).

cDNA coding for NIK was as described (Senftleben, U., Cao, Y., Xiao, G., Greten, F. R., Krahn, G., Bonizzi, G., Chen, Y., Hu, Y., Fong, A., Sun, S. C., and Karin, M. (2001). Activation by IKKalpha of a second, evolutionary conserved, NF-kappa B signaling pathway. Science 293, 1495-1499).

cDNA coding for 6×HIS-E6-AP was as described (Zaaroor-Regev, D., de Bie, P., Scheffner, M., Noy, T., Shemer, R., Heled, M., Stein, I., Pikarsky, E., and Ciechanover, A. (2010). Regulation of the polycomb protein Ring1B by self-ubiquitination or by E6-AP may have implications to the pathogenesis of Angelman syndrome. Proc. Natl. Acad. Sci USA 107, 6788-6793).

cDNAs coding for Myc-KPC1, Myc-KPC1I1256A, and FLAG-p50 for generation of cells that stably express these proteins, were amplified with primers flanked with XhoI and BamHI or with XhoI, respectively, and were sub-cloned into the NSPI-CMV MCS lentiviral expression vector (Akiri, G., Cherian, M. M., Vijayakumar, S., Liu, G., Bafico, A., and Aaronson, S. A. (2009). Wnt pathway aberrations including autocrine Wnt activation occur at high frequency in human non-small-cell lung carcinoma. Oncogene 28, 2163-2172).

cDNA coding for p65 was amplified with primers flanked with BamHI and was sub-cloned into pT7β-6×HIS BamHI restriction site.

Cultured Cells

HEK293, HeLa, U20S, MDA-MB 231 and U87-MG were grown at 37° C. in DMEM supplemented with 10% fetal calf serum and antibiotics (penicillin-streptomycin). Sf9 cells were grown in Grace's medium supplemented with 10% FCS, penicillin (100 U/ml)/streptomycin (0.1 mg/ml), and yeastolate and lactalbumin (3.332 gr/l each). HAP1 cells were grown in IMDM supplemented with 10% fetal calf serum and antibiotics (penicillin-streptomycin).

Synthesis of p105-Derived Peptides

Synthetic phosphorylated and non-phosphorylated peptides derived from the p105 IKKβ-phosphorylation site (917-DELRDSDSVCDS(P)GVETS(P)FRKLSFTES-942 (SEQ ID No. 10)) were prepared according to Fmoc-solid phase peptide synthesis strategy using HCTU (1-[Bis(dimethylamino)methylen]-5-chlorobenzotriazolium 3-oxide hexafluorophosphate, N,N,N',N'-Tetramethyl-O-(6-chloro-1H-benzotriazol-1-yl)uronium hexafluorophosphate) and DIEA (N-Diisopropylethylamine) as coupling reagents. The synthesis was carried out on a Rink Amide resin using automated peptides synthesizer (CSBIO). Phosphorylated Ser was coupled as Fmoc-Ser(HPO3Bzl)OH. Cleavage of the peptide was performed using a mixture of 85:5:5:2.5:2.5 of TFA:water:thioanisole:phenol:ethanedithiol for 2 hours at room temperature. The peptide was precipitated using cold ether, dissolved in 50% acetonitile in water in the presence of 0.1% TFA. Purification was carried using preparative column (Jupiter 10 micron, C18/C4 300 Å, 250×22.4 mm) and a linear gradient of 5-50% buffer containing 99.9% acetonitrile and 0.1% TFA over 30 min and with a flow rate of 15 ml/min. Fractions were analyzed by mass spectrometry using LCQ Fleet Ion Trap instrument (Thermo Scientific), and the fractions which showed over 85% purity were collected and lyophilized for use in the inhibition assay.

Fractionation of Crude Reticulocyte Lysate

Fraction II (~200 mg) was resolved on a HiLoad™ 16/10 Q Sepharose HP column using a linear salt gradient of 0.0-0.6 M KCl. Fractions that contained p105 Ub-conjugating activity were further resolved on a HiPrep™ Heparin 16/10 FF column, and proteins were eluted using a linear salt gradient of 0.0-1.0 M NaCl. The fractions with the p105 E3 activity were subjected to hydroxyapatite chromatography. Proteins were eluted using a linear gradient of 10-700 mM KPi pH 7.0. The active fractions were applied to a Mono Q 5/50 GL column, and proteins eluted using a linear salt gradient of 0.0-0.6 M KCl. The active fractions were resolved on a gel filtration HiLoad 16/600 Superdex 200 column. Elution was carried out in a buffer containing 20 mM Tris-HCl, pH 7.2, 150 mM NaCl, and 1 mM DTT. The E3 activity was eluted in a peak corresponding to an apparent native molecular size of ~170-300 kDa, and was applied to a HiTrap™ Heparin HP column. Elution was performed with a linear salt gradient of 0.0-1.0 M NaCl. The active fractions from the last three chromatographic steps were analyzed by mass spectrometry as described below.

Mass Spectrometric Analysis

Samples were digested by trypsin, analyzed by LC-MS/MS on Orbitrap XL (Thermo), and identified by Protein Discoverer software version 1.4 against the rabbit section of the Uniprot database. The analysis was done using the Sequest search engine. The data were filtered with 1% FDR and 5 ppm accuracy.

Transient Transfection and Processing of p105 in Cells

HeLa cells were transiently transfected with the various indicated cDNAs using Lipofectamine® 2000 according to the manufacturer's protocol, and HEK293 cells were transiently transfected using the jetPEI™ reagent. 24 hr after transfection, cycloheximide (20 µg/ml) was added for the indicated times, and the cells were harvested and lysed with RIPA buffer [150 mM NaCl, 0.5% sodium deoxycholate, 50 mM Tris-HCl (pH 8.0), 0.1% SDS, and 1% NP-40, supplemented with freshly added protease inhibitors mixture]. Protein aliquots representing an equal number of cells were resolved via SDS-PAGE (10%) and blotted onto nitrocellulose membrane. p105 or its mutant species were visualized using anti-FLAG, and processing was expressed as the ratio between the band density of p50 and the sum of the band densities of p105 and p50, multiplied by 100%, except when indicated otherwise. Actin was used as a loading control and was detected using a specific antibody.

Stable Transfection

For stable transfection, U87-MG, U2OS, and MDA-MB 231 cells were transfected with an empty vector, Myc-KPC1, Myc-KPC1I1256A, FLAG-p50, or with shRNA against p105 (clones IDs V2LHS_201580, V2LHS_201509, and V2LHS_201757) along with Myc-KPC1. Transfection was carried out using a Lentiviral transduction system, and cells were selected using puromycin (5 µg/ml).

siRNA

To silence human KPC1 and KPC2, ON-TARGETplus SMART pool siRNAs synthesized by Dharmacon was used (for KPC1—GCGCUACUAUUGGGAUGAA (SEQ ID No. 11), CAACUGGGCCUUCUCUGAA (SEQ ID No. 12), GCACAUGGCGGACCUCCUA (SEQ ID No. 13), GGUGAAGCUUCUAGGUAUA (SEQ ID No. 14); for KPC2—GCUAAUUGAACACGCAGAA (SEQ ID No. 15), GCACGUAGGUGGCGUUGUU (SEQ ID No. 16), CAGAAUGCCGCGUGCGAGU (SEQ ID No. 17), AGAGAUGAGCUGACGGAAA (SEQ ID No. 18)). Transfection of HEK293 cells with the siRNA oligonucleotides was performed using Lipofectamine® RNAiMAX according to the manufacturer's instructions. Briefly, HEK293 cells were grown to 85% confluence in a medium that was not supplemented with antibiotics. KPC1 or KPC2 siRNAs (40 nM) were added to the medium. The efficiency of gene expression suppression was monitored 48 hr after transfection by Western blot using anti-KPC1 or anti-KPC2.

Protein-Protein Interactions

For analyses of protein-protein interactions, HEK293 cells were transfected with cDNAs coding for FLAG-p105 proteins along with cDNA coding for Myc-KPC1 or with an empty vector. p105 proteins were immunoprecipitated with immobilized anti-FLAG, and following washing of the beads with RIPA buffer, the immunoprecipitated proteins were resolved by SDS-PAGE. p105, p50 and KPC1 were visualized using anti-FLAG or anti-KPC1. For interaction between endogenous proteins, HeLa cells were lysed with RIPA buffer, and p105 was immunoprecipitated with anti-p50. Following washing of the beads with RIPA buffer, the immunoprecipitated proteins were resolved by SDS-PAGE. p105, p50 and KPC1 were visualized using anti-p50 or anti-KPC1.

Protein Expression Using a Baculovirus Expression System

KPC1-FLAG-TEV-6×HIS and KPC1I1256A-FLAG-TEV-6×HIS were cloned into pFastBac™ vector as described above. Recombinant Baculovirus constructs were generated using Bac-to-Bac® expression system. To express the proteins, Sf9 cells were infected with the generated viruses. After 48 hr, cells were harvested and lysed in a buffer that contained 50 mM sodium phosphate buffer (pH 8.0), 600 mM NaCl, 10 mM imidazole, 1% NP40, and protease inhibitor cocktail (EDTA free).

Protein Expression Using a Bacterial Expression System

6×HIS-Ubc5c, and 6×HIS-KPC2 were transformed to Rosetta™ (DE3) pLysS *Escherichia coli* cells (Novagen). The bacteria were grown to 0.7 OD at 37° C., and protein expression was induced with IPTG (0.5 mM). After 4 hr, cells were harvested and lysed by sonication in a buffer that contained 20 mM Tris-HCl (pH 7.6), 100 mM NaCl, 10 mM 3-mercaptoethanol, and protease inhibitor cocktail (EDTA free). 6×HIS-E6-AP was expressed as described (Zaaroor-Regev, D., de Bie, P., Scheffner, M., Noy, T., Shemer, R., Heled, M., Stein, I., Pikarsky, E., and Ciechanover, A. (2010). Regulation of the polycomb protein Ring1B by self-ubiquitination or by E6-AP may have implications to the pathogenesis of Angelman syndrome. Proc. Natl. Acad. Sci USA 107, 6788-6793).

Protein Purification

HIS-tagged proteins were purified under native conditions using Ni-NTA resin according to the manufacturer's instructions.

Colony Formation in Soft Agar 3 ml of DMEM containing 0.5% Low Melt Agarose and 10% fetal calf serum were poured into a 60 mm Petri dish. The layer was covered with $0.7 \times 10^4$ cells suspended in 1.5 ml DMEM that contains 0.3% Low Melt Agarose and 10% fetal calf serum, followed by addition of 2 ml DMEM containing 10% fetal calf serum. Medium was changed every 3 days. After three weeks, colonies were fixed (using 4% PFA), stained (with crystal violet; 0.05%), and counted, using the OpenCFU software for colony counting (opencfu.sourceforge.net).

Tumorigenicity

Exponentially growing U87-MG or MDA-MB 231 cells were stably transfected with an empty vector (V0) or with vectors coding for Myc-KPC1, Myc-KPC1I1256A or FLAG-p50, or Myc-KPC1 along with shRNA to silence p105. Cells were dissociated with trypsin, washed with PBS, and brought to a concentration of $50 \times 10^6$ cells/ml. Cell suspension ($5 \times 10^6/0.1$ ml) was inoculated subcutaneously at the right flank of 7-weeks old Balb/C nude mice (n=7). Xenograft size was determined twice a week by externally measuring the growing tumors in two dimensions using a caliper. Tumor volume (V) was determined by the equation $V = L \times W^2 \times 0.5$, where L is the length and W the width of the xenograft. At the end of the experiment, mice were sacrificed and xenografts were resected, weighed and fixed in formalin. Paraffin-embedded 5 µm sections were stained with antibodies as described above.

Immunohistochemistry

Formalin-fixed, paraffin-embedded, 5 m tissue sections of SCCHN, mice U87-MG xenografts, and glioblastoma and breast cancer tissue microarrays, or HEK293 cultured cells were immunostained for p50, KPC1, ki-67, cleaved caspase 3, anti-p27 and GFAP, as indicated. Immunostaining was performed as following: slides were de-paraffinized and rehydrated, and endogenous peroxidase activity was quenched (for 30 min) by 3% hydrogen peroxide in methanol. Slides were then subjected to antigen retrieval by boiling (for 20 min) in 10 mM citrate buffer, pH 6.0. Slides were incubated with 10% normal goat serum in PBS for 60 min to block nonspecific binding, and were incubated (for 20 hr at 4° C.) with the specific antibody (5 µg/ml) in blocking solution. Slides were then extensively washed with PBS, incubated with a secondary HRP-conjugated antibody for 60 min, and developed using AEC solution for 5 min according to the manufacturer's instructions. Sections were stained with hematoxylin or hematoxylin and eosin, and mounted using the Shandon Immune-Mount™.

Immunofluorescence Staining

U87-MG cells ($5 \times 10^5$) were grown on cover slips for 2 days, washed three times with PBS, and fixed/permeabilized in paraformaldehyde (4% for 20 min at room temperature), followed by incubation in Triton X-100 (0.5% for 1 min). The cover slips were washed three times with PBS, incubated with 10% normal goat serum in PBS for 60 min (to block nonspecific binding), and were incubated (for 24 hr at 4° C.) with the specific antibody (5 µg/ml) in blocking solution. Following extensive washing with PBS, the cover slips were incubated with an appropriate secondary antibody (7 µg/ml) for 60 min, followed by three washes with PBS. They were then stained with 4'-6' diamidino-2-phenylindole (DAPI) in mounting medium. Staining was examined using confocal microscope.

Electrophoretic Mobility Shift Assay (EMSA)

Extracts from U87-MG xenografts were isolated using tissue homogenizer in lysis buffer containing 20 mM HEPES (pH 8.0), 400 mM NaCl, 1 mM EDTA (pH 8.0), 1.5 mM $MgCl_2$, 1 mM DTT and 0.05% NP-40. For studying DNA-protein interaction, the LightShift® Chemiluminescent EMSA kit was used according to the manufacturer's instructions. Briefly, extract (5 ag of protein) was incubated with duplex biotin end-labeled oligonucleotide representing the consensus NF-κB binding site [5'-AGTTGA GGGGACTTTCCCAGGC-biotin-3' (SEQ ID No. 19) (bolded and underlined nucleotides denotes NF-κB binding consensus)], subjected to gel electrophoresis on a native polyacrylamide gel (5%), and transferred to a nylon membrane. The biotin end-labeled DNA was detected using the Streptavidin-Horseradish peroxidase conjugate and a chemiluminescent substrate.

Quantitative Real-Time PCR (qRT-PCR)

RNA from U87-MG xenografts was isolated using an RNA purification kit and converted to cDNA using cDNA Synthesis Kit. The qRT-PCR was carried out using TaqMan Gene Expression Assay. The assay was carried out in triplicates using TaqMan primers for VCAM1, HIC1, CDKN2C, IL-6 and TES genes. HPRT gene was used as a control.

RNASeq Analysis Mapped to the Human Genome

RNA from U87-MG xenografts was isolated using an RNA purification kit, and analyzed using Illumina HiSeq 2500. The number of reads was between 25,949,993 and 39,809,768 per sample. The reads were mapped to the human genome (GRCh37) using Tophat version 2.0.9 (Trapnell, C., Pachter, L., and Salzberg, S. L. (2009). TopHat: discovering splice junctions with RNA-Seq. Bioinformatics 25, 1105-1111). Up to 3 mismatches were allowed per read, with up to 3 mismatches per segment. The-b2-sensitive parameter was set. The unmapped reads were mapped later to the mouse genome as described below. The RNASeq analysis experiment was repeated twice independently for KPC1 and V0 (in each experiment, RNA was pooled from tumors derived from different animals, and different pools were analyzed in duplicate or triplicate) and once for p50 (in duplicate independent pools). Several repeated attempts to extract RNA from the p50-expressing tumors did not yield any results, as the tumors were miniscule.

Only uniquely mapped reads were counted in the analysis, using the HTSeq-count package version 0.5.3p3 with 'intersection-nonempty' mode (Anders, S., Pyl, P. T., and Huber, W. (2014). HTSeq-a Python framework to work with high-throughput sequencing data. Bioinformatics).

The counts normalization and the differential expression analysis were done using the DESeq2 package version 1.2.8 (Love, M. I., Huber, W., and Anders, S. (2014). Moderated estimation of fold change and dispersion for RNA-seq data with DESeq2. Genome Biol. 15, 550).

Computational Methods for Analyses of RNASeq Results

Bonferroni adjusted p-values were calculated for the differentially expressed genes, and adjusted p-values<0.05 were considered as significant.

Consistently up- or down-regulated genes were in the KPC1 and p50 overexpressing tumors, and selected only those that had a log 2 fold-change compared to empty-vector control of 0.7 or higher, or −0.7 or lower, respectively. Correlation was calculated as the Pearson linear correlation coefficient.

DAVID (Dennis, G. Jr., Sherman, B. T., Hosack, D. A., Yang, J., Gao, W., Lane, H. C., and Lempicki, R. A. (2003). DAVID: Database for Annotation, Visualization, and Integrated Discovery. Genome Biol. 4, P3) was used to perform functional enrichment analysis, using the functional annotation clustering tool and default settings on either the 534 up- or 48 down-regulated genes. Annotation clusters were described with selected (most descriptive) annotations, and top selected annotation clusters are presented in FIG. 6B.

Tumor suppressor and proto-oncogene annotations were gathered from the TSGene database (Zhao, M., Sun, J., and Zhao, Z. (2013). TSGene: a web resource for tumor suppressor genes. Nucleic Acids Res. 41, D970-976) and Uni-Prot (UniProt Consortium. (2013). Update on activities at the Universal Protein Resource (UniProt) in 2013. Nucleic Acid Res. 41, D43-47). All gene mappings between datasets were based on Ensembl Gene IDs, and significance of enrichment was calculated using the cumulative hyper geometric probability distribution function which takes into account the total number of genes measured, the number of cancer-related genes, the number of genes significantly up- or down-regulated, and the overlap between those subsets.

Data for Integrative analysis of functional annotation clusters and known functional and physical protein-protein interactions between all consistently up- and down-regulated genes (including NFKB1/p50 and KPC1; FIG. 6D), were obtained from the STRING database (Szklarczyk, D., Franceschini, A., Kuhn, M., Simonovic, M., Roth, A., Minguez, P., Doerks, T., Stark, M., Muller, J., Bork, P., et al. (2011). The STRING database in 2011: functional interaction networks of proteins, globally integrated and scored. Nucleic Acids Res. 39, D561-568). They were combined with interactions between genes and their most enriched annotation cluster from a DAVID analysis on the complete dataset. Details and source code of this integrative network method are provided elsewhere (Mercer, J., Snijder, B., Sacher, R., Burkard, C., Bleck, C. K., Stahlberg, H., Pelkmans, L., and Helenius, A. (2012). RNAi screening reveals proteasome- and Cullin3-dependent stages in vaccinia virus infection. Cell Rep. 2, 1036-1047).

Statistical Analysis of Staining of Cancerous and Normal Tissues for KPC1 and p50

The study included 52 patients with Squamous Cell Carcinoma of Head and Neck (SCCHN) who were diagnosed in the Department of Otolaryngology, Head and Neck Surgery, Carmel Medical Center, Haifa, Israel. The study protocol was approved by the local Institutional Review Board. Archival paraffin-embedded pathological material and surrounding normal tissue was obtained for immunohistochemical staining of KPC1 and p50. Breast cancer tissue arrays contained 85 malignant and 20 non-malignant slices. Glioblastoma tissue array contained 192 samples of glioblastoma and 16 normal brain tissue samples. Specimens were examined by a senior pathologist (I. N.) and were scored according to the intensity of staining (0: none, 1: weak; 2: moderate, 3: strong), and localization (cytoplasm versus nucleus).

The results were evaluated for normality using the Kolmogorov-Smirnov test. Correlations between variables were performed using the Pearson's or the Spearman's coefficients of correlation, for parametric or non-parametric groups, respectively. Matched analysis was done to compare staining of the normal tissue to the malignant one.

Results

Example 1

Identification of KPC1 as the p105 Ub Ligase

Figure 1A:
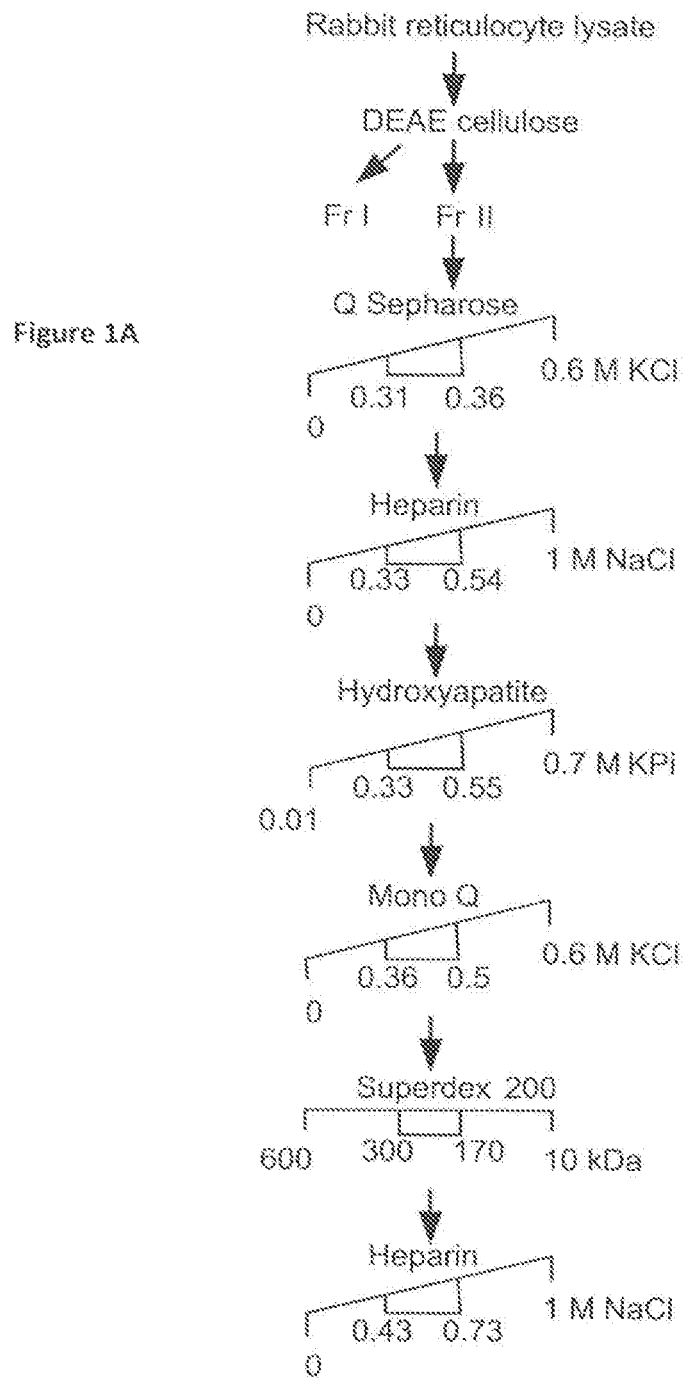
FIG. 1A is a scheme of the chromatographic resolution of Fraction II monitoring the E3 ligating activity towards p105. Numbers represent salt concentrations (M) or molecular weight (kDa) at which the ligating activity was eluted from the respective columns. Fr II denotes Fraction II.
Figure 1B:
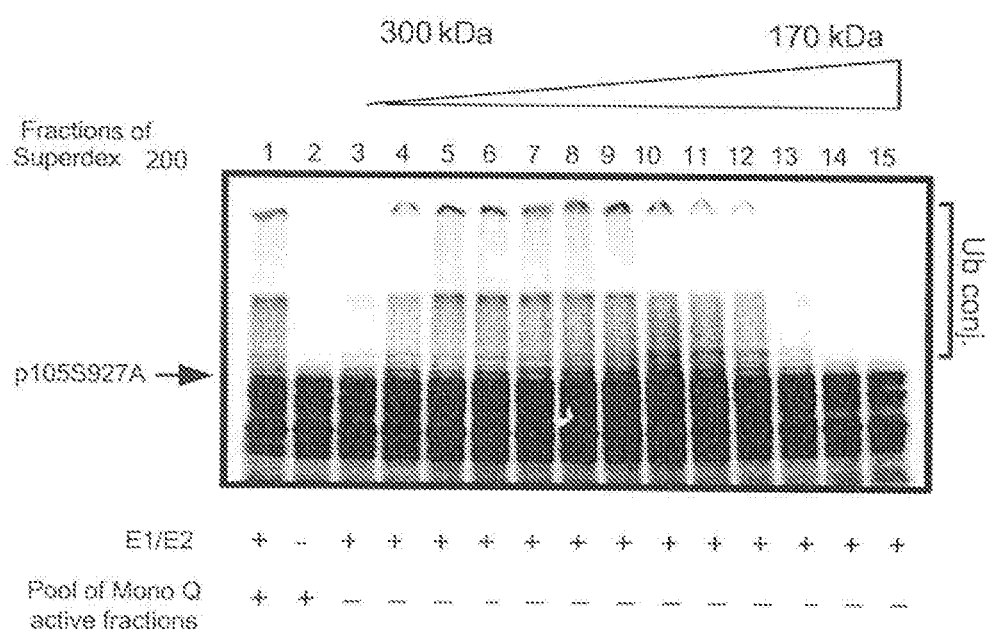
FIG. 1B is a western blot image showing the E3 conjugating activity profile along the fractions resolved by the Superdex 200 gel filtration column. In vitro translated and 35S-labeled p105S927A was ubiquitinated in a reconstituted cell free system in the presence of the resolved fractions.

One of the still missing links in the Ub-mediated activation pathway of NF-κB is the identity of the ligase that ubiquitinates p105, resulting in its proteasomal processing to the p50 active subunit. To identify the ligase, rabbit reticulocyte lysate was fractionated using different chromatographic principles (FIG. 1A). Each fraction along the different steps was monitored for E3 activity in a cell free reconstituted conjugation assay containing in vitro translated 35S-labeled p105 as a substrate (see, for example, FIG. 1B). To avoid ubiquitination by the βTrCP ligase, use was made of a p105S927A mutant that cannot be phosphorylated by IKKβ, and therefore cannot bind this E3. Employing mass spectrometric analysis, peptides derived from the KPC Ub ligase were identified in active fractions along the three last chromatographic steps. In the last step of purification (heparin), 58 KPC1 peptides and 7 KPC2 peptides were identified covering 43.21% and 19.8% of the open reading frame, respectively (FIG. 1C). Because of lack sequence information on rabbit KPC2, the sequence of the mouse protein was used to demonstrate the coverage map. The changes between the two species are negligible (but shown).

To directly test the role of KPC in p105 ubiquitination and processing, a cell free conjugation assay was established using labeled p105 as a substrate and purified KPC1 or its catalytically inactive species (mutated in the RING domain) KPC1I1256A as the ligase. The WT ligase catalyzed conjugation of p105, whereas the inactive ligase did not (FIG. 2A). It appears that KPC1 activity is specific to p105, as it scarcely modifies p100, which is highly homologous to p105 and also undergoes limited proteasomal processing, most probably by a different ligase (FIG. 8A).

To demonstrate the ability of KPC1 to modify p105 in cells, Flag-p105 was overexpressed along with HA-Ub in HEK293 cells, in which KPC1 was either silenced (FIG. 2B, lane 1), or overexpressed (FIG. 2B, lanes 2 and 3). Immunoprecipitation of p105 revealed that it is sparsely ubiquitinated in the absence of the ligase, and ubiquitination is increased significantly following overexpression of KPC1 (FIG. 2B left western blot; IP, compare lanes 1 and 2). Furthermore, it was found that p105 binds to KPC1 and co-immunoprecipitates with it (FIG. 2B right western blot; IP, lane 2). In addition, it was demonstrated that endogenous KPC1 interacts with endogenous p105 (FIG. 8B).

Example 2

KPC1 Promotes Basal and Signal-Induced Processing of p105

To demonstrate the involvement of KPC1 in p105 processing, it's the expression thereof was silenced in cells using small interfering RNA (siRNA). As can be seen in FIG. 2C, the silencing of KPC1 decreased the amount of p50 generated from p105. In a different experiment, FLAG-p105 was expressed in HEK293 cells along with Myc-KPC1 or Myc-KPC1I1256A. Less p50 was generated in the presence of the KPC1 mutant (FIG. 8C).

As noted, processing of p105 occurs also following stimulation. It was further studied whether KPC1 is capable of promoting p105 processing under such conditions as well. Therefore, the generation of p50 from p105 was tested following expression of constitutively active IKKβ (IKKβS176,180E) in the presence (endogenous) or absence (silenced) of KPC1. As presented, the stimulation increased the processing of p105 (compare FIG. 2D to FIG. 2C—control siRNA). Silencing of KPC1 significantly decreased the generation of p50 following stimulation, strongly suggesting a role for KPC1 in signal-induced processing (FIG. 2D). It is known that under the influence of the kinase, the precursor was not only processed but also degraded to a significant extent (compare FIG. 2D to 2C and note in particular the decreasing amount of p105+p50 remained along time following stimulation). It should be noted that the degradation rate of p105 following stimulation was significantly higher in cells that lack KPC1 (FIG. 2D). It is possible that the processing of p105 mediated by KPC1 and its degradation mediated by βTrCP occur in parallel. When one process is inactivated, the other becomes dominant. The influence of KPC1 on signal induced-processing of p105 appears to be specific, as its silencing does not affect the processing of p100 following NF-κB Inducing Kinase (NIK) expression (FIG. 8D).

In all of the described experiments, exogenously expressed p105 was used. To demonstrate the effect on endogenous p105, the human haploid cell line HAP1 was used, in which the single allele of KPC1 or KPC2 were knocked out using the Crispr-CAS technology. Elimination of KPC1 or KPC2 [that stabilizes KPC1 (Hara, T., Kamura, T., Kotoshiba, S., Takahashi, H., Fujiwara, K., Onoyama, I., Shirakawa, M., Mizushima, N., and Nakayama, K. I. (2005). Role of the UBL-UBA protein KPC2 in degradation of p27 at G1 phase of the cell cycle. Mol. Cell Biol. 25, 9292-9303); note that removal of KPC2 results in a significant decrease in the level of KPC1—FIG. 2E] decreased the generation of p50 both in the presence or absence of TNF (FIG. 2E). In contrast, the level of p65 was not affected. The finding that p50 is still present, albeit in a decreased level, in the KPC1 KO cells, may be due to the activity of another, yet to be identified ligase, and/or to cotranslational processing of the nascent peptide that occurs before completion of the p105 precursor synthesis (Lin, L., DeMartino, G. N., and Greene, W. C. (1998). Cotranslational biogenesis of NF-kappaB p50 by the 26S proteasome. Cell 92, 819-828). It should also be noted that the effect of KPC1 on p50 generation is significantly more pronounced in tumors growing in mice than in cultured cells (see below).

The presented finding that KPC1 mediates processing under both basal and stimulated conditions prompted the dissection of the mechanism involved. The interaction between KPC1 and p105 was monitored under basal and stimulated conditions, and it was found that expression of constitutively active IKKβ results in increased interaction between the two as assayed by co-immunoprecipitation (FIGS. 2F and 8E). The finding that the interaction of p105S927A with KPC1 is not affected by IKKβ (FIG. 2F right western blot, lanes 4 and 5) attests to the specificity of the effect of IKKβ in phosphorylating a specific Ser residue (927) in p105. As detailed, it was found that ubiquitination of phosphorylated p105 by KPC1 is stronger compared to that of the non-phosphorylated species (FIG. 8F).

To further confirm that KPC1 interacts more efficiently with phosphorylated p105, an experiment was designed in which the binding of p105 to the ligase with a synthetic phosphorylated peptide derived from the p105 IKKβ-phosphorylation site was compared. The phosphorylated peptide inhibited ubiquitination of p105 by KPC1 to a larger extent compared with its non-phosphorylated species, both in a crude system and in a system made of purified components (FIGS. 2G and 8G, respectively).

Example 3

Role of KPC2 in KPC1-Mediated p105 Ubiquitination and Processing

Further, the role of KPC2, the partner of KPC1 in the heterodimeric ligase complex, in p105 modification and processing was studied. It was noted that its addition to a reconstituted cell free system significantly decreases the ubiquitination of p105 by KPC1 (FIG. 2H). This was true also when p105 was purified by a specific antibody, ruling out a possible effect of other components present in the mixture in which the labeled p105 was translated (FIG. 9A upper western blot). To rule out that the reduced ubiquitination of p105 in the presence of KPC2 is due to a possible deubiquitinating activity of the protein, is was added to the cell free ubiquitination system after KPC1, when most of the ubiquitination reaction was completed. It had no effect on the conjugates pattern (FIG. 9A lower western blot). The interference of KPC2 in chain formation appears to be specific to KPC1 and p105, as it did not affect the ligase activity of E6-AP toward RING1BI53S (Zaaroor-Regev, D., de Bie, P., Scheffner, M., Noy, T., Shemer, R., Heled, M., Stein, I., Pikarsky, E., and Ciechanover, A. (2010). Regulation of the polycomb protein Ring1B by self-ubiquitination or by E6-AP may have implications to the pathogenesis of Angelman syndrome. Proc. Natl. Acad. Sci USA 107, 6788-6793) (FIG. 9B).

Importantly, in correlation with the suppressive effect of KPC2 on KPC1-mediated ubiquitination of p105, silencing of KPC2 increased the formation of p50 (FIG. 2I). That, despite the fact that the short-term silencing reduced partially the level of KPC1 via its effect (or absence thereof) on the stabilization of the ligase (FIG. 2I; note the change in the level of KPC1 following KPC2 silencing).

Example 4

Identification of the Ub Anchoring Sites on p105 Modified by KPC1

It has already been shown that multiple lysines in the C-terminal segment of p105 are required for its ubiquitination and processing (Cohen, S., Achbert-Weiner, H., and Ciechanover, A. (2004). Dual effects of IkappaB kinase beta-mediated phosphorylation on p105 Fate: SCF(beta-TrCP)-dependent degradation and SCF(beta-TrCP)-independent processing. Mol. Cell Biol. 24, 475-486; Kravtsova-Ivantsiv, Y., Cohen, S., and Ciechanover, A. (2009). Modification by single ubiquitin moieties rather than polyubiquitination is sufficient for proteasomal processing of the p105 NF-kappaB precursor. Mol. Cell 33, 496-504) in crude extracts. It was therefore tested whether this was true also for KPC1. Progressive removal of all lysine residues from the C-terminal segment (FIG. 9C) resulted in corollary decrease in conjugation of p105 by KPC1 in a cell free assay (FIG. 2J) and in processing of the precursor in cells (FIG. 9D).

Example 5

The C-Terminal ARs of p105 are Necessary for its Interaction with KPC1 and for its Subsequent Ubiquitination and Processing p105 harbors several domains: REL Homology Domain (RHD), Nuclear Localization Signal (NLS), and a Glycine Rich Repeat (GRR) in its N-terminal segment, and ARs, Death Domain (DD) and a PEST (Proline, Glutamate, Serine and Threonine) sequence in the C-terminal segment (FIG. 3A). It was examined which of those domains is necessary for ubiquitination by KPC1. As can be seen in FIG. 3B, removal of the C-terminal segment abolished altogether conjugation in a cell free system, whereas removal of the N-terminal segment had no effect. Subsequently it was found that removal of all six ARs (p105Δ544-803) affected significantly the ubiquitination of p105 by KPC1 (FIG. 10A, compare lanes 2 and 12). Partial deletion of the repeats affected conjugation only slightly (compare lane 2 to lanes 4, 6, 8, and 10).

Similar results were obtained in experiments carried out in cells. Overexpression of KPC1 increased the ubiquitination of WT p105, but much less so of p105 that lacks all its ARs (FIG. 3C upper western blot; IP, compare lane 4 to lane 3). Importantly, in parallel, a decrease in the interaction between the ARs'-truncated p105 and its ligase compared to WT p105 was also observed (FIG. 3 lower western blot; IP, compare lanes 4 and 3).

To rule out the possibility that the decrease in ubiquitination of p105 that lacks all its ARs is due to removal of the eight lysine residues in the repeats, a mutant p105 was generated in which all those lysines were substituted by arginines. The ubiquitination of the K to R mutant as well as its interaction with KPC1, were similar to that of WT p105 (FIG. 10B upper western blot and middle western blot, respectively). The number of ARs necessary for ubiquitination and processing of p105 was studied. A p105 mutant was constructed where all ARs except one have been deleted (p105Δ574-803). The single remaining AR was sufficient to bind KPC1 and to promote processing similar to that observed for WT p105 (FIG. 3D). Thus it appears that the ARs are redundant with relation to binding of KPC1.

Last, it was studied whether the ARs-dependent ubiquitination increases the processing of p105. As can be seen in FIG. 3E, mutant p105 that lacks all ARs, is processed much less efficiently compared to the WT species and to one lacking only some of the repeats (compare lane 12 to lanes 2, 4, 6, 8, and 10). A similar result was obtained also in cells (FIG. 3F, lanes 1 and 2). Mutant p105 in which all lysine residues in the ARs were substituted with arginines (FLAG-p105K8R), is processed similarly to WT p105 (FIG. 10C, lane 3), strongly suggesting that the ARs are required for the binding, ubiquitination and processing of p105, but do not serve as ubiquitination sites essential for processing.

It appears that the ARs are also involved in signal-induced processing of p105, as their removal significantly decreased IKKβ-mediated generation of p50 (FIG. 3F, compare lane 4 to lane 3). As expected, FLAG-p105S927A and FLAG-p105S927AΔ544-803 did not respond to IKKβ-mediated phosphorylation (FIG. 3F, lanes 7 and 8).

Example 6

Overexpression of KPC1 or p50 Suppresses Tumor Growth

Figure 4A:
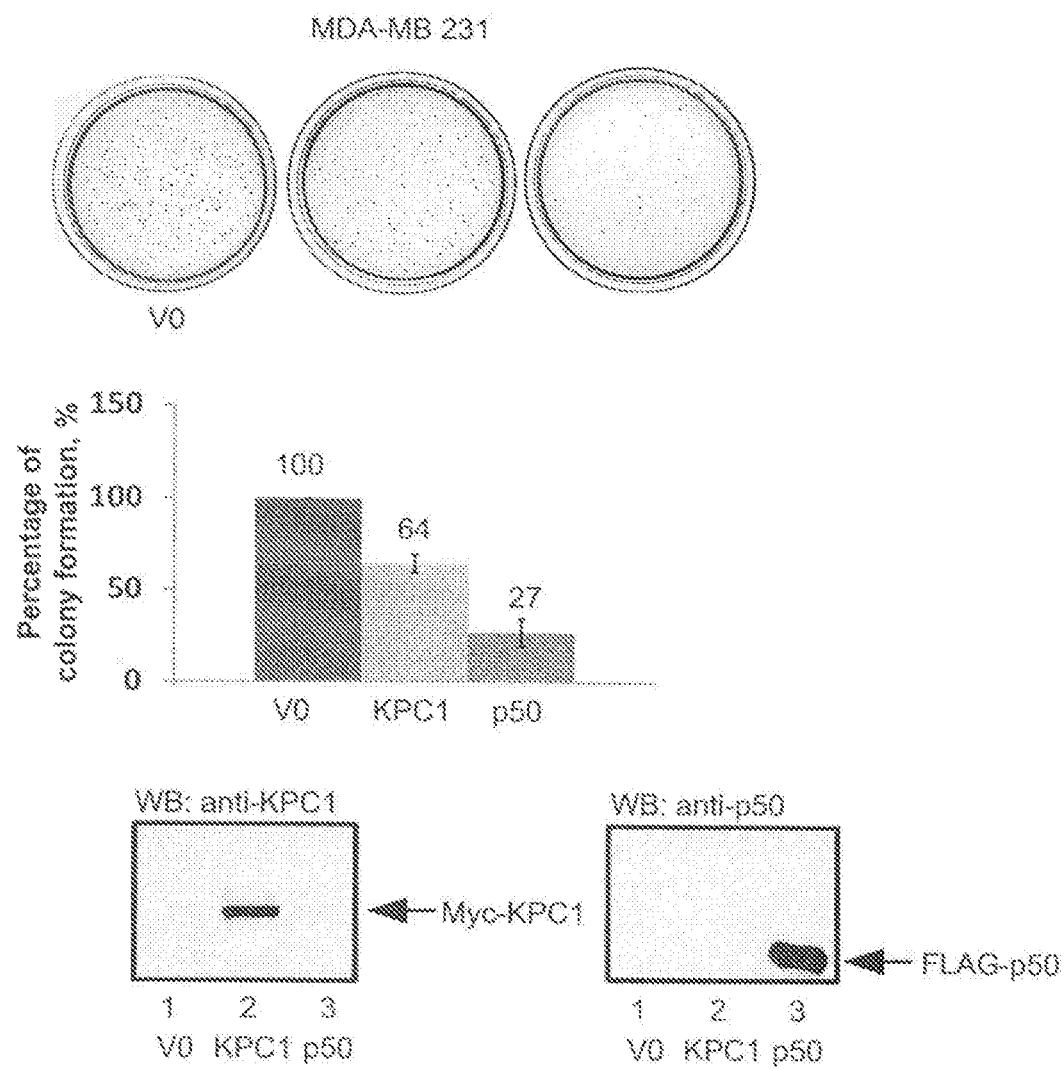
Figure 4B:
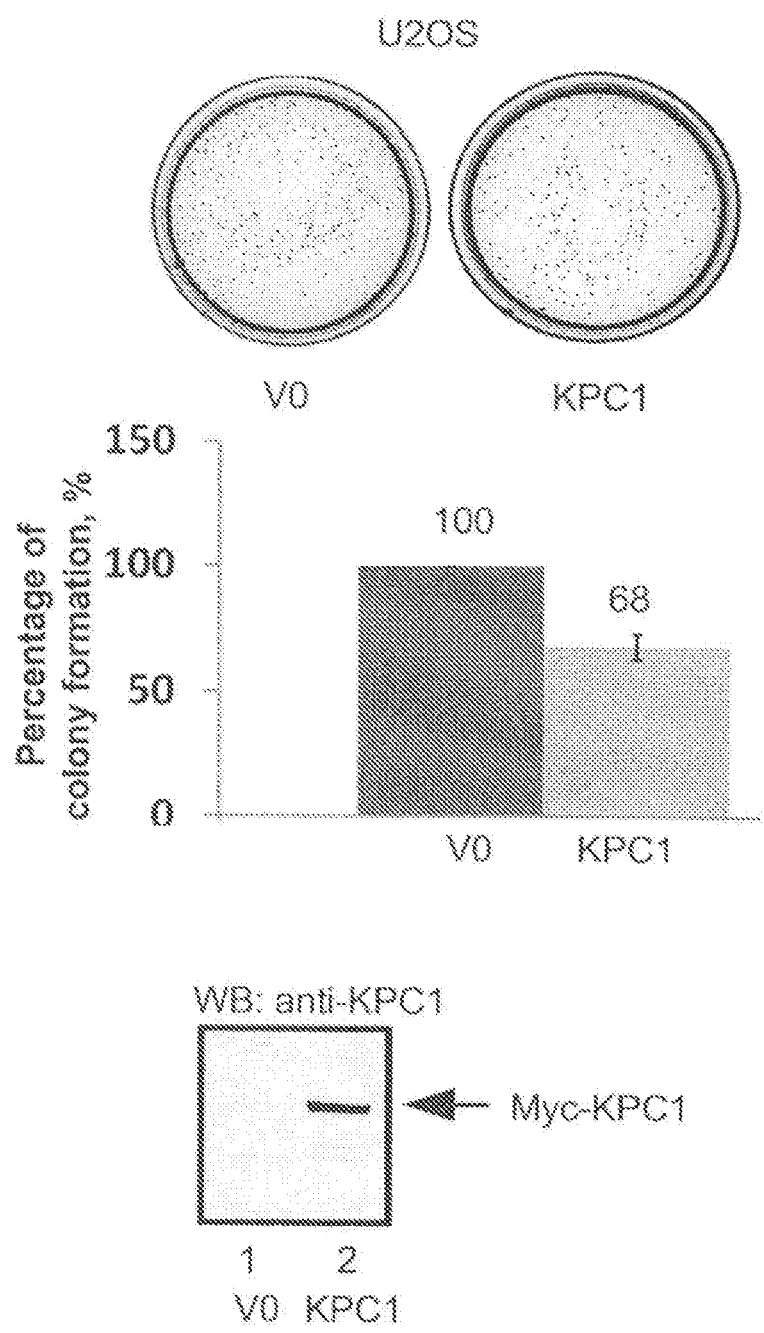
Figure 4C:
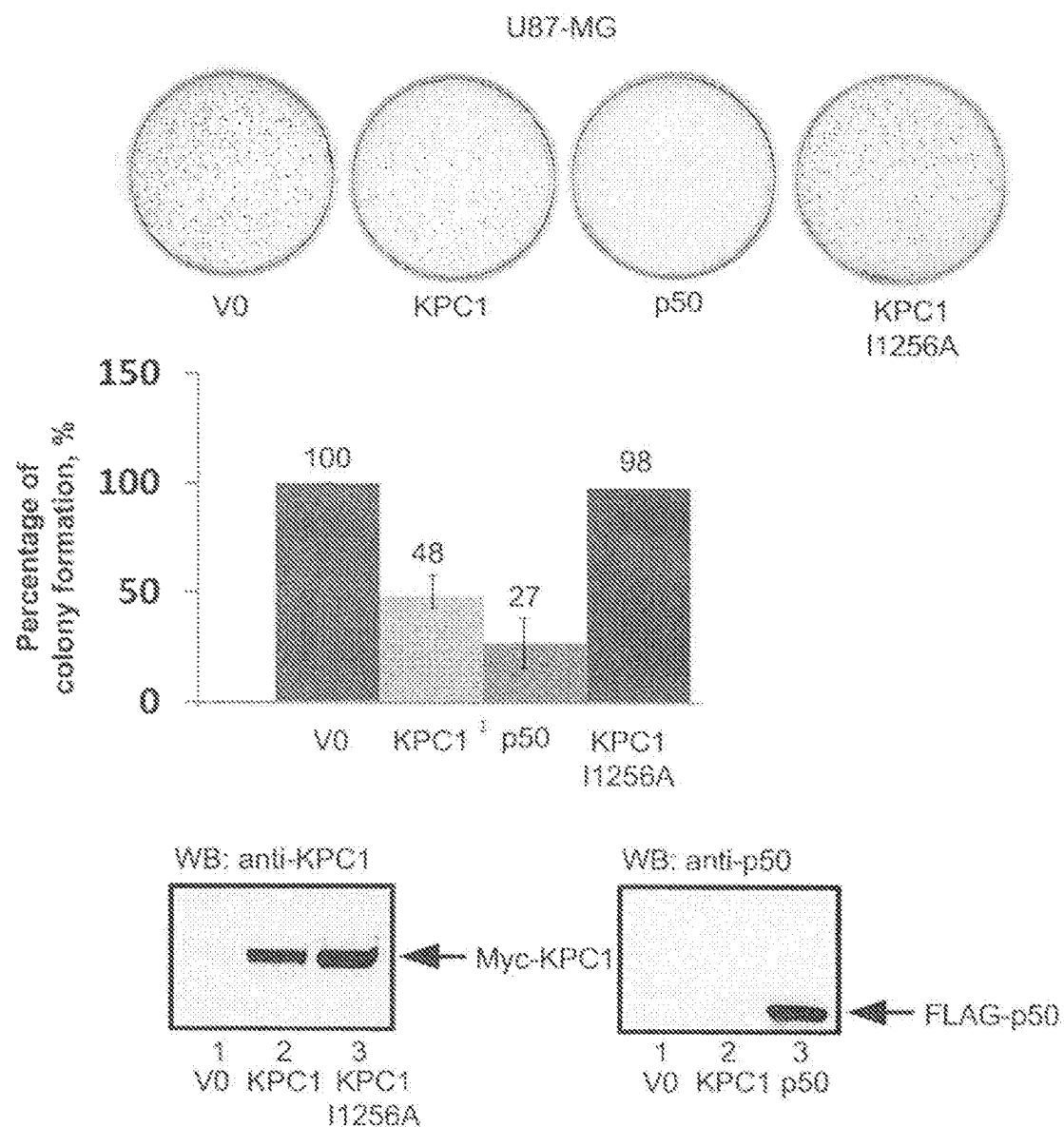
Figure 4D:
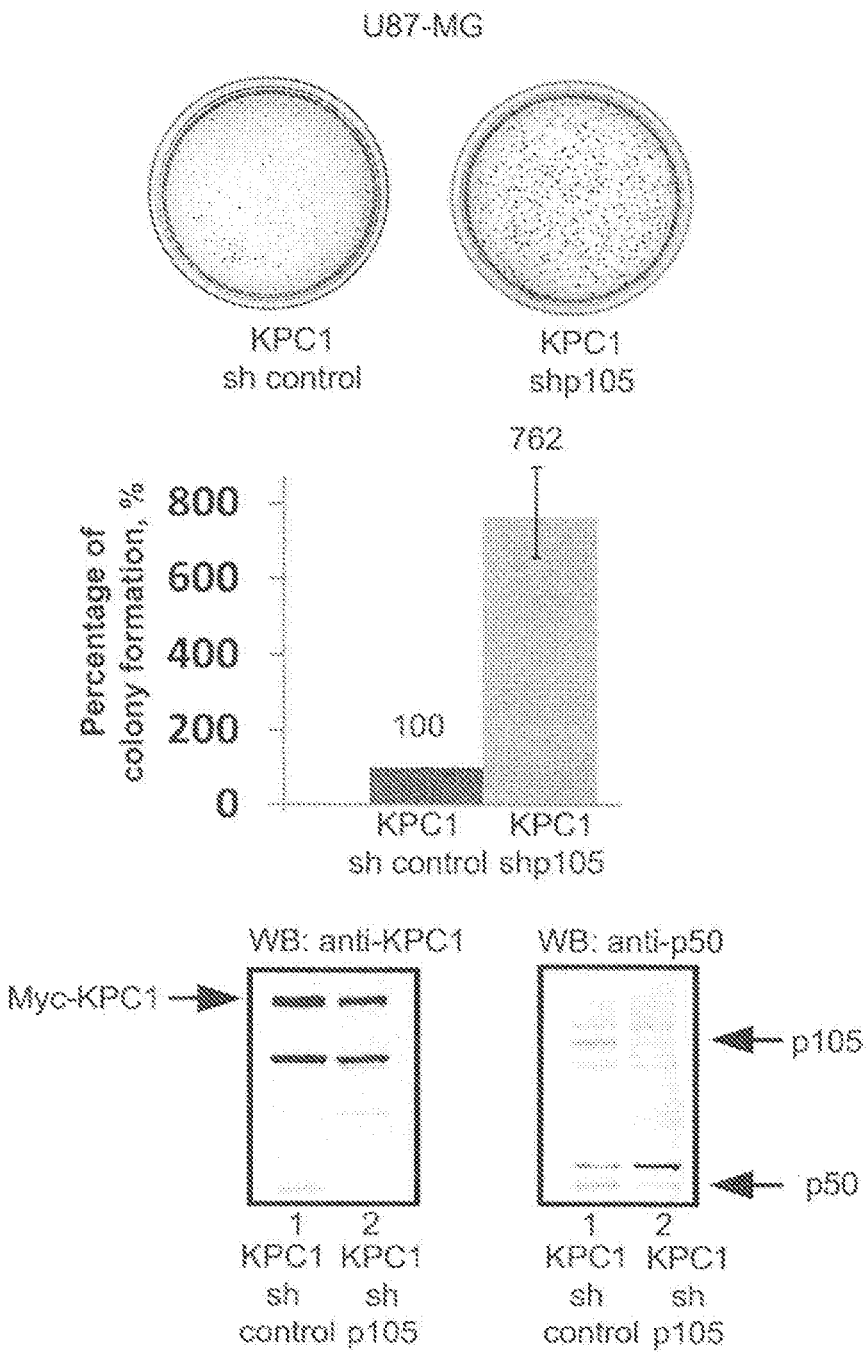

Since NF-κB dimers are known to affect cell survival, proliferation and tumor progression, it was interesting to study the outcome of KPC1 on cell growth. Initially, the influence of overexpressed KPC1 on anchorage-independent growth in MB-MDA 231, U20S and U87-MG cells was monitored and it was found to inhibit colony formation by 36%, 32% and 52%, respectively, compared to controls (FIGS. 4A, 4B and 4C). Importantly, this effect was abrogated in cells overexpressing the inactive ligase species KPC1I1256A, suggesting that the inhibitory effect is due to the ligase activity (FIG. 4C). Cells expressing p50 showed an even stronger inhibition of colony formation (73% for both MB-MDA 231 and U87-MG cells; FIGS. 4A and 4C), strongly suggesting that the effect of the ligase is mediated through its activity on p105, resulting in excessive generation of p50. Supporting the linkage is the finding that silencing of p105 abrogated the strong suppressive effect of KPC1: the number of colonies formed using cells that overexpress KPC1 in the absence of p105 was 7.5-fold larger than that formed in its presence (FIG. 4D). The growth suppressive effect of KPC1 and p50 was studied to see whether it is not due to induction of apoptosis. Thus, U87-MG cells that overexpress those proteins were stained for cleaved caspase 3. As can be seen in FIG. 11, the apoptotic marker could not be detected. For that experiment, it was also demonstrated that the suppressive effect of KPC1 and p50 is not due to some non-specific effect of the over expression of the proteins. The unleashing of growth in the presence of overexpressed KPC1 but in the absence of p105 (FIG. 4D), strongly suggests that the effect of KPC1 is indeed specific.

These observations prompted the study of the effect of KPC1 in a tumor model in mice. Xenografts stably overexpressing V0, KPC1, KPC1I1256A or p50 were generated. Both the growth rate and weights of tumors expressing KPC1 and p50 were significantly smaller compared to those that harbor V0 or KPC1I1256A (FIGS. 5A and 5C for xenografts derived from U87-MG cells, and FIG. 5B for xenografts derived from MDA-MB 231 cells). Importantly, in tumors that overexpress KPC1, the level of p50 is significantly higher compared with tumors that express V0 (FIG. 5D), again suggesting a direct linkage between the KPC1 ligase activity and increased generation of p50. Interestingly, in tumors that overexpress KPC1 or p50, a significant decrease in the level of p65 was also observed (FIG. 5D). This finding raises the possibility that a different NF-κB transcription factor is generated under the influence of KPC1, possibly a p50 homodimer. To demonstrate that there are indeed changes in NF-κB species in human tumor xenografts overexpressing KPC1 and p50, an electrophoretic mobility shift assay (EMSA) was used to monitor the activity of the transcription factor. As can be seen in FIG. 12A, there is significant decrease in the ability of 'canonical' NF-κB to bind its consensus DNA sequence following overexpression of KPC1, and even more so following overexpression of p50.

Of note is that all the effects on tumor growth (reduction in colony formation, tumor growth rate, and weight) were more prominent in p50-expressing tumors than in their KPC1-overexpressing counterparts. This could be explained since p50 is the product of KPC1 activity, and its direct expression has a stronger effect.

The functional linkage between KPC1 and p50 can also be observed in staining of specific proliferation and differentiation markers in the mice-derived tumors. The overexpression of KPC1, but not of KPC1I1256A, results in increased appearance of nuclear NF-κB (FIG. 5E), a significant decrease in the proliferation marker ki-67, and an increase in the glial fibrillary acidic protein (GFAP), a known glial cells differentiation marker. Suspecting that KPC1 stimulates apoptosis, an increase in cleaved caspase 3 was optional; however, there was no change in the levels of the active enzyme compared to control sections. Staining of p27KIP1—a suggested substrate of KPC1 (Kamura, T., Hara, T., Matsumoto, M., Ishida, N., Okumura, F., Hatakeyama, S., Yoshida, M., Nakayama, K., and Nakayama, K. I. (2004). Cytoplasmic ubiquitin ligase KPC regulates proteolysis of p27(Kip1) at G1 phase. Nat. Cell Biol. 6, 1229-1235)—did not show any change in the protein level (FIG. 5E). This may be due to the differences in the systems studied.

Example 7

KPC1 Regulates Expression of a Subset of p50 Target Genes

The profile of gene expression in the tumors using RNASeq analysis of transcripts mapped to the human genome was analyzed (Table S1 and http://www.ncbi.nlm.nih.gov/geo/query/acc.cgi?acc=GSE60530). The altered gene expression patterns revealed a strong similarity between overexpression of p50 and KPC1 in U87-MG xenografts (correlation of 0.51, p-value<10-300; FIG. 6A upper graph), with 48 down- and 534 up-regulated genes which were consistent and significant in all replicates (FIG. 6A lower graph and Table S2). The relative transcript levels of selected genes that were shown to be significantly up- and down-regulated in RNASeq analyses, was corroborated by quantitative real-time PCR (qRT-PCR) (FIG. 12B). Functional analysis revealed highly significant enrichment in glycosylated and extracellular matrix proteins, and up-regulation of genes expressing proteins involved in cell-cell and cell-substrate adhesion, regulation of cell migration, cell junctions, vasculature development, wound healing and cell-cell signaling (FIG. 6B), suggesting a re-establishment of "social" micro-environmental interactions in the p50 and KPC1—overexpressing glioblastoma tumors (Bonavia, R., Inda, M. M., Cavenee, W. K., and Furnari, F. B. (2011). Heterogeneity maintenance in glioblastoma: a social network. Cancer Res. 71, 4055-4060). Down regulated processes included a reduced response to hypoxia required for maintaining glioblastoma stem cells (Heddleston, J. M., Li, Z., McLendon, R. E., Hjelmeland, A. B., and Rich, J. N. (2009). The hypoxic microenvironment maintains glioblastoma stem cells and promotes reprogramming towards a cancer stem cell phenotype. Cell Cycle 8, 3274-3284), as well as reduced positive regulation of cell migration (FIG. 6B). Of the consistently changed genes, 21 are known NF-κB targets (p-value<3.4×10-9; http://www.bu.edu/nf-kb/gene-resources/target-genes/). To further assess if the observed reduction in tumor size was the consequence of a reduction in proto-oncogenes and/or of an increased expression of tumor suppressor genes, gene annotations were gathered from various sources. Enrichment analysis on these gene annotations revealed a significant (p-value<1.4×10-18) increase in the expression of 40 tumor suppressor genes, with no significant change in other classes (FIG. 6C).

Finally, an integration of functional annotation enrichment and protein-protein interactions for the differentially regulated genes was performed, revealing a dense network of up-regulated genes revolved around a few down-regulated ones, such as interleukin-6 (IL-6), interleukin-6 receptor (IL-6R), and vascular endothelial growth factor A (VEGFA) (FIG. 6D and Data S1). KPC1 and NF-κB were included in this analysis to retrieve possible known interactions, although KPC1 had no known interactions with any of the differentially regulated genes. A closer look at the core interaction network (FIG. 6D, inset magnification) which included NF-κB is most prominently annotated with "regulation of cell migration" genes. Most other core network genes are up-regulated and include many well-known tumor-suppressor genes.

Taken together, the findings strongly suggest a model of KPC1/p50 driven glioblastoma tumor growth inhibition, that centers around down-regulated high mobility group AT-hook 2 (HMGA2), lin-28 homolog A (LIN28), IL-6/IL-6R, and VEGFA, and up regulated tumor suppressors, which in combination control the tumor-microenvironment as well as glioblastoma stem cell maintenance.

Example 8

Correlation Between Expression of KPC1 and p50 in Human Tumoral and Normal Tissues Finally, the relationship between KPC1 and p50 in human tumors and normal tissues was examined.

Immunohistochemical staining of the two proteins (the two antibodies were shown to be specific; see FIGS. 13A-B) revealed a high correlation between them in head and neck squamous cell carcinoma (SCCHN, 52 sections; p-value<0.005; see for example FIG. 7B), breast cancer (105 sections; p-value<0.0001), and glioblastoma (192 sections; p-value<0.0001) (FIG. 7A). It should be emphasized though that the linkage may be tumor-specific, and not common to all patients with the 'same' tumor.

To test the hypothesis that loss of KPC1 and nuclear p50 can be involved in the pathogenesis of malignant transformation, the staining of the two proteins in SCCHN, breast cancer, and glioblastoma were analyzed, and compared it to their staining in the normal parallel tissue. A strong decrease in tumor samples stained for nuclear p50 was observed compared to the healthy tissue (FIG. 7C). As for KPC1, a significant decrease in staining intensity (reflecting the amount of the protein) was observed in cancerous compared to normal tissue in both SCCHN and glial cells, but not in breast cancer. Also, a significant decrease in the number of tumor samples stained for KPC1 in SCCHN was noted (FIG. 7C). Taken together, these findings suggest that nuclear p50 is indeed a tumor suppressor lost in many malignancies. At least part of this p50 loss may be due to loss of KPC1 which catalyzes its formation, though this may not be common to all tumors.

Supplemental Information

Additional information can be found from the results demonstrated in FIGS. 8A-G, 9A-D, 10A-C, 11, 12A and B and 13 A and B, which are described, as well as their relevancy to the other Figures described above, in the Brief Description of the Drawings Section.

Discussion

The vast majority of substrates of the Ub proteasome system are completely degraded. One intriguing and exceptional case is that of the p105 precursor of NF-κB that can be either completely degraded or processed in a limited manner to yield the p50 active subunit of the transcription factor. The "decision-making" mechanism resulting in one of the two distinct processes has remained largely elusive. The □TrCP Ub ligase has been identified as the tagging enzyme involved in complete degradation of p105, whereas the ligase involved in processing has remained unknown. The KPC complex has been identified as the putative p105-processing ligase (FIGS. 1A-C, 2A-J and 3A-F).

Now that the two E3s involved in degradation and processing of p105 have been identified, it is still not known why ubiquitination by one enzyme results in a completely different fate of p105 than ubiquitination by the other, and what determines the timing of the two reactions. It is possible that the two ligases catalyze the formation of chains that differ in their anchoring sites, length and/or internal linkages. These in turn affect the recognition and mechanism of action of the 26S proteasome. As for timing, it can be that different physiological conditions and/or the degree of saturation of the ARs with bound p50s are involved in the "decision-making" process of whether the molecule will be processed or destroyed completely.

Studying the biological implications of manipulating KPC1 revealed that it suppresses anchorage-independent growth in a manner that is dependent on its ligase activity and the presence of p105. A corollary strong tumor suppressive effect was demonstrated in xenografts of human tumors (FIGS. 4A-D, 5A-E and 6A-D). This effect is caused probably by a significant increase in an entire set of tumor suppressors, some of them like the brain-specific protein cell adhesion molecule 3 (CADM3) (Gao, J., Chen, T., Liu, J., Liu, W., Hu, G., Guo, X., Yin, B., Gong, Y., Zhao, J., Qiang, B., et al. (2009). Loss of NECL1, a novel tumor suppressor, can be restored in glioma by HDAC inhibitor-Trichostatin A through Sp1 binding site. Glia 57, 989-999), was found inactivated in glioblastoma.

An important question relates to the transcriptional mechanism by which KPC1 and p50 exert their tumor suppressive effect. An obvious assumption is that the stoichiometric excess of p50 generated by KPC1 would generate mostly p50•p50 homodimers rather than the 'canonical' tumorigenic p50•p65 heterodimers. In line with this finding is also the observation that p65 level is decreased in KPC1— as well as in p50-overexpressing xenografts (FIG. 5D). It appears that each dimer of NF-κB family has unique and even opposing biological function(s), and regulates a distinct subset of downstream genes (Siggers, T., Chang, A. B., Teixeira, A., Wong, D., Williams, K. J., Ahmed, B., Ragoussis, J., Udalova, I. A., Smale, S. T., and Bulyk, M. L. (2012). Principles of dimer-specific gene regulation revealed by a comprehensive characterization of NF-kappaB family DNA binding. Nat. Immunol. 13, 95-102). p50 homodimer is supposed to act as a transcriptional repressor because it does not contain a transactivation domain (May, M. J., and Ghosh, S. (1997). Rel/NF-kappa B and I kappa B proteins: an overview. Semin. Cancer Biol. 8, 63-73). However, studies in vitro have shown that p50 homodimer can interact with different transcriptional modulators, such as Bcl-3 (Fujita, T., Nolan, G. P., Liou, H. C., Scott, M. L., and Baltimore, D. (1993). The candidate proto-oncogene bcl-3 encodes a transcriptional coactivator that activates through NF-kappa B p50 homodimers. Genes Dev. 7, 1354-1363), p300 (Deng, W. G., and Wu, K. K. (2003). Regulation of inducible nitric oxide synthase expression by p300 and p50 acetylation. J. Immunol. 171, 6581-6588) or HMGA1/2 (Perrella, M. A., Pellacani, A., Wiesel, P., Chin, M. T., Foster, L. C., Ibanez, M., Hsieh, C. M., Reeves, R., Yet, S. F., and Lee, M. E. (1999). High mobility group-I(Y) protein facilitates nuclear factor-kappaB binding and transactivation of the inducible nitric-oxide synthase promoter/enhancer. J. Biol. Chem. 274, 9045-9052) that are involved in chromatin remodeling. Disproportionate p50 may shift the composition of NF-κB dimers, resulting in overall tumor suppressive effect. Indeed, following overexpression of KPC1 or p50, there is a decrease in the level of what is probably the 'canonical' tumorigenic NF-kB (p50•p65; FIG. 12A).

A strong correlation between the expression of KPC1 and that of p50 in human tumors has been found (FIGS. 7A and B). Moreover, a significant decrease in nuclear p50 and KPC1 staining intensity in tumors compared to non-malignant tissue was also found (FIG. 7C). This observation suggests that loss of nuclear p50 may trigger malignant transformation. In line with these findings are data collected in the Catalog Of Somatic Mutations in Cancer (COSMIC) that show a significantly greater number of common tumors (e.g. breast, lung, CNS, and uterine cervix) with decreased expression of KPC1 transcripts compared to those with high expression (http://cancer.sanger.ac.uk/cosmic/gene/analysis? ln=RNF123 &ln1=RNF123 &start=1&end=1315&coords=AA%3AAA&sn=&ss=&hn=&sh=&samps=1001&expn=over&expn=under&id=4185).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

REFERENCES

Barre, B., Coqueret, O., and Perkins, N. D. (2010). Regulation of activity and function of the p52 NF-kappaB subunit following DNA damage. Cell Cycle 9, 4795-4804.

Barre, B., and Perkins, N. D. (2007). A cell cycle regulatory network controlling NF-kappaB subunit activity and function. EMBO J. 26, 4841-4855.

Ben-Neriah, Y., and Karin, M. (2011). Inflammation meets cancer, with NF-kappaB as the matchmaker. Nat. Immunol. 12, 715-723.

Betts, J. C., and Nabel, G. J. (1996). Differential regulation of NF-kappaB2(p100) processing and control by amino-terminal sequences. Mol. Cell Biol. 16, 6363-6371.

Bonavia, R., Inda, M. M., Cavenee, W. K., and Furnari, F. B. (2011). Heterogeneity maintenance in glioblastoma: a social network. Cancer Res. 71, 4055-4060.

Cohen, S., Achbert-Weiner, H., and Ciechanover, A. (2004). Dual effects of IkappaB kinase beta-mediated phosphorylation on p105 Fate: SCF(beta-TrCP)-dependent degradation and SCF(beta-TrCP)-independent processing. Mol. Cell Biol. 24, 475-486.

Deng, W. G., and Wu, K. K. (2003). Regulation of inducible nitric oxide synthase expression by p300 and p50 acetylation. J. Immunol. 171, 6581-6588.

DiDonato, J. A., Mercurio, F., and Karin, M. (2012). NF-kappaB and the link between inflammation and cancer. Immunol. Rev. 246, 379-400.

Fan, C. M., and Maniatis, T. (1991). Generation of p50 subunit of NF-kappa B by processing of p105 through an ATP-dependent pathway. Nature 354, 395-398.

Fujita, T., Nolan, G. P., Liou, H. C., Scott, M. L., and Baltimore, D. (1993). The candidate proto-oncogene bcl-3 encodes a transcriptional coactivator that activates through NF-kappa B p50 homodimers. Genes Dev. 7, 1354-1363.

Gao, J., Chen, T., Liu, J., Liu, W., Hu, G., Guo, X., Yin, B., Gong, Y., Zhao, J., Qiang, B., et al. (2009). Loss of NECL1, a novel tumor suppressor, can be restored in glioma by HDAC inhibitor-Trichostatin A through Sp1 binding site. Glia 57, 989-999.

Hara, T., Kamura, T., Kotoshiba, S., Takahashi, H., Fujiwara, K., Onoyama, I., Shirakawa, M., Mizushima, N., and Nakayama, K. I. (2005). Role of the UBL-UBA protein KPC2 in degradation of p27 at G1 phase of the cell cycle. Mol. Cell Biol. 25, 9292-9303.

Heddleston, J. M., Li, Z., McLendon, R. E., Hjelmeland, A. B., and Rich, J. N. (2009). The hypoxic microenvironment maintains glioblastoma stem cells and promotes reprogramming towards a cancer stem cell phenotype. Cell Cycle 8, 3274-3284.

Heissmeyer, V., Krappmann, D., Hatada, E. N., and Scheidereit, C. (2001). Shared pathways of IkappaB kinase-induced SCF(betaTrCP)-mediated ubiquitination and degradation for the NF-kappaB precursor p105 and IkappaBalpha. Mol. Cell Biol. 21, 1024-1035.

Hershko, A., Heller, H., Elias, S., and Ciechanover, A. (1983). Components of ubiquitin-protein ligase system. Resolution, affinity purification, and role in protein breakdown. J. Biol. Chem. 258, 8206-8214.

Ivanov, V. N., Lee, R. K., Podack, E. R., and Malek, T. R. (1997). Regulation of Fas-dependent activation-induced T cell apoptosis by cAMP signaling: a potential role for transcription factor NF-kappa B. Oncogene 14, 2455-2464.

Kamura, T., Hara, T., Matsumoto, M., Ishida, N., Okumura, F., Hatakeyama, S., Yoshida, M., Nakayama, K., and Nakayama, K. I. (2004). Cytoplasmic ubiquitin ligase KPC regulates proteolysis of p27(Kip1) at G1 phase. Nat. Cell Biol. 6, 1229-1235.

Kravtsova-Ivantsiv, Y., Cohen, S., and Ciechanover, A. (2009). Modification by single ubiquitin moieties rather than polyubiquitination is sufficient for proteasomal processing of the p105 NF-kappaB precursor. Mol. Cell 33, 496-504.

Lin, L., DeMartino, G. N., and Greene, W. C. (1998). Cotranslational biogenesis of NF-kappaB p50 by the 26S proteasome. Cell 92, 819-828.

Lin, L., and Ghosh, S. (1996). A glycine-rich region in NF-kappaB p105 functions as a processing signal for the generation of the p50 subunit. Mol. Cell Biol. 16, 2248-2254.

MacKichan, M. L., Logeat, F., and Israel, A. (1996). Phosphorylation of p105 PEST sequence via a redox-insensitive pathway up-regulates processing of p50 NF-kappaB. J. Biol. Chem. 271, 6084-6091.

May, M. J., and Ghosh, S. (1997). Rel/NF-kappa B and I kappa B proteins: an overview. Semin. Cancer Biol. 8, 63-73.

Orian, A., Gonen, H., Bercovich, B., Fajerman, I., Eytan, E., Israel, A., Mercurio, F., Iwai, K., Schwartz, A. L., and Ciechanover, A. (2000). SCF(beta)(-TrCP) ubiquitin ligase-mediated processing of NF-kappaB p105 requires phosphorylation of its C-terminus by IkappaB kinase. EMBO J. 19, 2580-2591.

Palombella, V. J., Rando, O. J., Goldberg, A. L., and Maniatis, T. (1994). The ubiquitin-proteasome pathway is required for processing the NF-kB1 precursor protein and the activation of NF-kappa B. Cell 78, 773-785.

Perkins, N. D. (2012). The diverse and complex roles of NF-kappaB subunits in cancer. Nat. Rev. Cancer 12, 121-132.

Perrella, M. A., Pellacani, A., Wiesel, P., Chin, M. T., Foster, L. C., Ibanez, M., Hsieh, C. M., Reeves, R., Yet, S. F., and Lee, M. E. (1999). High mobility group-I(Y) protein facilitates nuclear factor-kappaB binding and transactivation of the inducible nitric-oxide synthase promoter/enhancer. J. Biol. Chem. 274, 9045-9052.

Pikarsky, E., and Ben-Neriah, Y. (2006). NF-kappaB inhibition: a double-edged sword in cancer? Eur. J. Cancer 42, 779-784.

Rahman, M. M., and McFadden, G. (2011). Modulation of NF-kappaB signalling by microbial pathogens. Nat. Rev. Microbiol. 9, 291-306.

Salmeron, A., Janzen, J., Soneji, Y., Bump, N., Kamens, J., Allen, H., and Ley, S. C. (2001). Direct phosphorylation of NF-kappaB1 p105 by the IkappaB kinase complex on serine 927 is essential for signal-induced p105 proteolysis. J. Biol. Chem. 276, 22215-22222.

Siggers, T., Chang, A. B., Teixeira, A., Wong, D., Williams, K. J., Ahmed, B., Ragoussis, J., Udalova, I. A., Smale, S. T., and Bulyk, M. L. (2012). Principles of dimer-specific gene regulation revealed by a comprehensive characterization of NF-kappaB family DNA binding. Nat. Immunol. 13, 95-102.

Voce, D. J., Schmitt, A. M., Uppal, A., McNerney, M. E., Bernal, G. M., Cahill, K. E., Wahlstrom, J. S., Nassiri, A., Yu, X., Crawley, C. D., et al. (2014). Nfkb1 is a haplo-insufficient DNA damage-specific tumor suppressor. Oncogene.

Zaaroor-Regev, D., de Bie, P., Scheffner, M., Noy, T., Shemer, R., Heled, M., Stein, I., Pikarsky, E., and Ciechanover, A. (2010). Regulation of the polycomb protein Ring1B by self-ubiquitination or by E6-AP may have implications to the pathogenesis of Angelman syndrome. Proc. Natl. Acad. Sci USA 107, 6788-6793.

SEQUENCE LISTING

<160> NUMBER OF SEQ ID NOS: 21

<210> SEQ ID NO 1
<211> LENGTH: 969
<212> TYPE: PRT
<213> ORGANISM: Homo sapiens

<400> SEQUENCE: 1

```
Met Ala Glu Asp Asp Pro Tyr Leu Gly Arg Pro Glu Gln Met Phe His
1               5                   10                  15

Leu Asp Pro Ser Leu Thr His Thr Ile Phe Asn Pro Glu Val Phe Gln
            20                  25                  30

Pro Gln Met Ala Leu Pro Thr Ala Asp Gly Pro Tyr Leu Gln Ile Leu
        35                  40                  45

Glu Gln Pro Lys Gln Arg Gly Phe Arg Phe Arg Tyr Val Cys Glu Gly
    50                  55                  60

Pro Ser His Gly Gly Leu Pro Gly Ala Ser Ser Glu Lys Asn Lys Lys
65                  70                  75                  80

Ser Tyr Pro Gln Val Lys Ile Cys Asn Tyr Val Gly Pro Ala Lys Val
                85                  90                  95

Ile Val Gln Leu Val Thr Asn Gly Lys Asn Ile His Leu His Ala His
            100                 105                 110

Ser Leu Val Gly Lys His Cys Glu Asp Gly Ile Cys Thr Val Thr Ala
        115                 120                 125

Gly Pro Lys Asp Met Val Val Gly Phe Ala Asn Leu Gly Ile Leu His
    130                 135                 140

Val Thr Lys Lys Lys Val Phe Glu Thr Leu Glu Ala Arg Met Thr Glu
145                 150                 155                 160

Ala Cys Ile Arg Gly Tyr Asn Pro Gly Leu Leu Val His Pro Asp Leu
                165                 170                 175

Ala Tyr Leu Gln Ala Glu Gly Gly Gly Asp Arg Gln Leu Gly Asp Arg
            180                 185                 190

Glu Lys Glu Leu Ile Arg Gln Ala Ala Leu Gln Gln Thr Lys Glu Met
        195                 200                 205

Asp Leu Ser Val Val Arg Leu Met Phe Thr Ala Phe Leu Pro Asp Ser
    210                 215                 220

Thr Gly Ser Phe Thr Arg Arg Leu Glu Pro Val Val Ser Asp Ala Ile
225                 230                 235                 240

Tyr Asp Ser Lys Ala Pro Asn Ala Ser Asn Leu Lys Ile Val Arg Met
                245                 250                 255

Asp Arg Thr Ala Gly Cys Val Thr Gly Gly Glu Glu Ile Tyr Leu Leu
            260                 265                 270

Cys Asp Lys Val Gln Lys Asp Asp Ile Gln Ile Arg Phe Tyr Glu Glu
        275                 280                 285

Glu Glu Asn Gly Gly Val Trp Glu Gly Phe Gly Asp Phe Ser Pro Thr
    290                 295                 300

Asp Val His Arg Gln Phe Ala Ile Val Phe Lys Thr Pro Lys Tyr Lys
305                 310                 315                 320

Asp Ile Asn Ile Thr Lys Pro Ala Ser Val Phe Val Gln Leu Arg Arg
                325                 330                 335

Lys Ser Asp Leu Glu Thr Ser Glu Pro Lys Pro Phe Leu Tyr Tyr Pro
            340                 345                 350

Glu Ile Lys Asp Lys Glu Glu Val Gln Arg Lys Arg Gln Lys Leu Met
        355                 360                 365
```

```
Pro Asn Phe Ser Asp Ser Phe Gly Gly Gly Ser Gly Ala Gly Ala Gly
    370                 375                 380
Gly Gly Gly Met Phe Gly Ser Gly Gly Gly Gly Gly Thr Gly Ser
385                 390                 395                 400
Thr Gly Pro Gly Tyr Ser Phe Pro His Tyr Gly Phe Pro Thr Tyr Gly
                405                 410                 415
Gly Ile Thr Phe His Pro Gly Thr Thr Lys Ser Asn Ala Gly Met Lys
            420                 425                 430
His Gly Thr Met Asp Thr Glu Ser Lys Lys Asp Pro Glu Gly Cys Asp
        435                 440                 445
Lys Ser Asp Asp Lys Asn Thr Val Asn Leu Phe Gly Lys Val Ile Glu
    450                 455                 460
Thr Thr Glu Gln Asp Gln Glu Pro Ser Glu Ala Thr Val Gly Asn Gly
465                 470                 475                 480
Glu Val Thr Leu Thr Tyr Ala Thr Gly Thr Lys Glu Ser Ala Gly
                485                 490                 495
Val Gln Asp Asn Leu Phe Leu Glu Lys Ala Met Gln Leu Ala Lys Arg
        500                 505                 510
His Ala Asn Ala Leu Phe Asp Tyr Ala Val Thr Gly Asp Val Lys Met
    515                 520                 525
Leu Leu Ala Val Gln Arg His Leu Thr Ala Val Gln Asp Glu Asn Gly
530                 535                 540
Asp Ser Val Leu His Leu Ala Ile Ile His Leu His Ser Gln Leu Val
545                 550                 555                 560
Arg Asp Leu Leu Glu Val Thr Ser Gly Leu Ile Ser Asp Asp Ile Ile
                565                 570                 575
Asn Met Arg Asn Asp Leu Tyr Gln Thr Pro Leu His Leu Ala Val Ile
            580                 585                 590
Thr Lys Gln Glu Asp Val Val Glu Asp Leu Leu Arg Ala Gly Ala Asp
        595                 600                 605
Leu Ser Leu Leu Asp Arg Leu Gly Asn Ser Val Leu His Leu Ala Ala
    610                 615                 620
Lys Glu Gly His Asp Lys Val Leu Ser Ile Leu Leu Lys His Lys Lys
625                 630                 635                 640
Ala Ala Leu Leu Leu Asp His Pro Asn Gly Asp Gly Leu Asn Ala Ile
                645                 650                 655
His Leu Ala Met Met Ser Asn Ser Leu Pro Cys Leu Leu Leu Leu Val
            660                 665                 670
Ala Ala Gly Ala Asp Val Asn Ala Gln Glu Gln Lys Ser Gly Arg Thr
        675                 680                 685
Ala Leu His Leu Ala Val Glu His Asp Asn Ile Ser Leu Ala Gly Cys
    690                 695                 700
Leu Leu Leu Glu Gly Asp Ala His Val Asp Ser Thr Thr Tyr Asp Gly
705                 710                 715                 720
Thr Thr Pro Leu His Ile Ala Ala Gly Arg Gly Ser Thr Arg Leu Ala
                725                 730                 735
Ala Leu Leu Lys Ala Ala Gly Ala Asp Pro Leu Val Glu Asn Phe Glu
            740                 745                 750
Pro Leu Tyr Asp Leu Asp Asp Ser Trp Glu Asn Ala Gly Glu Asp Glu
        755                 760                 765
Gly Val Val Pro Gly Thr Thr Pro Leu Asp Met Ala Thr Ser Trp Gln
    770                 775                 780
Val Phe Asp Ile Leu Asn Gly Lys Pro Tyr Glu Pro Glu Phe Thr Ser
```

```
                785             790              795              800
Asp Asp Leu Leu Ala Gln Gly Asp Met Lys Gln Leu Ala Glu Asp Val
                    805              810              815

Lys Leu Gln Leu Tyr Lys Leu Leu Glu Ile Pro Asp Pro Asp Lys Asn
                820              825              830

Trp Ala Thr Leu Ala Gln Lys Leu Gly Leu Gly Ile Leu Asn Asn Ala
                835              840              845

Phe Arg Leu Ser Pro Ala Pro Ser Lys Thr Leu Met Asp Asn Tyr Glu
            850              855              860

Val Ser Gly Gly Thr Val Arg Glu Leu Val Glu Ala Leu Arg Gln Met
865              870              875              880

Gly Tyr Thr Glu Ala Ile Glu Val Ile Gln Ala Ala Ser Ser Pro Val
                    885              890              895

Lys Thr Thr Ser Gln Ala His Ser Leu Pro Leu Ser Pro Ala Ser Thr
                900              905              910

Arg Gln Gln Ile Asp Glu Leu Arg Asp Ser Asp Ser Val Cys Asp Ser
                915              920              925

Gly Val Glu Thr Ser Phe Arg Lys Leu Ser Phe Thr Glu Ser Leu Thr
            930              935              940

Ser Gly Ala Ser Leu Leu Thr Leu Asn Lys Met Pro His Asp Tyr Gly
945              950              955              960

Gln Glu Gly Pro Leu Glu Gly Lys Ile
                    965

<210> SEQ ID NO 2
<211> LENGTH: 2910
<212> TYPE: DNA
<213> ORGANISM: Homo sapiens

<400> SEQUENCE: 2
atggcagaag atgatccata tttgggaagg cctgaacaaa tgtttcattt ggatccttct      60
ttgactcata caatatttaa tccagaagta tttcaaccac agatggcact gccaacagca     120
gatggcccat accttcaaat attagagcaa cctaaacaga gaggatttcg tttccgttat     180
gtatgtgaag gccatcccat ggtggactac cctggtgcct ctagtgaaaa gaacaagaag     240
tcttaccctc aggtcaaaat ctgcaactat gtgggaccag caaaggttat tgttcagttg     300
gtcacaaatg gaaaaaatat ccacctgcat gcccacagcc tggtgggaaa acactgtgag     360
gatgggatct gcactgtaac tgctggaccc aaggacatgg tggtcggctt cgcaaacctg     420
ggtatacttc atgtgacaaa gaaaaaagta tttgaaacac tggaagcacg aatgacagag     480
gcgtgtataa ggggctataa tcctggactc ttggtgcacc ctgaccttgc ctatttgcaa     540
gcagaaggtg gaggggaccg gcagctggga gatcggaaa aagagctaat ccgccaagca     600
gctctgcagc agaccaagga gatggacctc agcgtggtgc ggctcatgtt tacagctttt     660
cttccggata gcactggcag cttcacaagg cgcctggaac ccgtggtatc agacgccatc     720
tatgacagta aagcccccaa tgcatccaac ttgaaaattg taagaatgga caggacagct     780
ggatgtgtga ctggagggga ggaaatttat cttctttgtg acaaagttca gaaagatgac     840
atccagattc gattttatga agaggaagaa atggtggag tctgggaagg atttggagat     900 ttttcccca cagatgttca tagacaattt gccattgtct tcaaaactcc aaagtataaa     960
gatattaata ttacaaaacc agcctctgtg tttgtccagc ttcggaggaa atctgacttg    1020
gaaactagtg aaccaaaacc tttcctctac tatcctgaaa tcaaagataa agaagaagtg    1080
```

```
cagaggaaac gtcagaagct catgcccaat ttttcggata gtttcggcgg tggtagtggt    1140
gctggagctg gaggcggagg catgtttggt agtggcggtg gaggagggg  cactggaagt    1200 acaggtccag ggtatagctt cccacactat ggatttccta cttatggtgg gattactttc    1260
catcctggaa ctactaaatc taatgctggg atgaagcatg gaaccatgga cactgaatct    1320
aaaaaggacc ctgaaggttg tgacaaaagt gatgacaaaa acactgtaaa cctctttggg    1380
aaagttattg aaaccacaga gcaagatcag gagcccagcg aggccaccgt tgggaatggt    1440
gaggtcactc taacgtatgc aacaggaaca aaagaagaga gtgctggagt tcaggataac    1500
ctctttctag agaaggctat gcagcttgca aagaggcatg ccaatgccct tttcgactac    1560
gcggtgacag agacgtgaa  gatgctgctg ccgtccagc  gccatctcac tgctgtgcag    1620
gatgagaatg gggacagtgt cttacactta gcaatcatcc accttcattc tcaacttgtg    1680
agggatctac tagaagtcac atctggtttg atttctgatg acattatcaa catgagaaat    1740
gatctgtacc agacgccctt gcacttggca gtgatcacta gcaggaaga  tgtggtggag    1800 gatttgctga gggctgggc  cgacctgagc cttctggacc gcttgggtaa ctctgttttg    1860
cacctagctg ccaaagaagg acatgataaa gttctcagta tcttactcaa gcacaaaaag    1920
gcagcactac ttcttgacca ccccaacggg gacggtctga atgccattca tctagccatg    1980
atgagcaata gcctgccatg tttgctgctg ctggtggccg ctgggctga  cgtcaatgct    2040 caggagcaga agtccgggcg cacagcactg cacctggctg tggagcacga caacatctca    2100
ttggcaggct gcctgctcct ggagggtgat gcccatgtgg acagtactac ctacgatgga    2160
accacacccc tgcatatagc agctgggaga gggtccacca ggctggcagc tcttctcaaa    2220
gcagcaggag cagatcccct ggtggagaac tttgagcctc tctatgacct ggatgactct    2280
tgggaaaatg caggagagga tgaaggagtt gtgcctggaa ccacgcctct agatatggcc    2340
accagctggc aggtatttga catattaaat gggaaaccat atgagccaga gtttacatct    2400
gatgatttac tagcacaagg agacatgaaa cagctggctg aagatgtgaa gctgcagctg    2460
tataagttac tagaaattcc tgatccagac aaaaactggg ctactctggc gcagaaatta    2520
ggtctgggga tacttaataa tgccttccgg ctgagtcctg ctccttccaa aacacttatg    2580
gacaactatg aggtctctgg gggtacagtc agagagctgg tggaggccct gagacaaatg    2640
ggctacaccg aagcaattga agtgatccag gcagcctcca gcccagtgaa gaccaccctct   2700 caggcccact cgctgcctct ctcgcctgcc tccacaaggc agcaaataga cgagctccga    2760
gacagtgaca gtgtctgcga cagcggcgtg gagacatcct ccgcaaaact cagctttacc    2820
gagtctctga ccagtggtgc ctcactgcta actctcaaca aaatgcccca tgattatggg    2880
caggaaggac ctctagaagg caaaatttag                                     2910
```

<210> SEQ ID NO 3
<211> LENGTH: 434
<212> TYPE: PRT
<213> ORGANISM: Homo sapiens

<400> SEQUENCE: 3

```
Met Ala Glu Asp Asp Pro Tyr Leu Gly Arg Pro Glu Gln Met Phe His
1               5                   10                  15

Leu Asp Pro Ser Leu Thr His Thr Ile Phe Asn Pro Glu Val Phe Gln
            20                  25                  30

Pro Gln Met Ala Leu Pro Thr Ala Asp Gly Pro Tyr Leu Gln Ile Leu
        35                  40                  45
```

```
Glu Gln Pro Lys Gln Arg Gly Phe Arg Phe Arg Tyr Val Cys Glu Gly
 50                  55                  60

Pro Ser His Gly Gly Leu Pro Gly Ala Ser Ser Glu Lys Asn Lys Lys
 65                  70                  75                  80

Ser Tyr Pro Gln Val Lys Ile Cys Asn Tyr Val Gly Pro Ala Lys Val
                 85                  90                  95

Ile Val Gln Leu Val Thr Asn Gly Lys Asn Ile His Leu His Ala His
            100                 105                 110

Ser Leu Val Gly Lys His Cys Glu Asp Gly Ile Cys Thr Val Thr Ala
            115                 120                 125

Gly Pro Lys Asp Met Val Val Gly Phe Ala Asn Leu Gly Ile Leu His
130                 135                 140

Val Thr Lys Lys Lys Val Phe Glu Thr Leu Glu Ala Arg Met Thr Glu
145                 150                 155                 160

Ala Cys Ile Arg Gly Tyr Asn Pro Gly Leu Leu Val His Pro Asp Leu
                165                 170                 175

Ala Tyr Leu Gln Ala Glu Gly Gly Asp Arg Gln Leu Gly Asp Arg
            180                 185                 190

Glu Lys Glu Leu Ile Arg Gln Ala Ala Leu Gln Gln Thr Lys Glu Met
            195                 200                 205

Asp Leu Ser Val Val Arg Leu Met Phe Thr Ala Phe Leu Pro Asp Ser
210                 215                 220

Thr Gly Ser Phe Thr Arg Arg Leu Glu Pro Val Val Ser Asp Ala Ile
225                 230                 235                 240

Tyr Asp Ser Lys Ala Pro Asn Ala Ser Asn Leu Lys Ile Val Arg Met
                245                 250                 255

Asp Arg Thr Ala Gly Cys Val Thr Gly Gly Glu Glu Ile Tyr Leu Leu
            260                 265                 270

Cys Asp Lys Val Gln Lys Asp Asp Ile Gln Ile Arg Phe Tyr Glu Glu
            275                 280                 285

Glu Glu Asn Gly Gly Val Trp Glu Gly Phe Gly Asp Phe Ser Pro Thr
            290                 295                 300

Asp Val His Arg Gln Phe Ala Ile Val Phe Lys Thr Pro Lys Tyr Lys
305                 310                 315                 320

Asp Ile Asn Ile Thr Lys Pro Ala Ser Val Phe Val Gln Leu Arg Arg
                325                 330                 335

Lys Ser Asp Leu Glu Thr Ser Glu Pro Lys Pro Phe Leu Tyr Tyr Pro
            340                 345                 350

Glu Ile Lys Asp Lys Glu Glu Val Gln Arg Lys Arg Gln Lys Leu Pro
            355                 360                 365

Asn Phe Ser Asp Ser Phe Gly Gly Gly Ser Gly Ala Gly Ala Gly Gly
            370                 375                 380

Gly Gly Met Phe Gly Ser Gly Gly Gly Gly Gly Thr Gly Ser Thr
385                 390                 395                 400

Gly Pro Gly Tyr Ser Phe Pro His Tyr Gly Phe Pro Thr Tyr Gly Gly
                405                 410                 415

Ile Thr Phe His Pro Gly Thr Thr Lys Ser Asn Ala Gly Met Lys His
            420                 425                 430

Gly Thr

<210> SEQ ID NO 4
<211> LENGTH: 1314
<212> TYPE: PRT
<213> ORGANISM: Homo sapiens
```

<400> SEQUENCE: 4

```
Met Ala Ser Lys Gly Ala Gly Met Ser Phe Ser Arg Lys Ser Tyr Arg
1               5                   10                  15

Leu Thr Ser Asp Ala Glu Lys Ser Arg Val Thr Gly Ile Val Gln Glu
            20                  25                  30

Lys Leu Leu Asn Asp Tyr Leu Asn Arg Ile Phe Ser Ser Ser Glu His
        35                  40                  45

Ala Pro Ala Ala Thr Ser Arg Lys Pro Leu Asn Phe Gln Asn Leu
    50                  55                  60

Pro Glu His Leu Asp Gln Leu Leu Gln Val Asp Asn Glu Glu Glu
65                  70                  75                  80

Ser Gln Gly Gln Val Glu Gly Arg Leu Gly Pro Ser Thr Val Leu
                85                  90                  95

Asp His Thr Gly Gly Phe Glu Gly Leu Leu Leu Val Asp Asp Asp Leu
                100                 105                 110

Leu Gly Val Ile Gly His Ser Asn Phe Gly Thr Ile Arg Ser Thr Thr
            115                 120                 125

Cys Val Tyr Lys Gly Lys Trp Leu Tyr Glu Val Leu Ile Ser Ser Gln
        130                 135                 140

Gly Leu Met Gln Ile Gly Trp Cys Thr Ile Ser Cys Arg Phe Asn Gln
145                 150                 155                 160

Glu Glu Gly Val Gly Asp Thr His Asn Ser Tyr Ala Tyr Asp Gly Asn
                165                 170                 175

Arg Val Arg Lys Trp Asn Val Thr Thr Thr Asn Tyr Gly Lys Ala Trp
            180                 185                 190

Ala Ala Gly Asp Ile Val Ser Cys Leu Ile Asp Leu Asp Asp Gly Thr
        195                 200                 205

Leu Ser Phe Cys Leu Asn Gly Val Ser Leu Gly Thr Ala Phe Glu Asn
210                 215                 220

Leu Ser Arg Gly Leu Gly Met Ala Tyr Phe Pro Ala Ile Ser Leu Ser
225                 230                 235                 240

Phe Lys Glu Ser Val Ala Phe Asn Phe Gly Ser Arg Pro Leu Arg Tyr
            245                 250                 255

Pro Val Ala Gly Tyr Arg Pro Leu Gln Asp Pro Pro Ser Ala Asp Leu
        260                 265                 270

Val Arg Ala Gln Arg Leu Leu Gly Cys Phe Arg Ala Val Leu Ser Val
275                 280                 285

Glu Leu Asp Pro Val Glu Gly Arg Leu Leu Asp Lys Glu Ser Ser Lys
    290                 295                 300

Trp Arg Leu Arg Gly Gln Pro Thr Val Leu Leu Thr Leu Ala His Ile
305                 310                 315                 320

Phe His His Phe Ala Pro Leu Leu Arg Lys Val Tyr Leu Val Glu Ala
                325                 330                 335

Val Leu Met Ser Phe Leu Leu Gly Ile Val Glu Lys Gly Thr Pro Thr
            340                 345                 350

Gln Ala Gln Ser Val Val His Gln Val Leu Asp Leu Leu Trp Leu Phe
        355                 360                 365

Met Glu Asp Tyr Glu Val Gln Asp Cys Leu Lys Gln Leu Met Met Ser
    370                 375                 380

Leu Leu Arg Leu Tyr Arg Phe Ser Pro Ile Val Pro Asp Leu Gly Leu
385                 390                 395                 400

Gln Ile His Tyr Leu Arg Leu Thr Ile Ala Ile Leu Arg His Glu Lys
```

-continued

```
                405                 410                 415
Ser Arg Lys Phe Leu Leu Ser Asn Val Leu Phe Asp Val Leu Arg Ser
            420                 425                 430

Val Val Phe Phe Tyr Ile Lys Ser Pro Leu Arg Val Glu Glu Ala Gly
            435                 440                 445

Leu Gln Glu Leu Ile Pro Thr Thr Trp Trp Pro His Cys Ser Ser Arg
            450                 455                 460

Glu Gly Lys Glu Ser Thr Glu Met Lys Glu Glu Thr Ala Glu Glu Arg
465                 470                 475                 480

Leu Arg Arg Arg Ala Tyr Glu Arg Gly Cys Gln Arg Leu Arg Lys Arg
                485                 490                 495

Ile Glu Val Val Glu Glu Leu Gln Val Gln Ile Leu Lys Leu Leu Leu
            500                 505                 510

Asp Asn Lys Asp Asp Asn Gly Gly Glu Ala Ser Arg Tyr Ile Phe Leu
            515                 520                 525

Thr Lys Phe Arg Lys Phe Leu Gln Glu Asn Ala Ser Gly Arg Gly Asn
            530                 535                 540

Met Pro Met Leu Cys Pro Pro Glu Tyr Met Val Cys Phe Leu His Arg
545                 550                 555                 560

Leu Ile Ser Ala Leu Arg Tyr Tyr Trp Asp Glu Tyr Lys Ala Ser Asn
                565                 570                 575

Pro His Ala Ser Phe Ser Glu Glu Ala Tyr Ile Pro Pro Gln Val Phe
            580                 585                 590

Tyr Asn Gly Lys Val Asp Tyr Phe Asp Leu Gln Arg Leu Gly Gly Leu
            595                 600                 605

Leu Ser His Leu Arg Lys Thr Leu Lys Asp Asp Leu Ala Ser Lys Ala
            610                 615                 620

Asn Ile Val Ile Asp Pro Leu Glu Leu Gln Ser Thr Ala Met Asp Asp
625                 630                 635                 640

Leu Asp Glu Asp Glu Glu Pro Ala Pro Ala Met Ala Gln Arg Pro Met
                645                 650                 655

Gln Ala Leu Ala Val Gly Gly Pro Leu Pro Leu Pro Arg Pro Gly Trp
            660                 665                 670

Leu Ser Ser Pro Thr Leu Gly Arg Ala Asn Arg Phe Leu Ser Thr Ala
            675                 680                 685

Ala Val Ser Leu Met Thr Pro Arg Arg Pro Leu Ser Thr Ser Glu Lys
            690                 695                 700

Val Lys Val Arg Thr Leu Ser Val Glu Gln Arg Thr Arg Glu Asp Ile
705                 710                 715                 720

Glu Gly Ser His Trp Asn Glu Gly Leu Leu Leu Gly Arg Pro Pro Glu
                725                 730                 735

Glu Pro Glu Gln Pro Leu Thr Glu Asn Ser Leu Leu Glu Val Leu Asp
            740                 745                 750

Gly Ala Val Met Met Tyr Asn Leu Ser Val His Gln Gln Leu Gly Lys
            755                 760                 765

Met Val Gly Val Ser Asp Asp Val Asn Glu Tyr Ala Met Ala Leu Arg
            770                 775                 780

Asp Thr Glu Asp Lys Leu Arg Arg Cys Pro Lys Arg Arg Lys Asp Ile
785                 790                 795                 800

Leu Ala Glu Leu Thr Lys Ser Gln Lys Val Phe Ser Glu Lys Leu Asp
                805                 810                 815

His Leu Ser Arg Arg Leu Ala Trp Val His Ala Thr Val Tyr Ser Gln
            820                 825                 830
```

-continued

```
Glu Lys Met Leu Asp Ile Tyr Trp Leu Leu Arg Val Cys Leu Arg Thr
        835                 840                 845
Ile Glu His Gly Asp Arg Thr Gly Ser Leu Phe Ala Phe Met Pro Glu
850                 855                 860
Phe Tyr Leu Ser Val Ala Ile Asn Ser Tyr Ser Ala Leu Lys Asn Tyr
865                 870                 875                 880
Phe Gly Pro Val His Ser Met Glu Glu Leu Pro Gly Tyr Glu Thr
                    885                 890                 895
Leu Thr Arg Leu Ala Ala Ile Leu Ala Lys His Phe Ala Asp Ala Arg
                900                 905                 910
Ile Val Gly Thr Asp Ile Arg Asp Ser Leu Met Gln Ala Leu Ala Ser
                915                 920                 925
Tyr Val Cys Tyr Pro His Ser Leu Arg Ala Val Glu Arg Ile Pro Glu
        930                 935                 940
Glu Gln Arg Ile Ala Met Val Arg Asn Leu Leu Ala Pro Tyr Glu Gln
945                 950                 955                 960
Arg Pro Trp Ala Gln Thr Asn Trp Ile Leu Val Arg Leu Trp Arg Gly
                    965                 970                 975
Cys Gly Phe Gly Tyr Arg Tyr Thr Arg Leu Pro His Leu Leu Lys Thr
                980                 985                 990
Lys Leu Glu Asp Ala Asn Leu Pro Ser Leu Gln Lys Pro Cys Pro Ser
        995                 1000                1005
Thr Leu Leu Gln Gln His Met Ala Asp Leu Leu Gln Gln Gly Pro
        1010                1015                1020
Asp Val Ala Pro Ser Phe Leu Asn Ser Val Leu Asn Gln Leu Asn
        1025                1030                1035
Trp Ala Phe Ser Glu Phe Ile Gly Met Ile Gln Glu Ile Gln Gln
        1040                1045                1050
Ala Ala Glu Arg Leu Glu Arg Asn Phe Val Asp Ser Arg Gln Leu
        1055                1060                1065
Lys Val Cys Ala Thr Cys Phe Asp Leu Ser Val Ser Leu Leu Arg
        1070                1075                1080
Val Leu Glu Met Thr Ile Thr Leu Val Pro Glu Ile Phe Leu Asp
        1085                1090                1095
Trp Thr Arg Pro Thr Ser Glu Met Leu Leu Arg Arg Leu Ala Gln
        1100                1105                1110
Leu Leu Asn Gln Val Leu Asn Arg Val Thr Ala Glu Arg Asn Leu
        1115                1120                1125
Phe Asp Arg Val Val Thr Leu Arg Leu Pro Gly Leu Glu Ser Val
        1130                1135                1140
Asp His Tyr Pro Ile Leu Val Ala Val Thr Gly Ile Leu Val Gln
        1145                1150                1155
Leu Leu Val Arg Gly Pro Ala Ser Glu Arg Glu Gln Ala Thr Ser
        1160                1165                1170
Val Leu Leu Ala Asp Pro Cys Phe Gln Leu Arg Ser Ile Cys Tyr
        1175                1180                1185
Leu Leu Gly Gln Pro Glu Pro Pro Ala Pro Gly Thr Ala Leu Pro
        1190                1195                1200
Ala Pro Asp Arg Lys Arg Phe Ser Leu Gln Ser Tyr Ala Asp Tyr
        1205                1210                1215
Ile Ser Ala Asp Glu Leu Ala Gln Val Glu Gln Met Leu Ala His
        1220                1225                1230
```

| | | | | | | | | | | |
|---|---|---|---|---|---|---|---|---|---|---|
|Leu|Thr|Ser|Ala|Ser|Ala|Gln|Ala|Ala|Ala|Ala|Ser|Leu|Pro|Thr|
| |1235| | | |1240| | | |1245| | | | | |

Ser Glu Glu Asp Leu Cys Pro Ile Cys Tyr Ala His Pro Ile Ser
    1250            1255            1260

Ala Val Phe Gln Pro Cys Gly His Lys Ser Cys Lys Ala Cys Ile
    1265            1270            1275

Asn Gln His Leu Met Asn Asn Lys Asp Cys Phe Phe Cys Lys Thr
    1280            1285            1290

Thr Ile Val Ser Val Glu Asp Trp Glu Lys Gly Ala Asn Thr Ser
    1295            1300            1305

Thr Thr Ser Ser Ala Ala
    1310

<210> SEQ ID NO 5
<211> LENGTH: 3945
<212> TYPE: DNA
<213> ORGANISM: Homo sapiens

<400> SEQUENCE: 5

```
atggcatcca agggggccgg catgtctttc tcccgcaaga gctataggct gacctcagat      60
gctgagaaat ccaggtcac aggcattgtg caggagaagc tgctgaatga ctacctgaac     120
cgcatctttt cctcttctga acatgcaccc ccagcagcca ccagcaggaa acccctgaac     180
ttccagaacc tgccagaaca tttggaccag ttgctacagg tggacaatga ggaggaggaa     240
agccagggac aggttgaagg gcggcttggc ccatccactg tggtcctgga ccacacaggc     300
ggctttgagg gcttctcct ggtggatgat gacctgctgg gggtgattgg acacagcaac     360
tttggcacca tccgctctac cacatgcgtg tacaaaggga atggctcta cgaggtcctc     420
atctcctccc aggggctcat gcagatcggc tggtgcacca tcagctgccg cttcaaccag     480
gaggaggggg ttgagatac acacaactcc tatgcctatg atggcaaccg cgtgcgcaag     540
tggaatgtga ccacaacgaa ttatggcaag gcgtgggcag cggggacat cgtgagctgc     600
ctgattgacc tggatgatgg cactctgtcc ttctgcctga cggtgtatc actgggcact     660
gcctttgaga acctgtccag gggcctgggt atggcctact cccagccat cagcctctct     720
ttcaaggagt ccgtggcctt caactttggc agccgtcctc tgcgctaccc agtggcaggc     780
taccggcccc tgcaggaccc accgagtgct gacctggtgc gggcacagag gttgctgggc     840
tgcttccggg cagtgctgag tgtggagctg gaccctgtgg aggggcggct gttggacaag     900
gagagctcca gtggcggtt gcggggccag cccaccgtcc tcctcacact ggcccacatc     960
ttccatcact ttgcaccgct tctgcgcaag gtgtatctgg tggaggctgt gctcatgagc    1020
ttcttgctgg catcgtgga aagggcaca cccacacagg cacagtccgt ggtgcaccag    1080
gtcctggacc tcttgtggct cttcatggag gactacgagg tacaagattg cctcaagcag    1140
ttgatgatgt ctctgcttcg gctgtaccga ttctcaccca ttgtcccaga cctgggccta    1200
cagatccatt acctgcggct cactatcgcc atcctgagge atgagaagtc ccgcaagttt    1260
ctgcttagca atgtcctctt cgacgtgctc cgctccgtcg tcttcttta catcaagagc    1320
cccctgcgtg tggaggaggc cggcctgcag gagctcattc ccaccacctg gtggccccac    1380
tgctccagta gggagggcaa agagagcacg gagatgaagg aggagaccgc agaggagcgg    1440
ctgcggcggc gagcctacga acggggctgt cagcggctca ggaagcgcat cgaagtggtg    1500
gaagaactac aggtccagat cctgaagctg ctgctggaca taaagatga caatgggggt    1560
gaagcttcta ggtatatctt cctgaccaag tttcgcaagt ttctgcagga gaacgccagt    1620
```

```
ggccggggga acatgcccat gctctgcccc cctgagtaca tggtctgctt cttacaccgg    1680
ctgatctctg ccctgcgcta ctattgggat gaatacaagg cttccaatcc tcatgcttcc    1740
ttcagtgagg aggcctacat cccgcccag gtcttctata tggcaaggt ggactacttt      1800 gacctgcagc gcctgggggg cctcctctcg cacctgcgga agaccctcaa agatgacctt    1860
gcttccaaag ccaacattgt gatcgaccca ctggagctcc agtcaaccgc catggatgac    1920
ctagatgagg atgaggagcc agccccagct atggcccagc gccccatgca ggccctggct    1980 gttgggggc cactgcccct gccccggccc ggctggctca gttctccaac tttgggccga     2040
gccaaccgct tcctcagcac agcggctgtg agcctcatga ccccacggcg gcctctgagc    2100
acctcggaga aagtgaaggt ccgcacgctg agcgtggagc agaggacccg tgaggacatt    2160
gaaggcagcc actggaatga gggcttgctg ctggggcggc ccccgagga gcctgagcag     2220 cccctcaccg agaactcgct gctggaagtc ctggatgggg cggtcatgat gtacaacctc    2280
agcgtacacc agcagctggg caagatggtg ggtgtctccg atgatgtcaa tgaatacgct    2340
atggctctga gggacacaga ggacaagctc cgccggtgcc ccaagaggag aaggacatc     2400 cttgcagagt tgaccaagag ccagaaggtt ttctcagaaa agctggacca cctgagccgc    2460
cgtcttgcct gggtccatgc cactgtctac tcccaggaga agatgctgga catctactgg    2520
ctgctgcgcg tctgcctgcg gaccattgag cacggtgatc gcacagggtc tctctttgcc    2580
ttcatgcccg agttctacct gagcgtggcc atcaacagct acagtgctct caagaattac    2640
tttggtcccg tgcacagcat ggaggagctc ccaggctatg aagagaccct gacccgcctg    2700
gctgccattc tcgccaaaca ctttgccgac gcacgcattg tgggcactga catccgagac    2760
tcactgatgc aggccctggc cagctacgtg tgctacccac actccctgcg ggctgtggag    2820
cgaatccccg aggagcagcg tatcgccatg gtgaggaacc tcctggcgcc ctatgagcag    2880
cggccctggg cccagaccaa ctggatcctg gtgcggctct ggaggggctg tggcttcggg    2940
taccgctata cacggctgcc acatctgctg aaaaccaaac ttgaggacgc caatttgccc    3000
agcctccaga gccctgccc ttccaccctg ctgcagcagc acatggcgga cctcctacag     3060
cagggtcctg atgtggcacc cagcttcctc aacagcgtcc tcaatcagct caactgggcc    3120
ttctctgaat tcattggcat gatccaagag atccagcagg ctgctgagcg cctggagcgg    3180
aactttgtgg acagccggca gctcaaggta tgtgccacct gctttgacct ctcggtcagc    3240
ctgctgcgtg tcttggagat gactatcaca ctggtgcctg agatattcct tgactggacc    3300
cggcctacct ctgagatgct gctgcggcgt cttgcacagc tgctaaacca ggtgctgaac    3360
cgggtgacag ctgagaggaa cctgtttgat cgtgtggtca ccctacggct gcctggccta    3420
gagagcgtgg accactatcc cattctggtg gcagtgacgg gcatcctggt gcagctcctg    3480
gtgcgtggcc cagcctcaga gagagagcaa gccacatcag tgctcctggc agatccctgc    3540
ttccagctac gctcaatatg ctatctcctg ggacagccag agccccagc acctggcact     3600 gctctgccag cccctgaccg gaagcgcttc tccctgcaga gctatgcgga ttatatcagt    3660
gccgatgagc tggcccaagt ggaacagatg ctggcgcacc tgacctctgc atctgcccag    3720
gcagcagctg cctccctgcc caccagtgag gaggacctct gccccatctg ctatgcccac    3780
cccatctctg ctgtgttcca gccctgtggc cacaagtcct gcaaagcctg tatcaaccag    3840
cacctgatga caacaagga ctgcttcttc tgcaaaacca ccatcgtgtc tgtagaggac     3900
tgggagaagg gagccaatac gagtactacc tcctcagctg cctag                    3945
```

-continued

```
<210> SEQ ID NO 6
<211> LENGTH: 1320
<212> TYPE: PRT
<213> ORGANISM: Mus musculus

<400> SEQUENCE: 6
```

| | | | | | | | | | | | | | | | |
|---|---|---|---|---|---|---|---|---|---|---|---|---|---|---|---|
| Met | Ala | Ser | Lys | Gly | Thr | Gly | Met | Ser | Phe | Ser | Arg | Lys | Ser | Tyr | Arg |
| 1 | | | | 5 | | | | | 10 | | | | | 15 | |
| Leu | Thr | Ser | Asp | Ala | Glu | Lys | Ser | Arg | Val | Thr | Gly | Ile | Val | Gln | Glu |
| | | | 20 | | | | | 25 | | | | | 30 | | |
| Lys | Leu | Leu | Ser | Asp | Tyr | Leu | Tyr | Arg | Ile | Phe | Ser | Pro | Pro | Asp | Arg |
| | | | | 35 | | | | | 40 | | | | | 45 | |
| Gly | Pro | Ala | Ala | Thr | Ser | Arg | Lys | Pro | Leu | Asn | Phe | His | Asn | Leu | |
| | | 50 | | | | | 55 | | | | | 60 | | | |
| Pro | Glu | His | Val | Asp | Gln | Leu | Leu | Gln | Val | Asp | Ser | Glu | Asp | Asn | Glu |
| 65 | | | | | 70 | | | | | 75 | | | | | 80 |
| Ser | Gln | Gly | Gln | Val | Glu | Gly | Arg | Leu | Gly | Pro | Ser | Thr | Val | Val | Leu |
| | | | | 85 | | | | | 90 | | | | | 95 | |
| Asp | His | Thr | Gly | Gly | Phe | Glu | Gly | Leu | Leu | Leu | Val | Asp | Asp | Asp | Leu |
| | | | 100 | | | | | 105 | | | | | 110 | | |
| Leu | Gly | Val | Ile | Gly | His | Ser | Asn | Phe | Gly | Thr | Ile | Arg | Ser | Thr | Thr |
| | | | | 115 | | | | | 120 | | | | | 125 | |
| Cys | Val | Tyr | Lys | Gly | Lys | Trp | Val | Tyr | Glu | Val | Leu | Ile | Ser | Ser | Gln |
| | 130 | | | | | 135 | | | | | 140 | | | | |
| Gly | Leu | Met | Gln | Ile | Gly | Trp | Cys | Thr | Ile | Asn | Cys | Arg | Phe | Asn | Gln |
| 145 | | | | | 150 | | | | | 155 | | | | | 160 |
| Glu | Glu | Gly | Val | Gly | Asp | Thr | His | Asn | Ser | Tyr | Ala | Tyr | Asp | Gly | Asn |
| | | | | 165 | | | | | 170 | | | | | 175 | |
| Arg | Val | Arg | Lys | Trp | Asn | Val | Thr | Thr | Thr | Asn | Tyr | Gly | Lys | Ala | Trp |
| | | | 180 | | | | | 185 | | | | | 190 | | |
| Ala | Ala | Gly | Asp | Ile | Val | Ser | Cys | Leu | Ile | Asp | Leu | Asp | Asp | Gly | Thr |
| | | | | 195 | | | | | 200 | | | | | 205 | |
| Leu | Ser | Phe | Cys | Leu | Asn | Gly | Val | Ser | Leu | Gly | Thr | Ala | Phe | Glu | Asn |
| | 210 | | | | | 215 | | | | | 220 | | | | |
| Leu | Ser | Arg | Gly | Leu | Gly | Met | Ala | Tyr | Phe | Pro | Ala | Ile | Ser | Leu | Ser |
| 225 | | | | | 230 | | | | | 235 | | | | | 240 |
| Phe | Lys | Glu | Ser | Val | Ala | Phe | Asn | Phe | Gly | Ser | Arg | Pro | Leu | Arg | Tyr |
| | | | | 245 | | | | | 250 | | | | | 255 | |
| Pro | Val | Ala | Gly | Phe | Arg | Pro | Leu | Gln | Asp | Pro | Pro | Phe | Ala | Asp | Leu |
| | | | 260 | | | | | 265 | | | | | 270 | | |
| Val | Arg | Ala | Gln | Arg | Leu | Leu | Gly | Cys | Phe | Gln | Ala | Val | Leu | Ser | Val |
| | | 275 | | | | | 280 | | | | | 285 | | | |
| Glu | Leu | Asp | Pro | Val | Glu | Gly | Arg | Leu | Val | Glu | Thr | Glu | Ser | Ser | Glu |
| | 290 | | | | | 295 | | | | | 300 | | | | |
| Trp | Gln | Leu | Gln | Gly | Gln | Pro | Thr | Val | Leu | Leu | Thr | Leu | Ala | His | Ile |
| 305 | | | | | 310 | | | | | 315 | | | | | 320 |
| Phe | His | His | Phe | Ala | Pro | Leu | Leu | Arg | Lys | Val | Tyr | Leu | Val | Glu | Ala |
| | | | | 325 | | | | | 330 | | | | | 335 | |
| Val | Leu | Met | Ser | Phe | Leu | Leu | Gly | Val | Val | Glu | Lys | Gly | Thr | Pro | Glu |
| | | | 340 | | | | | 345 | | | | | 350 | | |
| Gln | Ala | Gln | Ser | Val | Val | His | Gln | Ile | Leu | Asp | Leu | Leu | Trp | Leu | Phe |
| | | 355 | | | | | 360 | | | | | 365 | | | |
| Met | Glu | Asp | Tyr | Glu | Val | Gln | Asp | Cys | Leu | Lys | Gln | Leu | Met | Met | Ser |
| | 370 | | | | | 375 | | | | | 380 | | | | |

```
Leu Leu Arg Leu Tyr Arg Phe Ser Pro Ile Val Pro Asp Leu Gly Leu
385                 390                 395                 400

Gln Ile His Tyr Leu Arg Leu Thr Met Ser Ile Leu Arg His Glu Lys
            405                 410                 415

Ser Arg Lys Phe Leu Leu Ser Asn Val Leu Phe Asp Met Leu Arg Ser
            420                 425                 430

Val Val Phe Phe Tyr Ile Lys Ser Pro Leu Arg Val Glu Glu Ala Gly
            435                 440                 445

Leu Lys Glu Leu Ile Pro Thr Thr Trp Trp Pro His Arg Ser Ser Arg
450                 455                 460

Glu Ser Arg Asp Gly Lys Glu Ala Arg Glu Thr Thr Glu Glu Arg
465                 470                 475                 480

Gln Arg Arg Arg Ala Tyr Glu Arg Gly Cys Gln Arg Leu Lys Lys Arg
                485                 490                 495

Ile Glu Val Val Glu Glu Leu Gln Val Gln Ile Leu Lys Leu Leu Leu
            500                 505                 510

Asp Asn Lys Asp Asp Asn Gly Gly Glu Ala Ser Arg Tyr Ile Phe Leu
            515                 520                 525

Thr Lys Phe Arg Lys Phe Leu Gln Glu Asn Ala Ser Gly Arg Gly Asn
530                 535                 540

Thr Pro Val Leu Cys Pro Pro Glu Tyr Met Val Cys Phe Leu His Arg
545                 550                 555                 560

Leu Val Ser Ala Leu Arg Phe Tyr Trp Asp Glu Tyr Lys Ala Ser Asn
                565                 570                 575

Pro Arg Ala Ser Phe Ser Glu Glu Ala Tyr Ile Pro Pro Gln Ile Phe
            580                 585                 590

Tyr Asn Gly Lys Val Asp Tyr Phe Asp Leu Gln Arg Leu Gly Gly Leu
            595                 600                 605

Leu Ser His Leu Arg Lys Thr Leu Lys Asp Asp Leu Ala Ser Lys Ala
            610                 615                 620

Asn Ile Val Ile Asp Pro Leu Glu Leu Gln Ala Ala Thr Met Asp Asp
625                 630                 635                 640

Leu Asp Glu Asp Glu Glu Pro Ala Pro Ser Ala Ala Gln Val Trp Gln
                645                 650                 655

Glu Gly Gln Arg Pro Met Gln Ala Leu Ala Ile Gly Gly Ala Leu Pro
            660                 665                 670

Leu Pro Arg Pro Gly Trp Leu Ser Ser Pro Thr Leu Gly Arg Ala Asn
            675                 680                 685

Arg Phe Leu Ser Thr Ala Ala Val Ser Leu Met Thr Pro Arg Arg Leu
            690                 695                 700

Leu Ser Thr Met Glu Lys Val Lys Val Arg Ser Leu Asn Val Glu Gln
705                 710                 715                 720

Arg Thr Arg Glu Asp Ile Glu Gly Ser His Trp Asn Glu Gly Leu Leu
            725                 730                 735

Leu Gly Arg Pro Pro Glu Glu Pro Gln Pro Leu Thr Glu Asn Ser
            740                 745                 750

Leu Leu Glu Val Leu Asp Gly Thr Val Met Met Tyr Asn Leu Ser Val
            755                 760                 765

His Gln Gln Leu Gly Lys Met Val Gly Val Ser Asp Asp Val Asn Glu
            770                 775                 780

Tyr Ala Met Ala Leu Arg Asp Thr Glu Asp Lys Leu Arg Arg Cys Pro
785                 790                 795                 800
```

-continued

```
Lys Arg Arg Lys Asp Ile Leu Ala Glu Leu Thr Lys Ser Gln Lys Val
                805                 810                 815

Phe Ser Glu Lys Leu Asp His Leu Ser Arg Arg Leu Ala Trp Val His
            820                 825                 830

Ala Thr Val Tyr Ser Gln Glu Lys Met Leu Asp Ile Tyr Trp Leu Leu
            835                 840                 845

Arg Val Cys Leu Arg Thr Ile Glu His Gly Asp Arg Thr Gly Ser Leu
850                 855                 860

Phe Ala Phe Met Pro Glu Phe Tyr Leu Ser Val Ala Ile Asn Ser Tyr
865                 870                 875                 880

Ser Ala Leu Lys Asn Tyr Phe Gly Pro Val His Ser Met Glu Leu
                885                 890                 895

Pro Gly Tyr Glu Glu Thr Leu Thr Arg Leu Ala Ala Ile Leu Ala Lys
            900                 905                 910

His Phe Ala Asp Pro Arg Ile Val Gly Thr Asp Ile Arg Asp Ser Leu
            915                 920                 925

Met Gln Ala Leu Ala Ser Tyr Val Cys Tyr Pro His Ser Leu Arg Ala
            930                 935                 940

Val Glu Arg Ile Pro Glu Glu Gln Arg Ile Ala Met Val Arg Asn Leu
945                 950                 955                 960

Leu Ala Pro Tyr Glu Gln Arg Pro Trp Ala Gln Thr Asn Trp Ile Leu
                965                 970                 975

Val Arg Leu Trp Arg Gly Cys Gly Phe Gly Tyr Arg Tyr Thr Arg Leu
                980                 985                 990

Pro His Leu Leu Lys Thr Lys Pro  Glu Asp Ala Asn Leu  Pro Ser Leu
            995                 1000                1005

Gln Lys  Pro Cys Pro Ser Thr  Leu Leu Gln Gln His  Met Ala Asp
    1010                1015                 1020

Leu Leu  Arg Gln Gly Ser Asp  Val Ala Pro Ser Phe  Leu Asn Ser
    1025                1030                 1035

Val Leu  Asn Gln Leu Asn Trp  Ala Phe Ser Glu Phe  Ile Gly Met
    1040                1045                 1050

Ile Gln  Glu Ile Gln Gln Ala  Ala Glu Arg Leu Glu  Arg Asn Phe
    1055                1060                 1065

Val Asp  Ser Arg Gln Leu Lys  Val Cys Ala Thr Cys  Phe Asp Leu
    1070                1075                 1080

Ser Val  Ser Leu Leu Arg Val  Leu Glu Met Thr Ile  Thr Leu Val
    1085                1090                 1095

Pro Glu  Ile Phe Leu Asp Trp  Ser Arg Pro Thr Ser  Glu Met Leu
    1100                1105                 1110

Leu Arg  Arg Leu Ala Gln Leu  Leu Asn Gln Val Leu  Asn Arg Val
    1115                1120                 1125

Thr Ala  Glu Arg Asn Leu Phe  Asp Arg Val Val Thr  Leu Arg Leu
    1130                1135                 1140

Pro Gly  Leu Glu Ser Val Asp  His Tyr Pro Ile Leu  Val Ala Val
    1145                1150                 1155

Thr Gly  Ile Leu Val Arg Leu  Leu Val His Gly Pro  Thr Ser Glu
    1160                1165                 1170

Thr Glu  Gln Ala Thr Ser Val  Leu Leu Ala Asp Pro  Cys Phe Gln
    1175                1180                 1185

Leu Arg  Ser Ile Cys Tyr Leu  Leu Gly Gln Pro Glu  Pro Leu Ala
    1190                1195                 1200

Pro Gly  Thr Thr Leu Pro Ala  Pro Asp Arg Lys Arg  Phe Ser Leu
```

|   |   |   |   |   |   |   |   |   |   |
|---|---|---|---|---|---|---|---|---|---|
| | | 1205 | | | 1210 | | | 1215 | |
| Gln | Ser | Tyr | Thr | Asp | Tyr | Ile | Ser | Ala | Glu Glu Leu Ala Gln Val |
| | | 1220 | | | 1225 | | | 1230 | |
| Glu | Gln | Met | Leu | Ala | His | Leu | Thr | Ala | Ala Ser Ala Gln Ala Ala |
| | | 1235 | | | 1240 | | | 1245 | |
| Ala | Ala | Ser | Leu | Pro | Thr | Asn | Glu | Glu | Asp Leu Cys Pro Ile Cys |
| | | 1250 | | | 1255 | | | 1260 | |
| Tyr | Ala | His | Pro | Ile | Ser | Ala | Val | Phe | Gln Pro Cys Gly His Lys |
| | | 1265 | | | 1270 | | | 1275 | |
| Ser | Cys | Lys | Ala | Cys | Ile | Asn | Gln | His | Leu Met Asn Asn Lys Asp |
| | | 1280 | | | 1285 | | | 1290 | |
| Cys | Phe | Phe | Cys | Lys | Ala | Thr | Ile | Val | Ser Val Glu Asp Trp Asp |
| | | 1295 | | | 1300 | | | 1305 | |
| Lys | Ala | Ala | Asn | Thr | Ser | Ala | Met | Ser | Ser Ala Ala |
| | | 1310 | | | 1315 | | | 1320 | |

<210> SEQ ID NO 7
<211> LENGTH: 3945
<212> TYPE: DNA
<213> ORGANISM: Mus musculus

<400> SEQUENCE: 7

| | | | | | |
|---|---|---|---|---|---|
| atggcgtcca | aggggactgg | catgtcgttc | tcccgaaaga | gctataggct | gacctcagat | 60 |
| gctgagaagt | ccagggtcac | aggcatcgtg | caagagaaac | tactgagcga | ctatctgtac | 120 |
| cgcatctttt | cccctcctga | ccgtggaccc | gccgcagcca | ccagcaggaa | accgctaaac | 180 |
| ttccataacc | tgcctgagca | cgtggaccag | ctgctacagg | tggacagtga | agacaacgag | 240 |
| agccagggac | aagttgaagg | tcgacttggc | ccatctactg | tggtcctaga | ccacacagga | 300 |
| ggctttgagg | ggcttctcct | tgtggatgat | gacctcctgg | gggtgattgg | acacagcaac | 360 |
| tttggcacta | ccgttctaca | cacatgtgtg | tacaaaggga | agtgggtcta | cgaggtgctc | 420 |
| atctcctccc | agggcctcat | gcagatcggc | tggtgcacca | tcaactgccg | ctttaatcag | 480 |
| gaggaagggg | ttggagacac | acataactcc | tatgcctatg | acggcaaccg | agtgcgcaag | 540 |
| tggaatgtta | ccaccacgaa | ttatggcaag | gcgtgggctg | cggggacat | tgtcagctgc | 600 |
| ctaattgatc | tggatgatgg | gactctgtcc | ttctgcctga | atggcgtgtc | actgggcact | 660 |
| gccttcgaga | acctttccag | gggcctagga | atggcgtact | ccccagccat | cagcctgtca | 720 |
| ttcaaggagt | ctgtggcatt | caactttggc | agccgtcctt | tgcgctaccc | agttgcgggc | 780 |
| ttccggcccc | tgcaggaccc | tccgtttgct | gacctggtcc | gggcacagag | gttgctgggc | 840 |
| tgcttccagg | cagtgctaag | tgtggagctg | accctgtgg | aagggcggct | ggtggagacg | 900 |
| gagagctctg | agtggcagct | gcaagggcag | cccactgtcc | tcctcacgct | ggcccacatc | 960 |
| ttccatcact | ttgcaccact | gctgcgcaag | gtatacctgg | tggaggctgt | gctaatgagc | 1020 |
| ttcctgctgg | gcgttgtgga | aagggcaca | ccagagcagg | cgcagtctgt | ggtacaccag | 1080 |
| atcttggacc | tcttgtggct | cttcatggag | gactatgagg | tacaggattg | cctgaagcag | 1140 |
| ttgatgatgt | cacttctacg | tctctaccga | ttctcgccta | ttgtcccaga | cctgggtcta | 1200 |
| cagatccact | acctgcgcct | cactatgtcc | atcctgacac | acgagaagtc | ccgcaagttc | 1260 |
| ctgcttagca | atgtcctttt | tgacatgctc | cggtccgtgg | tcttcttta | tattaagagt | 1320 |
| cccctgcgtg | tggaggaagc | tggcctgaag | gaactcattc | ccaccacctg | gtggcccat | 1380 |
| cgctccagca | gggagagcag | agacggtaag | gaagcaaggg | aggagaccac | cgaagagcgg | 1440 |

```
cagcggaggc gagcctatga gcgtggctgc caaagactca agaaacgcat tgaagtggtg     1500
gaagaactgc aggtccagat cctgaagctg ctgttggaca ataaagatga caatgggggt     1560
gaagcttcta ggtacatctt tctgacaaaa ttccgaaagt tcctgcagga gaatgccagc     1620
ggccggggga acacacccgt gctctgcccc cctgagtaca tggtctgctt cctacaccgg     1680
ctggtgtctg ccttgcgctt ctattgggat gaatacaaag cttccaaccc ccgtgcttcc     1740
ttcagtgagg aggcttacat cccgccccag atcttctata tggcaaggt ggactacttt      1800 gaccttcagc gccttggggg cctcctctca caccttcgaa agacccttaa agatgacctt     1860
gcttccaaag ccaacatcgt gatcgacccc ctggagctcc aggcagccac catggatgac     1920
ctggatgagg atgaagagcc tgcccccctca gcggcccagc gtccgatgca agccctggcc     1980
atcggagggg cactgcccct gccccggcca ggctggctca gttctccaac cctgggcaga     2040
gccaaccgct tcctcagcac ggcagctgtg agcctcatga ccccacggcg gcttctgagc     2100
accatggaga aagtcaaagt tcgctcactg aatgtggaac agaggacccg tgaggacatt     2160
gagggcagcc actggaatga gggcctgctg ttggggaggc cccctgaaga gcctgagcag     2220
ccgcttaccg agaactcgct gttggaagtc ctggatggca cagtcatgat gtataacctc     2280
agcgttcacc agcagctggg caagatggtg ggtgtgtctg atgatgtcaa cgagtatgca     2340
atggccctaa gagacacaga ggacaagctc cgtcggtgcc ctaagaggag gaaggatatc     2400
cttgcagagt tgaccaagag ccagaaggtt ttctcagaaa agctggacca cctgagccgc     2460
aggcttgcct gggtccacgc cacagtctac tcacaggaga aaatgctgga tatctactgg     2520
ttactgcgtg tctgcctacg gaccattgag catgggacc gcacggggtc tctctttgcc      2580
ttcatgcctg agttctacct aagtgtggct atcaacagct acagtgccct gaagaactat     2640
tttggccctg tgcacagcat ggaggaactc ccaggctatg aagagaccct gacacgctta     2700
gctgccatcc tcgccaaaca ctttgctgac cctcgaatag taggcactga tattcgagac     2760
tcactgatga aggccctggc cagctatgtg tgctacccac actccctgcg ggctgtggaa     2820
cggattcctg aggaacagcg catcgccatg gtgaggaacc ttttggcacc ctatgagcaa     2880
cggccctggg cccagaccaa ctggatcctg gtgcggcttt ggaggggctg tgggtttggg     2940
taccgctata cacggctgcc acatctgctg aaaaccaagc cagaggatgc caatttgccc     3000
agcctccaaa agccctgccc ttcgaccttg ctacagcagc acatggcgga cctgctgcga     3060
caagggtctg atgtggcacc gagcttcctc aacagtgtcc ttaaccagct caactgggcc     3120
ttctctgagt tcatcggcat gatccaggag attcaacagg ctgctgaacg cctggagcgg     3180
aactttgtgg acagccgaca gctcaaggtc tgtgccacct gctttgacct gtcggtcagc     3240
ttgttgcgcg tcttggaaat gaccatcacg ctggtacctg aaatattcct tgactggtcc     3300
cgccctacct ctgagatgct gcttcggcgt ctggcacagc tgctgaacca ggtgctgaac     3360
cgggtgacag ctgagaggaa cctgtttgac cgtgtagtta cccctacggct acctgggctg     3420 gagagtgtgg accactaccc tatcctggtg gcagtgactg gcatcctggt acgcctcctg     3480
gtgcacggcc caacctcaga gacagagcaa gccacctctg tgctcctggc tgatccctgc     3540
ttccagcttc gttccatatg ctatctcctg gggcagccag agccctagc acctggcact     3600 accttgcctg cccctgaccg gaaacgcttc tctctacaga gttatacaga ttatatcagc     3660
gctgaggagc tggcccaggt ggaacagatg ctggctcacc tgaccgctgc atctgcccag     3720
gcggccgccg cctccctgcc caccaatgaa gaggacctct gcccaatctg ctacgccac      3780 cccatctctg ctgtgttcca gccttgtggt cacaaatcct gcaaagcctg catcaaccag     3840
```

```
cacctgatga acaacaagga ctgcttcttc tgcaaagcca ccattgtatc tgtagaggac      3900
tgggacaagg cagccaacac aagcgccatg tcctcagctg cctag                     3945
```

<210> SEQ ID NO 8
<211> LENGTH: 41
<212> TYPE: DNA
<213> ORGANISM: Artificial Sequence
<220> FEATURE:
<223> OTHER INFORMATION: Synthesized sequence

<400> SEQUENCE: 8

```
ccagaacatt tggaccagtt ggctacaggt ggacaatgag g                           41
```

<210> SEQ ID NO 9
<211> LENGTH: 41
<212> TYPE: DNA
<213> ORGANISM: Artificial Sequence
<220> FEATURE:
<223> OTHER INFORMATION: Synthesized sequence

<400> SEQUENCE: 9

```
gtgctgagtg atgccaggac acatcctgga agagaacatc c                           41
```

<210> SEQ ID NO 10
<211> LENGTH: 26
<212> TYPE: PRT
<213> ORGANISM: Artificial Sequence
<220> FEATURE:
<223> OTHER INFORMATION: Synthesized sequence
<220> FEATURE:
<221> NAME/KEY: MISC_FEATURE
<222> LOCATION: (12)..(12)
<223> OTHER INFORMATION: Serine (S) can be altered by Proline (P)
<220> FEATURE:
<221> NAME/KEY: MISC_FEATURE
<222> LOCATION: (17)..(17)
<223> OTHER INFORMATION: Serine (S) can be altered by Proline (P)
<220> FEATURE:
<221> NAME/KEY: MISC_FEATURE
<222> LOCATION: (17)..(17)
<223> OTHER INFORMATION: The Serine (S) may be phosphorylated

<400> SEQUENCE: 10

Asp Glu Leu Arg Asp Ser Asp Ser Val Cys Asp Ser Gly Val Glu Thr
1               5                   10                  15

Ser Phe Arg Lys Leu Ser Phe Thr Glu Ser
            20                  25

<210> SEQ ID NO 11
<211> LENGTH: 19
<212> TYPE: RNA
<213> ORGANISM: Artificial Sequence
<220> FEATURE:
<223> OTHER INFORMATION: Synthesized sequence

<400> SEQUENCE: 11

```
gcgcuacuau ugggaugaa                                                    19
```

<210> SEQ ID NO 12
<211> LENGTH: 19
<212> TYPE: RNA
<213> ORGANISM: Artificial Sequence
<220> FEATURE:
<223> OTHER INFORMATION: Synthesized sequence

<400> SEQUENCE: 12
caacugggcc uucucugaa                                              19

<210> SEQ ID NO 13
<211> LENGTH: 19
<212> TYPE: RNA
<213> ORGANISM: Artificial Sequence
<220> FEATURE:
<223> OTHER INFORMATION: Synthesized sequence

<400> SEQUENCE: 13
gcacauggcg gaccuccua                                              19

<210> SEQ ID NO 14
<211> LENGTH: 19
<212> TYPE: RNA
<213> ORGANISM: Artificial Sequence
<220> FEATURE:
<223> OTHER INFORMATION: Synthesized sequence

<400> SEQUENCE: 14
ggugaagcuu cuagguaua                                              19

<210> SEQ ID NO 15
<211> LENGTH: 19
<212> TYPE: RNA
<213> ORGANISM: Artificial Sequence
<220> FEATURE:
<223> OTHER INFORMATION: Synthesized sequence

<400> SEQUENCE: 15
gcuaauugaa cacgcagaa                                              19

<210> SEQ ID NO 16
<211> LENGTH: 19
<212> TYPE: RNA
<213> ORGANISM: Artificial Sequence
<220> FEATURE:
<223> OTHER INFORMATION: Synthesized sequence

<400> SEQUENCE: 16
gcacguaggu ggcguuguu                                              19

<210> SEQ ID NO 17
<211> LENGTH: 19
<212> TYPE: RNA
<213> ORGANISM: Artificial Sequence
<220> FEATURE:
<223> OTHER INFORMATION: Synthesized sequence

<400> SEQUENCE: 17
cagaaugccg cgugcgagu                                              19

<210> SEQ ID NO 18
<211> LENGTH: 19
<212> TYPE: RNA
<213> ORGANISM: Artificial Sequence
<220> FEATURE:
<223> OTHER INFORMATION: Synthesized sequence

<400> SEQUENCE: 18
agagaugagc ugacggaaa                                              19

<210> SEQ ID NO 19
<211> LENGTH: 22
<212> TYPE: DNA
<213> ORGANISM: Artificial Sequence -continued

```
<220> FEATURE:
<223> OTHER INFORMATION: Synthesized sequence
<220> FEATURE:
<221> NAME/KEY: misc_feature
<222> LOCATION: (22)..(22)
<223> OTHER INFORMATION: C is connected to biotin

<400> SEQUENCE: 19
agttgagggg actttcccag gc                                               22

<210> SEQ ID NO 20
<211> LENGTH: 1333
<212> TYPE: PRT
<213> ORGANISM: Oryctolagus cuniculus
<220> FEATURE:
<221> NAME/KEY: misc_feature
<222> LOCATION: (624)..(633)
<223> OTHER INFORMATION: Xaa can be any naturally occurring amino acid

<400> SEQUENCE: 20
```

Met Ala Ser Lys Gly Ala Gly Val Pro Leu Ser Arg Lys Ser Tyr Arg
1               5                   10                  15

Leu Thr Ser Glu Thr Glu Arg Pro Arg Val Thr Gly Ile Val His Glu
            20                  25                  30

Lys Leu Leu Asn Asp Tyr Leu His Arg Ile Phe Ser Ser Pro Asp His
        35                  40                  45

Ala Thr Pro Thr Ala Thr Ser Arg Lys Pro Leu Asn Phe Gln Asn Leu
    50                  55                  60

Pro Glu His Leu Asp Gln Leu Leu Gln Val Asp Ser Glu Asp Glu Glu
65                  70                  75                  80

Ser Gln Gly Gln Val Glu Gly Arg Leu Gly Pro Ser Thr Val Val Leu
                85                  90                  95

Asp His Thr Gly Gly Phe Glu Gly Leu Leu Leu Val Asp Asp Asp Leu
            100                 105                 110

Leu Gly Val Ile Gly His Ser Asn Phe Gly Thr Ile Arg Ser Thr Thr
        115                 120                 125

Cys Val Tyr Lys Gly Lys Trp Val Tyr Glu Val Leu Ile Ser Ser Gln
    130                 135                 140

Gly Leu Met Gln Ile Gly Trp Cys Thr Ile Asn Cys Arg Phe Asn Gln
145                 150                 155                 160

Glu Glu Gly Val Gly Asp Thr His Asn Ser Tyr Ala Tyr Asp Gly Asn
                165                 170                 175

Arg Val Arg Lys Trp Asn Val Thr Thr Thr Asn Tyr Gly Lys Ala Trp
            180                 185                 190

Ala Ala Gly Asp Ile Val Ser Cys Leu Ile Asp Leu Asp Asp Gly Thr
        195                 200                 205

Leu Ser Phe Cys Leu Asn Gly Val Ser Leu Gly Thr Ala Phe Glu Asn
    210                 215                 220

Leu Ser Arg Gly Leu Gly Met Ala Tyr Phe Pro Ala Ile Ser Leu Ser
225                 230                 235                 240

Phe Lys Glu Ser Val Ala Phe Asn Phe Gly Ser Arg Pro Leu Arg Tyr
                245                 250                 255

Pro Val Ala Gly Tyr Arg Pro Leu Gln Asp Pro Pro Cys Ala Asp Leu
            260                 265                 270

Thr Arg Ala Gln Arg Leu Leu Gly Cys Phe Arg Ala Val Leu Ser Val
        275                 280                 285

Glu Leu Asp Pro Met Glu Gly Arg Leu Val Glu Lys Glu Ser Ser Glu
    290                 295                 300

-continued

```
Trp Gln Leu Gln Gly Gln Pro Thr Val Leu Thr Leu Ala His Ile
305                 310                 315                 320

Phe His Arg Phe Ala Pro Leu Leu His Gln Val Tyr Leu Val Glu Ala
            325                 330                 335

Val Leu Met Ser Phe Leu Leu Gly Ile Val Glu Lys Ala Thr Pro Ala
        340                 345                 350

Gln Ala Gln Ser Ala Val His Gln Ile Leu Asp Leu Leu Trp Leu Phe
    355                 360                 365

Met Glu Asp Tyr Glu Val Gln Asp Cys Leu Lys Gln Leu Met Met Ser
370                 375                 380

Leu Leu Arg Leu Tyr Arg Phe Ser Pro Ile Val Pro Asp Leu Gly Leu
385                 390                 395                 400

Gln Ile His Tyr Leu Arg Leu Thr Ile Ala Ile Leu Arg His Gln Lys
            405                 410                 415

Ser Arg Lys Phe Leu Leu Ser Asn Val Leu Phe Asp Val Leu Arg Ser
        420                 425                 430

Val Val Phe Phe Tyr Ile Lys Ser Pro Leu Arg Val Glu Glu Ala Gly
    435                 440                 445

Leu Gln Glu Leu Ile Pro Thr Thr Trp Trp Pro His Arg Ser Ser Arg
450                 455                 460

Glu Gly Lys Asp Ser Ala Glu Asp Arg Ala Glu Ala Ala Glu Glu Arg
465                 470                 475                 480

Pro Arg Arg Arg Ala Tyr Glu Arg Gly Cys Gln Arg Leu Lys Lys Arg
            485                 490                 495

Ile Glu Val Val Glu Ala Leu Gln Val Gln Ile Leu Lys Leu Leu Leu
        500                 505                 510

Asp Asn Lys Asp Asp Asn Gly Gly Glu Ala Ser Arg Tyr Ile Phe Leu
    515                 520                 525

Thr Lys Phe Arg Lys Phe Leu Gln Glu Asn Ala Ser Gly Arg Gly Asn
530                 535                 540

Met Pro Met Leu Cys Pro Pro Glu Tyr Met Val Cys Phe Leu His Arg
545                 550                 555                 560

Leu Ile Ser Leu Arg Tyr Tyr Trp Asp Glu Tyr Lys Ala Ser Asn Pro
            565                 570                 575

Arg Ala Ser Cys Ser Glu Glu Ala Tyr Ile Pro Pro Gln Val Phe Tyr
        580                 585                 590

Asn Gly Lys Val Asp Tyr Phe Asp Leu Gln Arg Leu Gly Gly Leu Leu
    595                 600                 605

Ser His Leu Arg Lys Thr Leu Lys Gly Val Cys Ser Pro Leu Gly Xaa
610                 615                 620

Xaa Xaa Xaa Xaa Xaa Xaa Xaa Xaa Ala Thr Thr Met Asp Asp Leu
625                 630                 635                 640

Asp Glu Asp Glu Glu Pro Ala Pro Ala Ala Gly Val Leu His Lys
            645                 650                 655

Gly Gln Arg Pro Val Gln Ala Leu Ala Val Gly Gly Ala Leu Pro Leu
        660                 665                 670

Pro Arg Pro Gly Trp Leu Ser Ser Pro Thr Leu Gly Arg Ala Asn Arg
    675                 680                 685

Phe Leu Ser Thr Ala Ala Val Ser Leu Met Thr Pro Arg Arg Pro Leu
690                 695                 700

Ser Thr Ser Glu Lys Val Lys Val Arg Thr Leu Ser Val Glu Gln Arg
705                 710                 715                 720
```

```
Thr Arg Glu Asp Ile Glu Gly Ser His Trp Asn Glu Gly Leu Leu Leu
                725                 730                 735

Gly Arg Pro Pro Glu Glu Pro Glu Gln Pro Leu Thr Glu Asn Ser Leu
            740                 745                 750

Leu Glu Val Leu Asp Gly Ala Ile Met Met Tyr Asn Leu Ser Val His
        755                 760                 765

Gln Gln Leu Gly Lys Met Val Gly Val Ser Asp Val Asn Glu Tyr
    770                 775                 780

Ala Thr Ala Leu Arg Asp Thr Glu Asp Lys Ile Arg Arg Cys Pro Lys
785                 790                 795                 800

Arg Arg Lys Asp Ile Leu Ala Glu Leu Thr Lys Ser Gln Lys Val Phe
                805                 810                 815

Ser Glu Lys Leu Asp His Leu Ser Arg Arg Leu Ala Trp Val His Ala
            820                 825                 830

Thr Val Tyr Ser Gln Glu Lys Met Leu Asp Ile Tyr Trp Leu Leu Arg
        835                 840                 845

Val Cys Leu Arg Thr Ile Glu His Gly Asp Arg Thr Gly Ser Leu Phe
    850                 855                 860

Ala Phe Met Pro Glu Phe Tyr Leu Ser Val Ala Ile Asn Ser Tyr Ser
865                 870                 875                 880

Ala Leu Lys Asn Tyr Phe Gly Pro Val His Ser Met Glu Glu Leu Pro
                885                 890                 895

Gly Tyr Glu Glu Thr Leu Thr Arg Leu Ala Ala Ile Leu Ala Lys His
            900                 905                 910

Phe Ala Asp Thr Arg Ile Val Gly Thr Asp Ile Arg Asp Ser Leu Met
        915                 920                 925

Gln Ala Leu Ala Ser Tyr Val Cys Tyr Pro His Ser Leu Arg Ala Val
    930                 935                 940

Glu Arg Ile Pro Glu Glu Gln Arg Val Ala Met Val Arg Ser Leu Leu
945                 950                 955                 960

Ala Pro Tyr Glu Gln Arg Pro Trp Ala Gln Thr Asn Trp Ile Leu Val
                965                 970                 975

Arg Leu Trp Arg Gly Cys Gly Phe Gly Tyr Arg Tyr Thr Arg Leu Pro
            980                 985                 990

His Leu Leu Lys Thr Lys Pro Glu Asp Ala Ser Leu Pro Ser Leu Gln
        995                 1000                1005

Lys Pro Cys Pro Ser Thr Leu Leu Gln Gln His Met Ala Asp Leu
    1010                1015                1020

Leu Arg Gln Gly Pro Asp Val Ala Pro Ser Phe Leu Asn Ser Val
    1025                1030                1035

Leu Asn Gln Leu Asn Trp Ala Phe Ser Glu Phe Ile Gly Met Ile
    1040                1045                1050

Gln Glu Ile Gln Gln Ala Ala Glu Arg Leu Glu Arg Asn Phe Val
    1055                1060                1065

Asp Ser Arg Gln Leu Lys Val Cys Ala Thr Cys Phe Asp Leu Ser
    1070                1075                1080

Val Ser Leu Leu Arg Val Leu Glu Met Thr Ile Thr Leu Val Pro
    1085                1090                1095

Glu Ile Phe Leu Asp Trp Ala Arg Pro Thr Ser Glu Met Leu Leu
    1100                1105                1110

Arg Arg Leu Ala Gln Leu Leu Asn Gln Val Leu Asn Arg Val Thr
    1115                1120                1125

Ala Glu Arg Asn Leu Phe Asp Arg Val Val Thr Leu Arg Leu Pro
```

```
                1130                1135                1140
Gly Leu Glu Ser Val Asp His Tyr Pro Ile Leu Val Ala Val Thr
        1145                1150                1155
Gly Ile Leu Val Arg Leu Leu Val His Gly Pro Ser Ser Glu Thr
        1160                1165                1170
Glu Arg Ala Thr Ser Val Leu Leu Ala Asp Pro Cys Phe Gln Leu
        1175                1180                1185
Arg Ser Ile Ser Tyr Leu Leu Gly Gln Pro Glu Pro Pro Ala Pro
        1190                1195                1200
Gly Ala Ala Leu Pro Ala Pro Asp Arg Lys Arg Phe Ser Leu Gln
        1205                1210                1215
Ser Tyr Ala Asp Tyr Ile Ser Ala Glu Glu Leu Ala Gln Val Glu
        1220                1225                1230
Gln Met Leu Ala His Leu Thr Ser Ala Ser Ala Gln Ala Ala Ala
        1235                1240                1245
Ala Ser Leu Pro Thr Ser Glu Glu Asp Leu Cys Pro Ile Cys Tyr
        1250                1255                1260
Ala His Pro Ile Ser Ala Val Phe Gln Pro Cys Gly His Lys Ser
        1265                1270                1275
Cys Lys Ala Cys Ile Asp Gln His Leu Met Asn Asn Lys Asp Cys
        1280                1285                1290
Phe Phe Cys Lys Ala Thr Ile Val Ser Val Glu Asp Trp Glu Lys
        1295                1300                1305
Gly Ala Ser Ala Ser Gly Ala Ala Ala Ala Ala Thr Thr Thr
        1310                1315                1320
Thr Thr Thr Thr Ser Thr Ser Ser Ala Ala
        1325                1330

<210> SEQ ID NO 21
<211> LENGTH: 405
<212> TYPE: PRT
<213> ORGANISM: Mus musculus

<400> SEQUENCE: 21

Met Phe Val Gln Glu Glu Lys Ile Phe Ala Gly Lys Val Leu Arg Leu
1               5                   10                  15

His Ile Cys Ala Ser Asp Gly Ala Glu Trp Leu Glu Glu Ala Thr Glu
            20                  25                  30

Asp Thr Ser Val Glu Lys Leu Lys Glu Arg Cys Leu Lys His Cys Ala
        35                  40                  45

His Gly Ser Leu Glu Asp Pro Lys Ser Ile Thr His His Lys Leu Ile
    50                  55                  60

His Ala Ala Ser Glu Arg Val Leu Ser Asp Ala Arg Thr Ile Leu Glu
65                  70                  75                  80

Glu Asn Ile Gln Asp Gln Asp Val Leu Leu Leu Ile Lys Lys Arg Ala
                85                  90                  95

Pro Ser Pro Leu Pro Lys Met Ala Asp Val Ser Ala Glu Glu Lys Lys
            100                 105                 110

Lys Gln Asp Gln Lys Ala Pro Asp Lys Glu Ala Ile Leu Arg Ala Thr
        115                 120                 125

Ala Asn Leu Pro Ser Tyr Asn Met Asp Arg Ala Ala Val Gln Thr Asn
    130                 135                 140

Met Arg Asp Phe Gln Thr Glu Leu Arg Lys Ile Leu Val Ser Leu Ile
145                 150                 155                 160
```

-continued

```
Glu Val Ala Gln Lys Leu Leu Ala Leu Asn Pro Asp Ala Val Glu Leu
                165                 170                 175

Phe Lys Lys Ala Asn Ala Met Leu Asp Glu Asp Glu Asp Glu Arg Val
                180                 185                 190

Asp Glu Ala Ala Leu Arg Gln Leu Thr Glu Met Gly Phe Pro Glu Asn
                195                 200                 205

Arg Ala Thr Lys Ala Leu Gln Leu Asn His Met Ser Val Pro Gln Ala
                210                 215                 220

Met Glu Trp Leu Ile Glu His Ala Glu Asp Pro Thr Ile Asp Thr Pro
225                 230                 235                 240

Leu Pro Gly Gln Ala Pro Pro Glu Ala Glu Gly Ala Thr Ala Ala Ala
                245                 250                 255

Ser Glu Ala Ala Ala Gly Ala Ser Ala Thr Asp Glu Glu Ala Arg Asp
                260                 265                 270

Glu Leu Thr Glu Ile Phe Lys Lys Ile Arg Arg Lys Arg Glu Phe Arg
                275                 280                 285

Ala Asp Ala Arg Ala Val Ile Ser Leu Met Glu Met Gly Phe Asp Glu
                290                 295                 300

Lys Glu Val Ile Asp Ala Leu Arg Val Asn Asn Asn Gln Gln Asn Ala
305                 310                 315                 320

Ala Cys Glu Trp Leu Leu Gly Asp Arg Lys Pro Ser Pro Glu Glu Leu
                325                 330                 335

Asp Lys Gly Ile Asp Pro Asp Ser Pro Leu Phe Gln Ala Ile Leu Asp
                340                 345                 350

Asn Pro Val Val Gln Leu Gly Leu Thr Asn Pro Lys Thr Leu Leu Ala
                355                 360                 365

Phe Glu Asp Met Leu Glu Asn Pro Leu Asn Ser Thr Gln Trp Met Asn
                370                 375                 380

Asp Pro Glu Thr Gly Pro Val Met Leu Gln Ile Ser Arg Ile Phe Gln
385                 390                 395                 400

Thr Leu Asn Arg Thr
                405
```

What is claimed is:

1. A method of treating cancer in a subject comprising the step of administering to said subject a therapeutically effective amount of:
   (b) an expression vector comprising a nucleic acid that encodes a fused protein comprising the KPC1 sequence as set forth in SEQ ID NO: 4,
   wherein said method comprises administering the expression vector as described in (b).

2. The method of claim 1, wherein said expression vector is comprised within a pharmaceutical composition comprising a pharmaceutically acceptable carrier.

3. The method of claim 1, wherein the cancer is breast cancer, bone osteosarcoma, or glioblastoma.

4. A method of treating cancer in a subject comprising the step of administering to said subject a therapeutically effective amount of:
   (b) an expression vector comprising a nucleic acid that encodes a fused protein comprising the KPC1 sequence as set forth in SEQ ID NO: 4,
   wherein said fused protein comprises an immunoglobulin, an antibody, an albumin, an albumin-binding moiety, or a combination thereof.

5. The method of claim 4, wherein said immunoglobulin comprises IgG.

6. The method of claim 4, wherein said expression vector is comprised within a pharmacuetical composition comprising a pharmaceutically acceptable carrier.

7. The method of claim 4, wherein the cancer is breast cancer, bone osteosarcoma, or glioblastoma.

* * * * *